(12) United States Patent
Medford et al.

(10) Patent No.: US 9,062,320 B2
(45) Date of Patent: Jun. 23, 2015

(54) BIOLOGICAL SYSTEMS INPUT-OUTPUT RESPONSE SYSTEM AND PLANT SENTINELS

(75) Inventors: June Medford, Fort Collins, CO (US); Mauricio S. Antunes, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 13/437,828

(22) Filed: Apr. 2, 2012

(65) Prior Publication Data
US 2013/0007913 A1     Jan. 3, 2013

Related U.S. Application Data

(63) Continuation of application No. 11/789,560, filed on Apr. 25, 2007, now Pat. No. 8,148,605.

(60) Provisional application No. 60/795,614, filed on Apr. 26, 2006.

(51) Int. Cl.
*C12N 15/82* (2006.01)

(52) U.S. Cl.
CPC ....... *C12N 15/825* (2013.01); *C12Y 302/01023* (2013.01); *C12Y 302/01031* (2013.01); *C12N 15/8237* (2013.01); *C12N 15/8241* (2013.01); *C12N 15/8238* (2013.01); *C12Y 113/12007* (2013.01)

(58) Field of Classification Search
None
See application file for complete search history.

(56) References Cited

U.S. PATENT DOCUMENTS

| 5,977,441 | A | 11/1999 | Oliver et al. | |
|---|---|---|---|---|
| 6,417,429 | B1 | 7/2002 | Hein et al. | |
| 8,148,605 | B2 * | 4/2012 | Medford et al. | 800/282 |
| 2004/0043394 | A1 | 3/2004 | Ohkawa | |
| 2005/0114923 | A1 | 5/2005 | Blaylock et al. | |

FOREIGN PATENT DOCUMENTS

| JP | 03291566 | 12/1991 |
|---|---|---|
| WO | WO-03/100068 | 12/2003 |

OTHER PUBLICATIONS

Ikeda, M. et al. Plant and Cell Physiology (2009) vol. 50, No. 5; pp. 970-975.*
Yang, Z. et al. (2005) Plant Molecular Biology vol. 58:585-596.*
Tiwari, S. et al. The Plant Cell (Feb. 2004) vol. 16:533-543.*
Baumberger et al., "Whole-Genome Comparison of Leucine-Rich Repeat Extensins in Arabidopsis and Rice. A Conserved Family of Cell Wall Proteins Form a Vegetative and Reproductive Clade," *Plant Physiol.*, 131(3):1313-1326; 2003.
Bauer et al., "Sensitivity of Different Ecotypes and Mutants of *Arabidopsis thaliana* toward the Bacterial Elicitor Flagellin Correlates with the Presence of Receptor-binding Sites," *J of Biol. Chem.*, 276(49):45669-45676; 2001.
Chandler et al., "Gene activation and gene silencing," *Plant Physiology*, 125:145-148; Jan. 2001.
Dwyer et al., "Periplasmic binding proteins: a versatile superfamily for protein engineering," *Current Opinion in Structural Biology*, 14:495-504; 2004.
Hayden, "Key protein-design papers challenged, Chemists question stability of proteins from 2003 Nature study," *Nature*, 461, 859; Oct. 14, 2009.
Kiba et al., "The Type-A Response Regulator, ARR15, Acts as a Negative Regulator in the Cytokinin-Mediated Signal Transduction in *Arabidopsis thaliana*," *Plant Cell Physiol.*, 44(8): 868-874; 2003.
Li et al., "Amino acids determining enzyme-substrate specificity in prokaryotic and eukaryotic protein kinases," *PNAS*, 100(8); 4463-4468; Apr. 4, 2003.
Looger et al., "Computational design of receptor and sensor proteins with novel functions," *Nature*, 423:185-190; 2003.
Makino et al., "Nucleotide Sequence of the *phoB* Gene the Positive Regulatory Gene for the Phosphate Regulatory of *Escherichia coli* K-12," *The Research Institute for Microbial Diseases*, Osaka University; Academic Press, 190(37-44); 1986.
Nagata et al., "Engineering expression of bacterial polyphosphate kinase in tobacco for mercury remediation," *Appl. Microbial Biotechnol.*, 72:777-782; Mar. 3, 2006.
Schreier et al., "Computational design of ligand binding is not a solved problem," *PNAS*, 106:44:18491-96; Nov. 3, 2009.
Stewart, "Plants that Detect Landmines, and other biosensors," http://www.isb.vt.edu/articles/feb0106.htm; U of NC at Greensboro and Transgreenix Corporation; Feb. 2001.
Stocker et al., "Development of a Set of Simple Bacterial Biosensors for Quantitative and Rapid Measurements of Arsenite and Arsenate in Potable Water," *Environ Sci & Tech.*, 37(20):4743-4750; 2003.
Yamada et al., "The Arabidopsis AHK4 Histidine Kinase is a Cytokinin-Binding Receptor that Transduces Cytokinin Signals Across the Membrane," *Plant Cell Physiol.*, 42(9):1017-1023, 2001.
Yang, "Telltale plants," *Fortune*, 154(12) Dec. 11, 2006.
Yokobayashi et al. "Directed evolution of a genetic circuit," *PNAS*, 99(26):16587-16591; Dec. 24, 2002.

* cited by examiner

*Primary Examiner* — Russell Kallis
(74) *Attorney, Agent, or Firm* — Dentons US LLP

(57) ABSTRACT

A eukaryotic input circuit: computationally designed receptors, synthetic eukaryotic signal transduction pathways, and a synthetic signal sensitive promoter that allow highly specific transcriptional induction in response to an externally provided ligand is disclosed. The input circuit is able to specifically bind a targeted substance and transmit a signal to the nucleus where transcription of a gene is activated. An output circuit serves as a simple readout system of the substance detected by the input circuit. The readout circuit exemplified here is a degreening circuit which causes plants to turn white. Activation of the degreening circuit can be detected by eye, or remotely with a variety of machines (hand-held, aircraft or satellite based) and is also resettable. When linked the input circuit if operably linked to the output circuit, produces a functional plant detector.

31 Claims, 30 Drawing Sheets

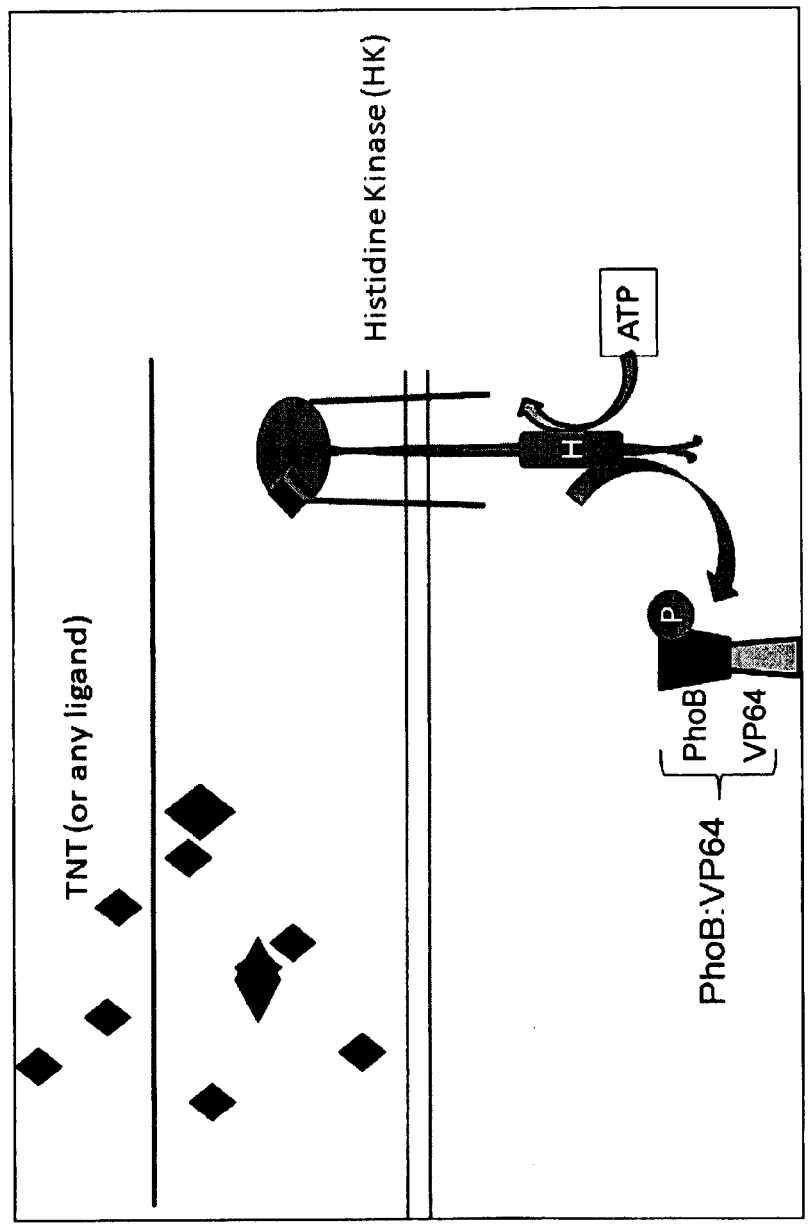

BIOLOGICAL SYSTEMS INPUT-OUTPUT RESPONSE SYSTEM AND PLANT SENTINELS

CROSS REFERENCE TO RELATED APPLICATIONS

This application is a continuation of U.S. application Ser. No. 11/789,560, filed Aug. 25, 2007, which application claims the benefit of U.S. Provisional Patent Application Ser. No. 60/795,614 filed Apr. 26, 2006, both of the disclosures of which are incorporated herein by reference in their entireties including their respective sequence listings.

ACKNOWLEDGEMENT OF FEDERAL RESEARCH SUPPORT

This invention was made, at least in part, with government support under N00014-03-1-0567 awarded by the United States Navy. Accordingly, the United States government has certain rights in this invention.

REFERENCE TO SEQUENCE LISTING

The present application incorporates by reference a file named 1511-002 Medford sequences.ST25.txt including SEQ ID NO:1 to SEQ ID NO:41, provided in a computer readable form and filed with the present application. The sequence listing recorded on the CD-ROM is identical to the written (on paper) sequence listing provided herein.

BACKGROUND OF THE INVENTION

The present invention relates to plant molecular biology, to signal transduction from outside the plant to the nucleus and to systems for sensing a target substance of interest in the environment and inducing gene expression in response thereto, along with a novel plant biomarker useful for reporting the detection of biological and chemical agents and environmental pollutants based on the loss of green color in plants. All publications cited in this application are herein incorporated by reference.

There have been increasing threats from terrorists which present an urgent need for simple and robust detectors for harmful biological or chemical agents. Current detectors of biological and chemical agents involve electronic and/or vacuum-like mechanisms to sample the air or the environment. All current means to detect terrorist agents are costly and require continuous maintenance. The high and continuous cost significantly limits the ability to detect biological and chemical weapons as well as environmental pollutants.

Each fall, plants display a dramatic loss in green color. The bright yellow, red, and orange colors are unmasked by the tremendous loss in the green chlorophyll pigments. Consequently, the loss of green color in plants is a phenomenon that most people readily recognize. This metabolic degreening process is not unique to the foliage of deciduous trees. A metabolic degreening is found in all plants including evergreens and algae (Matile et al., 1999).

The green color in plants is due to a pigment known as chlorophyll. Most higher green plants contain two types of chlorophyll, chlorophyll a and chlorophyll b. Each molecule has a porphyrin-like ring attached to a long hydrocarbon tail. Chlorophyll a and chlorophyll b differ only in a side group of ring II. In most plants, chlorophyll a is the dominant form with lesser amounts of chlorophyll b. The two forms of chlorophyll undergo a simple cyclic interconversion. Chlorophyll is synthesized in the a form and can be converted to the b form through chlorophyll a oxygenase; chlorophyll b is converted back to chlorophyll a through the action of chlorophyll b reductase (Malkin and Niyogi, 2000; Thomas et al., 2002).

The biosynthetic pathway for chlorophyll is very well known (Malkin and Niyogi, 2000). Chlorophyll biosynthesis begins with glutamic acid. Through nine biochemical steps glutamic acid is converted to a four-ring structure, protoporphyrin IX. Magnesium chelatase adds magnesium to the ring structure. In two additional steps, monovinyl protochlorophyllide a is formed. The enzyme protochlorophyllide oxidoreductase (POR) reduces the monovinyl protochlorophyllide molecule to form chlorophyllide a. Importantly, the POR enzyme controls the rate-limiting step in chlorophyll biosynthesis. Chlorophyllide a has a light green color and differs from chlorophyll by lacking the long hydrocarbon tail. The chlorophyllide molecule is converted to the darker green chlorophyll molecule by the enzyme chlorophyll synthetase, which adds a twenty-carbon phytol tail. Like most biological molecules, steady state levels of chlorophyll are maintained by a combination of biosynthesis and catabolism with the half-life of chlorophyll in a green plant being approximately 50 hours (Matile et al., 1999).

Like chlorophyll biosynthesis, the chlorophyll breakdown pathway is also very well characterized (Matile et al., 1999; Tsuchiya et al., 1999; Dangl et al., 2000). Chlorophyllase, one of the major enzymes involved in the first step of chlorophyll breakdown, removes the hydrophobic, twenty carbon phytol tail from chlorophyll (Matile et al., 1999; Tsuchiya et al., 1999; Dangl et al., 2000; Benedetti and Arruda, 2002). Similar to the biosynthetic pathway, chlorophyll without the phytol tail becomes the light green molecule, chlorophyllide. The lack of the phytol tail also changes solubility; chlorophyllide is soluble in aqueous solutions whereas chlorophyll is soluble in organic solvents.

The chlorophyllide a molecule is converted to pheophorbide a by removal of the magnesium by the enzyme magnesium dechelatase (Matile et al., 1999; Dangl et al., 2000; Takamiya et al., 2000). A red-colored compound, red chlorophyll catabolite (RCC), forms next through the action of the enzyme pheophorbide a oxygenase (Hortensteiner et al., 1998; Thomas et al., 2002). Next, the enzyme RCC reductase acts to produce fluorescent chlorophyll catabolite (FCC). Subsequently, various enzymes convert FCC to nonfluorescent chlorophyll catabolites. Nonfluorescent chlorophyll catabolite molecules accumulate in the plant's vacuole.

Importantly, the chlorophyll degradation pathway is not thought to be part of the system involved in steady-state regulation of chlorophyll levels, because chlorophyll catabolites have never been found in green cells with steady chlorophyll levels (Matile et al., 1999). This suggests that induction of genes in the chlorophyll degradation pathway will lead to the rapid breakdown of chlorophyll. Indeed, transgenic plants with constitutive expression of the chlorophyllase gene had massive accumulation of the enzyme's product, chlorophyllide (Benedetti and Arruda, 2002). These plants retained the ability to synthesize chlorophyll and hence retained a green color.

Plants, because of their sessile nature, have evolved sophisticated mechanisms for sensing and responding to their environment and substances in their environment (Trewavas, 2000, 2002). The presence of a plant cell wall, now understood to be a complex matrix, does not deter the ability of green plants to detect analytes (Dangl et al., 2000). Indeed, plants are capable of detecting analytes intracellularly (e.g., soluble or cytoplasmic analytes such as chemicals or phytohormones) or extracellularly (e.g., certain pathogens, chemicals and gaseous hormones such as ethylene). Normal cytoplasmic analytes of plants are detected with a variety of receptors (Fujisawa et al., 2001; Friml et al., 2002) whereas normal extracellular analytes are sensed with membrane receptors (Dangl and Jones, 2001).

Sensing substances and linking the sensing to a response were recently developed in bacterial systems (Looger et al., 2003; Helling a et al., 1991). These studies and related (Swartz J R, 2001; Allert et al., 2004; US Patent Application Publications 2004/229290 and 2004/0118681 and U.S. Pat. Nos. 6,977,180 and 6,521,446) show that (1) sensor or receptor proteins can, for a substance of interest, be designed in a computer and (2) the binding of the specific substance to the computationally designed receptor can be linked to a bacterial transcriptional response system. Receptors for the bacterial system that have been designed include ones for an organophosphate surrogate of the nerve agent soman, heavy metals such as $Zn^{2+}$, explosives such as TNT, herbicides such as glyphosate, and environmental pollutants such as MTBE.

There is a need in the art for monitoring systems characterized by fast feedback, ability to reset, capacity for remote evaluation, low cost to allow widespread use, ease of public recognition and the ability for operation and assessment without technically sophisticated operators or equipment.

The foregoing examples of the related art and limitations related therewith are intended to be illustrative and not exclusive. Other limitations of the related art will become apparent to those of skill in the art upon a reading of the specification and a study of the drawings.

SUMMARY OF THE INVENTION

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In one aspect of the present invention, a DNA construct is provided comprising a plant operable promoter operably linked to a nucleic acid sequence encoding a sensor protein, said protein comprising a secretory sequence for directing the protein to the extracellular space of a plant cell and a binding region specific for a target substance of interest, wherein said protein undergoes a conformational change when the target substance is bound.

In another aspect of the present invention, a DNA construct is provided comprising a plant operable promoter operably linked to a nucleic acid sequence encoding a sensor protein, said protein comprising a secretory sequence for directing the protein to the extracellular space of a plant cell and a binding region specific for a target substance of interest, wherein said protein undergoes a conformational change when the target substance is bound, wherein the target substance is a nerve gas, a heavy metal, a poison, a pollutant, a toxin, an herbicide, a polycyclic aromatic hydrocarbon, a benzene, a toluene, a xylene, a halogenated (chloro, fluoro, and chlorofluoro) hydrocarbon, a steroid or other hormone, an explosive, or a degradation product of one of the foregoing compounds.

In a further aspect of the present invention, a DNA construct is provided comprising a plant operable promoter operably linked to a nucleic acid sequence encoding a sensor protein, said protein comprising a secretory sequence for directing the protein to the extracellular space of a plant cell and a binding region specific for a target substance of interest, wherein said protein undergoes a conformational change when the target substance is bound, wherein the target substance is a nerve gas, a heavy metal, a poison, a pollutant, a toxin, an herbicide, a polycyclic aromatic hydrocarbon, a benzene, a toluene, a xylene, a halogenated (chloro, fluoro, and chlorofluoro) hydrocarbon, a steroid or other hormone, an explosive, or a degradation product of one of the foregoing compounds, and wherein the encoded sensor protein specifically binds trinitrotoluene.

In another aspect of the present invention, a DNA construct is provided comprising a plant operable promoter operably linked to a nucleic acid sequence encoding a sensor protein, said protein comprising a secretory sequence for directing the protein to the extracellular space of a plant cell and a binding region specific for a target substance of interest, wherein said protein undergoes a conformational change when the target substance is bound, wherein the target substance is a nerve gas, a heavy metal, a poison, a pollutant, a toxin, an herbicide, a polycyclic aromatic hydrocarbon, a benzene, a toluene, a xylene, a halogenated (chloro, fluoro, and chlorofluoro) hydrocarbon, a steroid or other hormone, an explosive, or a degradation product of one of the foregoing compounds, wherein the encoded sensor protein specifically binds trinitrotoluene, and wherein the DNA construct comprises the sequence of SEQ ID NO:8.

In one aspect of the present invention, a DNA construct is provided comprising a plant operable promoter operably linked to a nucleic acid sequence encoding a protein which comprises the following domains: a plasma membrane targeting signal sequence, an extracellular domain for binding a sensor protein, a transmembrane domain and a histidine kinase domain for phosphorylating a protein with nuclear shuttling or transcriptional activating functions, wherein the histidine kinase is activated when a sensor protein binds to the extracellular domain.

In another aspect of the present invention, a DNA construct is provided comprising a plant operable promoter operably linked to a nucleic acid sequence encoding a protein which comprises the following domains: a plasma membrane targeting signal sequence, an extracellular domain for binding a sensor protein, a transmembrane domain and a histidine kinase domain for phosphorylating a protein with nuclear shuttling or transcriptional activating functions, wherein the histidine kinase is activated when a sensor protein binds to the extracellular domain, and wherein the extracellular domain, the transmembrane domain and the histidine kinase domain are derived from one or more bacterial genes and the membrane targeting signal sequence is derived from a plant gene.

In another aspect of the present invention, a DNA construct is provided comprising a plant operable promoter operably linked to a nucleic acid sequence encoding a sensor protein, said protein comprising a secretory sequence for directing the protein to the extracellular space of a plant cell and a binding region specific for a target substance of interest, wherein said protein undergoes a conformational change when the target substance is bound, and wherein the secretory sequence is from PEX (Pollen Extension-like protein).

In yet another aspect of the present invention, a DNA construct is provided comprising a plant operable promoter operably linked to a nucleic acid sequence encoding a protein which comprises the following domains: a plasma membrane targeting signal sequence, an extracellular domain for binding a sensor protein, a transmembrane domain and a histidine kinase domain for phosphorylating a protein with nuclear shuttling or transcriptional activating functions, wherein the histidine kinase is activated when a sensor protein binds to the extracellular domain, wherein the extracellular domain, the transmembrane domain and the histidine kinase domain are derived from one or more bacterial genes and the membrane targeting signal sequence is derived from a plant gene, and wherein the membrane targeting signal sequence is from FLS2.

In another aspect of the present invention, a DNA construct is provided comprising a plant operable promoter operably linked to a nucleic acid sequence encoding a protein which comprises the following domains: a plasma membrane targeting signal sequence, an extracellular domain for binding a sensor protein, a transmembrane domain and a histidine kinase domain for phosphorylating a protein with nuclear shuttling or transcriptional activating functions, wherein the histidine kinase is activated when a sensor protein binds to the extracellular domain, and wherein said histidine kinase domain comprises segments derived from a bacterium and a plant.

In a further aspect of the present invention, a DNA construct is provided comprising a plant operable promoter operably linked to a nucleic acid sequence encoding a protein which comprises the following domains: a plasma membrane targeting signal sequence, an extracellular domain for binding a sensor protein, a transmembrane domain and a histidine kinase domain for phosphorylating a protein with nuclear shuttling or transcriptional activating functions, wherein the histidine kinase is activated when a sensor protein binds to the extracellular domain, wherein said histidine kinase domain comprises segments derived from a bacterium and a plant, and wherein said histidine kinase domain comprises segments from a bacterial histidine kinase and a plant AHK4 (*Arabidopsis* histidine kinase) protein.

In another aspect of the present invention, a DNA construct is provided comprising a plant operable promoter operably linked to a nucleic acid sequence encoding a protein which comprises the following domains: a plasma membrane targeting signal sequence, an extracellular domain for binding a sensor protein, a transmembrane domain and a histidine kinase domain for phosphorylating a protein with nuclear shuttling or transcriptional activating functions, wherein the histidine kinase is activated when a sensor protein binds to the extracellular domain, wherein the extracellular domain, the transmembrane domain and the histidine kinase domain are derived from one or more bacterial genes and the membrane targeting signal sequence is derived from a plant gene, and wherein the sequence encoding the histidine kinase is that of SEQ ID NO:9.

In one aspect of the present invention, a DNA construct is provided comprising a plant operable promoter operably linked to a nucleic acid sequence encoding a detectable marker or a response gene, wherein the promoter is responsive to an internal signal caused by an external target substance of interest, and wherein said detectable marker is expressed when an external target substance of interest is bound to a sensor protein.

In another aspect of the present invention, a DNA construct is provided comprising a plant operable promoter operably linked to a nucleic acid sequence encoding a detectable marker or a response gene, wherein the promoter is responsive to an internal signal caused by an external target substance of interest, and wherein said detectable marker is expressed when an external target substance of interest is bound to a sensor protein, and wherein the detectable marker is a chlorophyll degradation enzyme or a functional fragment thereof.

In a further aspect of the present invention, a DNA construct is provided comprising a plant operable promoter operably linked to a nucleic acid sequence encoding a detectable marker or a response gene, wherein the promoter is responsive to an internal signal caused by an external target substance of interest, and wherein said detectable marker is expressed when an external target substance of interest is bound to a sensor protein, wherein the detectable marker is a chlorophyll degradation enzyme or a functional fragment thereof, and wherein the chlorophyll degradation enzyme is selected from the group consisting of red chlorophyll catabolite reductase (RCCR), pheophorbide a oxygenase (PaO), or chlorophyllase.

In yet another aspect of the present invention, a DNA construct is provided comprising a plant operable promoter operably linked to a nucleic acid sequence encoding a detectable marker or a response gene, wherein the promoter is responsive to an internal signal caused by an external target substance of interest, and wherein said detectable marker is expressed when an external target substance of interest is bound to a sensor protein, wherein the detectable marker is a chlorophyll degradation enzyme or a functional fragment thereof, further comprising a plant operable promoter responsive to an external target substance of interest operably linked to a nucleic acid sequence encoding an interfering RNA molecule specific for a chlorophyll biosynthesis coding sequence.

In another aspect of the present invention, a DNA construct is provided comprising a plant operable promoter operably linked to a nucleic acid sequence encoding a detectable marker or a response gene, wherein the promoter is responsive to an internal signal caused by an external target substance of interest, and wherein said detectable marker is expressed when an external target substance of interest is bound to a sensor protein, wherein the detectable marker is a chlorophyll degradation enzyme or a functional fragment thereof, further comprising a plant operable promoter responsive to an external target substance of interest operably linked to a nucleic acid sequence encoding an interfering RNA molecule specific for a chlorophyll biosynthetic enzyme coding sequence, and wherein the chlorophyll biosynthesis coding sequence encodes chlorophyll synthetase, protochlorophyllide oxidoreductase (POR) or genome uncoupling 4 (GUN4), a gene regulating cholorphyll biosynthesis.

In a further aspect of the present invention, a DNA construct is provided comprising a plant operable promoter operably linked to a nucleic acid sequence encoding a detectable marker or a response gene, wherein the promoter is responsive to an internal signal caused by an external target substance of interest, and wherein said detectable marker is expressed when an external target substance of interest is bound to a sensor protein, wherein the detectable marker is a chlorophyll degradation enzyme or a functional fragment thereof, and wherein the plant operable promoter comprises a PhoB binding sequence.

In another aspect of the present invention, a DNA construct is provided comprising a plant operable promoter operably linked to a nucleic acid sequence encoding a detectable marker or a response gene, wherein the promoter is responsive to an internal signal caused by an external target substance of interest, and wherein said detectable marker is expressed when an external target substance of interest is bound to a sensor protein, wherein the detectable marker is a chlorophyll degradation enzyme or a functional fragment thereof, wherein the plant operable promoter comprises a PhoB binding sequence, and wherein the plant operable promoter is set forth in SEQ ID NO:1.

In yet another aspect, a DNA construct is provided comprising a plant operable promoter operably linked to a nucleic acid sequence encoding a plant operable transcriptional activator, wherein the transcriptional activator is activated when phosphorylated by a histidine kinase.

In another aspect, a DNA construct is provided comprising a plant operable promoter operably linked to a nucleic acid sequence encoding a plant operable transcriptional activator, wherein the transcriptional activator is activated when phosphorylated by a histidine kinase, and wherein the plant operable transcriptional activator is that of SEQ ID NO:4.

In a further aspect, a DNA construct is provided comprising a plant operable promoter operably linked to a nucleic acid sequence encoding a plant operable transcriptional activator, wherein the transcriptional activator is activated when phosphorylated by a histidine kinase, and wherein the plant operable transcriptional activator is that of SEQ ID NO:11.

In another aspect, a transgenic plant is provided comprising a) a first DNA construct comprising a plant operable promoter operably linked to a nucleic acid sequence encoding a sensor protein, said protein comprising a secretory sequence for directing the protein to the extracellular space of a plant cell and a binding region specific for a target substance of interest, wherein said protein undergoes a conformational change when the target substance is bound, and b) a second DNA construct comprising a plant operable promoter operably linked to a nucleic acid sequence encoding a protein which comprises the following domains: a plasma membrane targeting signal sequence, an extracellular domain for binding a sensor protein, a transmembrane domain and a histidine kinase domain for phosphorylating a protein with nuclear shuttling or transcriptional activating functions, wherein the histidine kinase is activated when a sensor protein binds to the extracellular domain, and c) a third DNA construct comprising a plant operable promoter operably linked to a nucleic acid sequence encoding a detectable marker or a response gene, wherein the promoter is responsive to the transcriptional activator protein, and wherein the detectable marker is expressed when an external target substance of interest is bound to a sensor protein.

In yet a further aspect, the target substance of the DNA construct of the transgenic plant is a nerve gas, a heavy metal, a poison, a pollutant, a toxin, an herbicide, a polycyclic aromatic hydrocarbon, a benzene, a toluene, a xylene, a halogenated (chloro, fluoro, and chlorofluoro) hydrocarbon, a steroid or other hormone, an explosive, or a degradation product of one of the foregoing compounds.

In another aspect, the encoded sensor protein of the DNA construct of the transgenic plant specifically binds trinitrotoluene.

In a further aspect, the DNA construct of the transgenic plant comprises the sequence of SEQ ID NO:8.

In another aspect, the extracellular domain, the transmembrane domain and the histidine kinase domain of the DNA construct of the transgenic plant are derived from one or more bacterial genes, and the membrane targeting signal sequence is derived from a plant gene.

In another aspect, the secretory sequence of the sensor protein of the DNA construct of the transgenic plant is from PEX.

In yet another aspect, the membrane targeting signal sequence of the DNA construct of the transgenic plant is from FLS2.

In another aspect, the histidine kinase domain of the DNA construct of the transgenic plant comprises segments derived from a non-plant organism.

In another aspect, the histidine kinase domain of the DNA construct of the transgenic plant comprises segments derived from a non-plant organism and a plant.

In a further aspect, the histidine kinase domain of the DNA construct of the transgenic plant comprises segments derived from a non-plant organism and a plant.

In another aspect, the sequence encoding the histidine kinase of the DNA construct of the transgenic plant is that of SEQ ID NO:2, SEQ ID NO:3, SEQ ID NO:10 or SEQ ID NO:12.

In yet another aspect, the detectable marker of the DNA construct of the transgenic plant is a chlorophyll degradation enzyme or a functional fragment thereof.

In a further aspect, a transgenic plant is provided with a detectable marker wherein the plant loses detectable green color when the detectable marker is expressed.

In another aspect, the chlorophyll degradation enzyme of the DNA construct of the transgenic plant is selected from the group consisting of red chlorophyll catabolite reductase (RCCR), pheophorbide a oxygenase (PaO), or chlorophyllase.

In a further aspect, a transgenic plant is provided comprising a plant operable promoter responsive to a transcription activator protein operably linked to a nucleic acid sequence encoding an interfering RNA molecule specific for a chlorophyll biosynthesis coding sequence.

In yet another aspect, the chlorophyll biosynthesis coding sequence of the DNA construct of the transgenic plant encodes chlorophyll synthetase, protochlorophyllide oxidoreductase (POR) or GUN4, a gene regulating cholorphyll biosynthesis.

In another aspect, the plant operable promoter of the DNA construct of the transgenic plant comprises a PhoB binding sequence.

In a further aspect, the plant operable promoter of the DNA construct of the transgenic plant is set forth in SEQ ID NO:1.

In yet another aspect, a transgenic plant is provided which further comprises a fourth DNA construct comprising a nucleic acid encoding a chlorophyll degradation enzyme or a functional fragment thereof operably linked to a plant operable promoter responsive to the transcription activator protein, and wherein said promoter is not in nature associated with said sequence encoding a chlorophyll degradation enzyme.

In another aspect, a transgenic plant is provided which further comprises a fourth DNA construct comprising a plant operable promoter operably linked to a nucleic acid sequence encoding a plant operable transcriptional activator, wherein the transcriptional activator is activated when phosphorylated by a histidine kinase.

In a further aspect, the detectable marker of the transgenic plant is a functional RNA.

In yet another aspect, the functional RNA of the transgenic plant is an interfering RNA molecule.

In another aspect, the functional RNA of the transgenic plant inhibits expression of a chlorophyll biosynthesis coding sequence.

In a further aspect, the chlorophyll biosynthesis coding sequence of the transgenic plant encodes chlorophyll synthetase, protochlorophyllide oxidoreductase (POR) or GUN4, a gene regulating chlorophyll biosynthesis.

In yet another aspect, the detectable marker of the transgenic plant is a chlorophyll degradation enzyme.

In another aspect, the chlorophyll degradation enzyme of the transgenic plant is red chlorophyll catabolite reductase (RCCR), pheophorbide a oxygenase (PaO), or chlorophyllase.

In a further aspect, the detectable marker of the transgenic plant is a β-glucuronidase, a β-galactosidase or a green or yellow fluorescent protein.

In yet another aspect, the transcription activator protein of the DNA construct of the transgenic plant comprises a response regulator domain.

In another aspect, the response regulator domain of the DNA construct of the transgenic plant is derived from PhoB.

In a further aspect, the transcription activator protein of the DNA construct of the transgenic plant is a PhoB:VP64 translational fusion protein.

In yet another aspect, the sequence encoding the PhoB:VP64 protein of the DNA construct of the transgenic plant is given in SEQ ID NO:4, SEQ ID NO:5 SEQ ID NO:6 or SEQ ID NO:11.

In another aspect, the detectable marker of the transgenic plant is a functional RNA which inhibits expression of a chlorophyll biosynthetic enzyme coding sequence.

In a further aspect, a transgenic plant is provided, wherein the plant loses green color due to inhibition of chlorophyll biosynthesis and enhanced breakdown of chlorophyll upon induction of a gene encoding a chlorophyll degradation enzyme.

In yet another aspect, a transgenic plant is provided, wherein the plant loses green color due to inhibition of chlorophyll biosynthesis and enhanced breakdown of chlorophyll upon induction of a gene encoding a chlorophyll degradation enzyme and wherein the enhanced breakdown of chlorophyll is achieved by expressing at least one enzyme selected from the group consisting of red chlorophyll catabolite reductase (RCCR), pheide a oxygenase (PaO), and chlorophyllase.

In another aspect, a transgenic plant is provided, wherein the plant loses green color due to inhibition of chlorophyll biosynthesis and enhanced breakdown of chlorophyll upon induction of a gene encoding a chlorophyll degradation enzyme and wherein the inhibition of chlorophyll biosynthesis is achieved by inhibiting expression of at least one enzyme selected from the group consisting of protochlorophyllide oxidoreductase (POR), chlorophyll synthetase and GUN4.

In a further aspect, the inhibition of POR in the transgenic plant is achieved by producing an interfering RNA molecule that contains a sequence derived from the coding sequence of POR.

In yet another aspect, a transgenic plant is provided, wherein the plant loses green color by inhibiting POR and stimulating RCCR and chlorophyllase.

In another aspect, a method is provided for detecting an external substance of interest, said method comprising the step of exposing a transgenic plant to an external substance of interest and detecting a change resulting from expression of a detectable marker.

In a further aspect, a method is provided for detecting an external substance of interest, said method comprising the step of exposing a transgenic plant to an external substance of interest and detecting a change resulting from expression of a detectable marker, and wherein the detectable marker is a functional RNA.

In yet another aspect, a method is provided for detecting an external substance of interest, said method comprising the step of exposing a transgenic plant to an external substance of interest and detecting a change resulting from expression of a detectable marker, wherein the detectable marker is a functional RNA, and wherein the functional RNA is an interfering RNA molecule.

In another aspect, a method is provided for detecting an external substance of interest, said method comprising the step of exposing a transgenic plant to an external substance of interest and detecting a change resulting from expression of a detectable marker, wherein the detectable marker is a functional RNA, and wherein the functional RNA inhibits expression of a chlorophyll biosynthesis coding sequence.

In a further aspect, a method is provided for detecting an external substance of interest, said method comprising the step of exposing a transgenic plant to an external substance of interest and detecting a change resulting from expression of a detectable marker, wherein the detectable marker is a functional RNA, and wherein the functional RNA inhibits expression of a chlorophyll biosynthesis coding sequence, and wherein the chlorophyll biosynthesis enzyme is a chlorophyll synthetase, protochlorophyllide oxidoreductase (POR) or a GUN4, a gene regulating chlorophyll biosynthesis.

In yet another aspect, a method is provided for detecting an external substance of interest, said method comprising the step of exposing a transgenic plant to an external substance of interest and detecting a change resulting from expression of a detectable marker, and wherein the detectable marker is a chlorophyll degradation enzyme.

In another aspect, a method is provided for detecting an external substance of interest, said method comprising the step of exposing a transgenic plant to an external substance of interest and detecting a change resulting from expression of a detectable marker, and wherein the detectable marker is a chlorophyll degradation enzyme, and wherein the chlorophyll degradation enzyme is red chlorophyll catabolite reductase (RCCR), pheophorbide a oxygenase (PaO), or chlorophyllase.

In a further aspect, a method is provided for detecting an external substance of interest, said method comprising the step of exposing a transgenic plant to an external substance of interest and detecting a change resulting from expression of a detectable marker, and wherein the detectable marker is a β-glucuronidase, a β-galactosidase or a green or yellow fluorescent protein.

In yet another aspect, a method is provided for detecting an external substance of interest, said method comprising the step of exposing a transgenic plant to an external substance of interest and detecting a change resulting from expression of a detectable marker, and wherein said transgenic plant comprises a) a first DNA construct comprising a plant operable promoter operably linked to a nucleic acid sequence encoding a sensor protein, said protein comprising a secretory sequence for directing the protein to the extracellular space of a plant cell and a binding region specific for a target substance of interest, wherein said protein undergoes a conformational change when the target substance is bound, and b) a second DNA construct comprising a plant operable promoter operably linked to a nucleic acid sequence encoding a protein which comprises the following domains: a plasma membrane targeting signal sequence, an extracellular domain for binding a sensor protein, a transmembrane domain and a histidine kinase domain for phosphorylating a protein with nuclear shuttling or transcriptional activating functions, wherein the histidine kinase is activated when a sensor protein binds to the extracellular domain, and c) a third DNA construct comprising a plant operable promoter operably linked to a nucleic acid sequence encoding a detectable marker or a response gene, wherein the promoter is responsive to the transcriptional activator protein, and wherein the detectable marker is expressed when an external target substance of interest is bound to a sensor protein and wherein said transcription activator protein is a PhoB protein or is derived from a PhoB protein.

In another aspect, a method is provided for detecting an external substance of interest, said method comprising the step of exposing a transgenic plant to an external substance of interest and detecting a change resulting from expression of a detectable marker, and wherein said transgenic plant comprises a) a first DNA construct comprising a plant operable promoter operably linked to a nucleic acid sequence encoding a sensor protein, said protein comprising a secretory sequence for directing the protein to the extracellular space of a plant cell and a binding region specific for a target substance of interest, wherein said protein undergoes a conformational change when the target substance is bound, and b) a second DNA construct comprising a plant operable promoter operably linked to a nucleic acid sequence encoding a protein which comprises the following domains: a plasma membrane targeting signal sequence, an extracellular domain for binding a sensor protein, a transmembrane domain and a histidine kinase domain for phosphorylating a protein with nuclear shuttling or transcriptional activating functions, wherein the histidine kinase is activated when a sensor protein binds to the extracellular domain, and c) a third DNA construct comprising a plant operable promoter operably linked to a nucleic acid sequence encoding a detectable marker or a response gene, wherein the promoter is responsive to the transcriptional activator protein, and wherein the detectable marker is expressed when an external target substance of interest is bound to a sensor protein and wherein said transcription activator protein is a PhoB:VP64 translational fusion protein.

In a further aspect, a method is provided for detecting an external substance of interest, said method comprising the step of exposing a transgenic plant to an external substance of interest and detecting a change resulting from expression of a detectable marker, and wherein said transgenic plant comprises a) a first DNA construct comprising a plant operable promoter operably linked to a nucleic acid sequence encoding a sensor protein, said protein comprising a secretory sequence for directing the protein to the extracellular space of a plant cell and a binding region specific for a target substance of interest, wherein said protein undergoes a conformational change when the target substance is bound, and b) a second DNA construct comprising a plant operable promoter operably linked to a nucleic acid sequence encoding a protein which comprises the following domains: a plasma membrane targeting signal sequence, an extracellular domain for binding a sensor protein, a transmembrane domain and a histidine kinase domain for phosphorylating a protein with nuclear shuttling or transcriptional activating functions, wherein the histidine kinase is activated when a sensor protein binds to the extracellular domain, and c) a third DNA construct comprising a plant operable promoter operably linked to a nucleic acid sequence encoding a detectable marker or a response gene, wherein the promoter is responsive to the transcriptional activator protein, and wherein the detectable marker is expressed when an external target substance of interest is bound to a sensor protein and, wherein said sequence encoding the PhoB:VP64 protein is given in SEQ ID NO:4 or SEQ ID NO:5.

In yet another aspect, a method is provided for detecting an external substance of interest, said method comprising the step of exposing a transgenic plant to an external substance of interest and detecting a change resulting from expression of a detectable marker, and wherein said transgenic plant comprises a) a first DNA construct comprising a plant operable promoter operably linked to a nucleic acid sequence encoding a sensor protein, said protein comprising a secretory sequence for directing the protein to the extracellular space of a plant cell and a binding region specific for a target substance of interest, wherein said protein undergoes a conformational change when the target substance is bound, and b) a second DNA construct comprising a plant operable promoter operably linked to a nucleic acid sequence encoding a protein which comprises the following domains: a plasma membrane targeting signal sequence, an extracellular domain for binding a sensor protein, a transmembrane domain and a histidine kinase domain for phosphorylating a protein with nuclear shuttling or transcriptional activating functions, wherein the histidine kinase is activated when a sensor protein binds to the extracellular domain, and c) a third DNA construct comprising a plant operable promoter operably linked to a nucleic acid sequence encoding a detectable marker or a response gene, wherein the promoter is responsive to the transcriptional activator protein, and wherein the detectable marker is expressed when an external target substance of interest is bound to a sensor protein and wherein said change is degreening of the transgenic plant.

In another aspect, the degreening of the transgenic plant is detected visually or by detecting properties selected from the group consisting of chlorophyll fluorescence, photosynthetic properties and properties related to reactive oxygen species and their damage.

In yet another aspect, the degreening of the transgenic plant is detected by imaging selected from the group consisting of hyper-spectral imaging, infra-red imaging, near-infra-red imaging and multi-spectral imaging In a further aspect, the transgenic plant regreens after removal of the external substance of interest.

In addition to the exemplary aspects and embodiments described above, further aspects and embodiments will become apparent by reference to the drawings and by study of the following descriptions.

DESCRIPTION OF THE DRAWINGS

Exemplary embodiments are illustrated in referenced figures of the drawings. It is intended that the embodiments and figures disclosed herein are to be considered illustrative rather than limiting.

FIGS. 1A-1F show the overview of the detection process and various protein components used in the sensing (or input) circuit and how they are linked to a specific output. FIG. 1A: SS-TNT is an example of a computer designed receptor (also referred to as sensor protein) based on bacterial periplasmic binding proteins. The protein leader for the bacteria is removed and replaced by a plant leader designated "SS" (secretory sequence), to target the sensor protein to the extracellular or apoplastic space. Any sensor protein, including but not limited to, trinitrotoluene (TNT), Methyl tert-butyl ether (MTBE), nerve gas, cyclotrimethylenetrinitramine (RDX) and those to be designed can be used. FIG. 1B shows a schematic of the ligand and computer designed receptor (sensor proteins) (note that there are many receptors and that only one is shown). FIG. 1C shows that the sensor protein binds TNT or the ligand (defined with computational design) with very high affinity and specificity. FIG. 1D shows that the sensor protein with the ligand (TNT) develops high affinity for the extracellular domain of the histidine kinase (HK, Trg) and activates the histidine kinase domain. The histidine kinase is activated and high energy phosphate is transferred to another protein. In this figure, the shuttling protein or transcription activator protein is PhoB:VP64. FIG. 1E shows that PhoB:VP64 shuttles to the nucleus, binds the PlantPho promoter and activates transcription of a linked gene or genes, in this case the degreening circuit that produced white plants (or a lighter green color). FIG. 1F shows a schematic of the degreening circuit.

FIG. 2A shows three histidine kinases (HKs). In the first panel, after the receptors (sensor proteins) bind their ligand they develop a high affinity for Trg. Hybrid HKs containing Trg (light grey dashes) were formed and shown to function in both bacteria and in plants. For plant expression, a protein leader, such as the FLS (dashed line) exemplified is used. This leader is cleaved during processing. Trg causes a conformational change activating the intracellular kinase. The high energy phosphate signal is then transmitted by (left to right) the hybrid proteins AHK4, PhoR, or EnvZ. FIG. 2B shows the transmission protein for each hybrid HK shown in FIG. 2A. FLS:Trg:EnvZ:AHK4 transmits its phosphate signal to histidine phosphotransferases (AHPs) whereas both FLS:Trg:PhoR and FIs:Trg:EnvZ transmit their phosphate signal to PhoB:VP64. FIG. 2C shows that both proteins that receive a phosphate signal from the HKs translocate to the nucleus and activate expression of linked genes. The left panel shows, AHP translocates to the nucleus and activates expression of promoters such as ARR5 or ARR7 (Type A ARR promoters). The right panel shows PhoB:VP64 translocates to the nucleus and activates expression of a synthetic promoter PlantPho promoter.

FIG. 3A shows the bacterial response regulator (RR) PhoB translocates to the plant nucleus in response to an external cytokinin signal. FIG. 3A panels A-B show transient assay of PhoB:GFP fusion protein in onion epidermal cells. Cells treated with cytokinin (B) had stronger nuclear PhoB:GFP accumulation than control (A) cells. FIG. 3A panels C-P show signal-dependent shuttling of PhoB:GFP to the nucleus in transgenic *Arabidopsis* plants. Localization of PhoB:GFP in roots (C-H), in leaves (I-J, M-N), and the crown (K-L, O-P), a stem-like region. Prior to cytokinin treatment (C, I, K), fluorescence from PhoB:GFP is diffuse and throughout the cells. After treatment with exogenous cytokinin (D-H, J, L-P), the same tissue shows distinct accumulation of PhoB:GFP in compartments that also stain with DAPI (F, H, N, P), indicating that they are nuclei. FIG. 3A panels Q-R show confocal microscopy of PhoB:GFP roots showing that the protein enters the nucleus. Insets correspond to close-up views. −CK, plant tissues prior to cytokinin treatment; +CK same plant tissue after cytokinin treatment. DAPI, same tissues treated with DAPI to stain DNA. Arrowheads indicate nuclei. Scale bars=50 μm. FIG. 3B shows the bacterial response regulator (RR) OmpR translocates to the plant nucleus in response to an external cytokinin signal. FIG. 3B panels A-D show signal-dependent nuclear localization of OmpR:GFP in roots, panels E-J leaves, and panels K-N the crown, a stem-like region. Panels to the right correspond to close-up views of cells treated with cytokinin (+CK), or cells treated with cytokinin and DAPI for visualization of nuclei (DAPI). FIG. 3B panels O-P show confocal microscopy of OmpR:GFP-expressing roots showing that the protein enters the nucleus in response to the cytokinin signal. Insets correspond to close-up views of cells. −CK, tissues incubated in the absence of cytokinin +CK, tissues incubated in the presence of cytokinin; DAPI, indicate incubation with DAPI to stain DNA. Arrows point to cell nuclei. Scale bars=50 μm. FIG. 3C shows nuclear localization of PhoB:GFP:GUS fusion protein in response to the external cytokinin signal; panels B-D shows that some type of transport mechanism must be involved in the nuclear shuttling. Nuclear identity is confirmed by DAPI staining panel E. Arrowheads point to cell nuclei. Scale bars=50 μm. FIG. 3D shows mutation of the phospho-accepting Asp residue in PhoB and OmpR disrupts shuttling. Upper panels, PhoB$^{D53A}$: GFP or, lower panels OmpR$^{D55A}$:GFP, in transgenic plants. Some PhoB$^{D53A}$:GFP localizes to the base of root cortical cells (arrows); but nuclear shuttling is not seen in non-vascular cells. Some weaker nuclear localization is seen in vascular cells (arrowheads). Mutation of the conserved Asp55 eliminated shuttling of OmpR$^{D55A}$:GFP. Arrowheads point to nuclei. −CK, plants prior to cytokinin treatment; +CK same plant tissue after cytokinin treatment. DAPI, same tissues treated with DAPI to stain DNA. Scale bars=50 μm. FIG. 3E shows mutation of the phospho-accepting Asp residue in PhoB disrupts signaling from the TNT receptor. FIG. 3E panel A shows independent transgenic plants containing the PhoB$^{D53A}$:VP64 mutagenized protein linked to the TNT sensing system were tested for induction of GUS activity with 10 μM TNT. No significant induction was observed (levels were consistently less than 4, levels seen in controls). FIG. 3E panel B shows a homozygous transgenic line containing the wild-type PhoB:VP64 linked to the TNT sensing system consistently shows TNT induction.

FIG. 4A shows FLS:Trg:EnvZ:AHK4 signals to and activates plant AHPs, activating plant AHPs. Phosphorylated AHPs shuttle to the cell nucleus, where they transfer their phosphate group to a Type-B ARR. Activated Type-B ARR then binds to and activates the ARR5 promoter. GUS activity is expressed as nmoles 4-MU mg$^{-1}$ protein h$^{-1}$. To, indicates primary transformants; T1, indicates the next generation of transgenic plants. To P-value=0.0002; T1 P-value=0.0102. FIG. 4B shows FLS: Trg:PhoR signals to PhoB:VP64, which translocates to the nucleus where it binds to and activates the PlantPho promoter. FIG. 4C shows FLS:Trg:EnvZ (Trz) signals to PhoB:VP64, which translocates to the nucleus where it binds to and activates the PlantPho promoter. GUS activity is expressed as nmoles 4-MU mg$^{-1}$ protein h$^{-1}$. FIG. 4D shows a variation of the VP64 activation domain fused to PhoB (PhoB:VP16) also activates the PlantPho promoter in response to an input (cytokinin in this case). GUS activity is expressed as nmoles 4-MU mg$^{-1}$ protein h$^{-1}$. CK, cytokinin.

FIG. 5A upper panels show the appearance of two plants from each degreening circuit (number 1-5) at 0, 24 and 48 hours after induction. The middle panel shows a schematic for each degreening circuit. Represented is a chlorophyll molecule. The "stop" signs indicate genes that were inhibited by an interfering RNA molecule (diRNA) construct; lightning bolts represent genes that were over-expressed. The bottom panel shows the appearance of plants that had been induced to fully degreen and regreen for 3 days. FIG. 5B shows the results of semi-quantitative RT-PCR analysis of the degreening circuit transcripts at 0, 24 and 48 hours after induction and regreening for 3 days. CYC, cyclophilins, was used as a sample loading control. In the control samples, −ind indicates samples without induction and +ind indicates samples with induction. FIG. 5C shows remote monitoring of the degreening circuit by effects on chlorophyll fluorescence. Time course changes of total chlorophyll and maximum chlorophyll fluorescence in dark-adapted plants (Fm) (upper panel), operating efficiency of PSII (φPSII)(middle panel), and maximum quantum efficiency of PSII (Fv/Fm)(lower panel) in transgenic plants containing degreening circuit #1 and wild-type control (Columbia). Solid lines with filled squares, control plants; dashed lines with open squares, induced plants; dotted lines with open triangles, total chlorophyll levels of induced plants. F.W.: fresh weight. Plants were incubated in the presence (induced) or absence (control) of the inducer. FIG. 5D shows induction of the degreening results in accumulation of Reactive Oxygen Species (ROS).

Auto-fluorescence from chlorophyll can be seen in both panels whereas ROS is only seen in the degreening panel. FIG. 5E parts a-c, show rapid loss of chlorophyll upon induction of the degreening circuit requires light both in whole plants and in detached leaves. FIG. 5E part a shows the effect of light on degreening of whole plants. Fourteen-day old plants containing degreening circuit #3 were induced to degreen and placed in complete darkness. After 24, 48 or 72 hours, samples were removed from the dark, photographed, and transferred to normal light conditions (approx. 100 µE·m−2·s−1; 16 h light/8 h dark). Plants were re-photographed after 24, 48 or 72 hours in light. Dark panels: plants placed in complete darkness. Arrows indicate samples moved to light. FIG. 5E part b shows degreening of detached leaves in the light from plants containing different circuits. Top panels, leaves at 0 hours of induction; lower panels, leaves at 48 hours of induction. "C" indicates the Columbia control plants. 1, 2, and 3, indicate the specific degreening circuit. FIG. 5E part c shows the effect of light on degreening of detached leaves. Leaves were excised from 14-day old plants containing circuit #2, and the degreening circuit was induced as described above. Left panels show leaves incubated in the light; right dark panels show leaves incubated in darkness; right lower panels indicate leaves incubated in darkness after they were transferred to light. Numbers next to panels indicate time of incubation, in hours. FIG. 5F shows the response of senescence-related genes during degreening. A list of 827 genes that are strongly and reproducibly induced during developmental leaf senescence (Buchanan-Wollaston et al., 2005) is used here as a basis for comparison with whole-genome microarray analysis of synthetic degreening (24 h post-induction). The dashed line in each plot corresponds to a degreening expression ratio of 1.5 (0.58 $\log_2$). Points above this line represent genes that are up-regulated at least 1.5 fold in both degreening and senescence. Points below the dashed line are strongly induced during senescence, but are not strongly induced during degreening. Error bars show the standard error of the mean expression ratio (degreening/uninduced). Genes are classified in categories adapted from Buchanan-Wollaston et al., 2005. 89% of the previously described senescence-induced genes were detected in our microarray analysis; the remainder had signals that were too weak or variable to be accurately described. Minor categories with fewer than five members were combined with the genes of unknown function in plot (t).

FIG. 6A shows induction of *Arabidopsis* degreening with 100 pM TNT. FIG. 6B shows induction of Tobacco degreening with 10 µM TNT. FIGS. 6C-D show time-course monitoring of chlorophyll fluorescence as a measure of degreening in *Arabidopsis* and Tobacco detached leaves induced to degreen. Chlorophyll measurements were obtained using a Fluorcam. One of the parameters derived from chlorophyll measurements is Fv/Fm, which is a measure of photosynthetic capability (specifically maximum quantum yield of PSII). A normal leaf would have an Fv/Fm ratio of 0.8. Note the decline over time in the Fv/Fm ratio as the leaves degreen, however the wild-type Columbia leaf stayed close to 0.8. FIG. 6C shows Fluorcam data for *Arabidopsis* T0 degreening. FIG. 6D shows Fluorcam data for Tobacco T0 degreening.

FIG. 9A shows setting the trigger circuitry to enable plants to respond to a single exposure to TNT. The degreening genes are under control of a modified CaMV35S promoter. This modified CaMV35S promoter contains the LexA DNA binding elements allowing Repressor 2 to bind and keep the degreening genes off. Expression of Repressor 2 protein (LexA DBD/EAR2) is driven by a modified constitutive promoter (Pnos, weakly constitutive), containing DNA elements for the GAL4 DNA binding domain. Plants functioning on the male side contain the normal sensing circuitry (TNT receptor, transmembrane HK, and PhoB:VP64), and two additional genes that both direct the expression of Repressor 1 (containing the GAL4 DBD and EAR1 repressor domain). One gene directing the expression of Repressor 1 is under the direction of the PlantPho promoter. The second gene directing the expression of Repressor 1 is under the direction of a weak constitutive promoter (Pnos) modified to contain LexA DNA elements. To set the "trigger switch", pollen obtained from homozygous plants with the gene circuitry indicated for the male plant is used to fertilize homozygous plants containing the gene circuitry indicated for the female plant. NLS, indicates nuclear localization sequence; nos, indicates 3' terminator sequence from the nopaline synthase gene; ON, indicates the gene is expressed; OFF, indicates the gene is not expressed. FIG. 9B shows that in the absence of the ligand (the explosive TNT) the receptors have no affinity for the transmembrane histidine kinase, and the response regulator protein (PhoB:VP64) is unphosphorylated, causing its receiver domain to repress the transactivation domain within this protein. The degreening genes are transcriptionally off because constitutive expression of Repressor 2 prevents expression of the CaMV35S: LexA promoter. FIG. 9C shows in response to TNT, the receptor specifically binds the explosive and develops a high affinity for the histidine kinase (Trg/PhoR). This causes a conformational change and activation of the kinase that then sends a high energy phospho-relay to PhoB:VP64. In the plants where the "trigger" genetic circuitry is set, phosphorylated PhoB:VP64 translocates to the nucleus, binds the PlantPho promoter, and activates expression of Repressor 1. Repressor 1 then binds to and represses the Pnos:GAL4 promoter. Repressing this promoter will turn OFF the Repressor 2 protein (LexA/EAR2). Turning OFF the LexA/EAR2 protein allows activation of two genes: first, the degreening circuit genes (under control of the CaMV 35S:LexA promoter); second, removing Repressor 2 also allows expression of Repressor 1 under control of the Pnos:LexA promoter. Since the Pnos:LexA promoter does not need the continuous activation from a phosphorylated PhoB:VP64, the detection system does not need continuous exposure to TNT. Therefore, expression of Pnos:LexA allows the readout (degreening) system to remain active even with a single exposure to an explosive.

DETAILED DESCRIPTION OF THE INVENTION

Figure 1A:
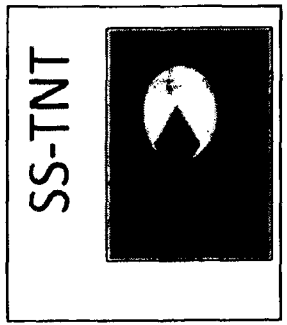
Figure 1B:
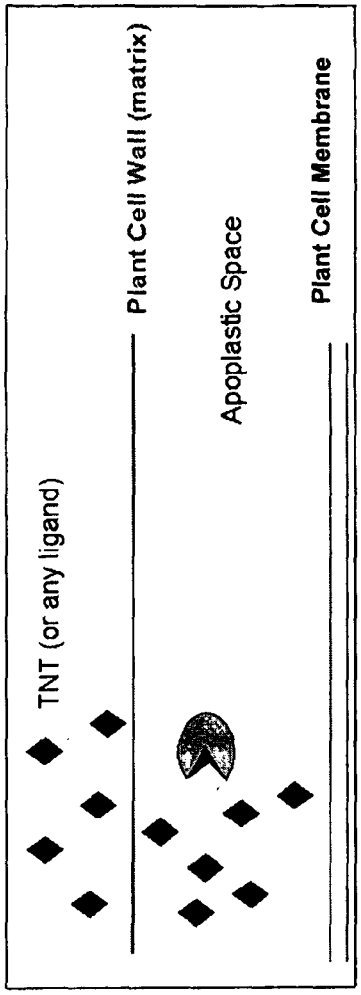
Figure 1C:
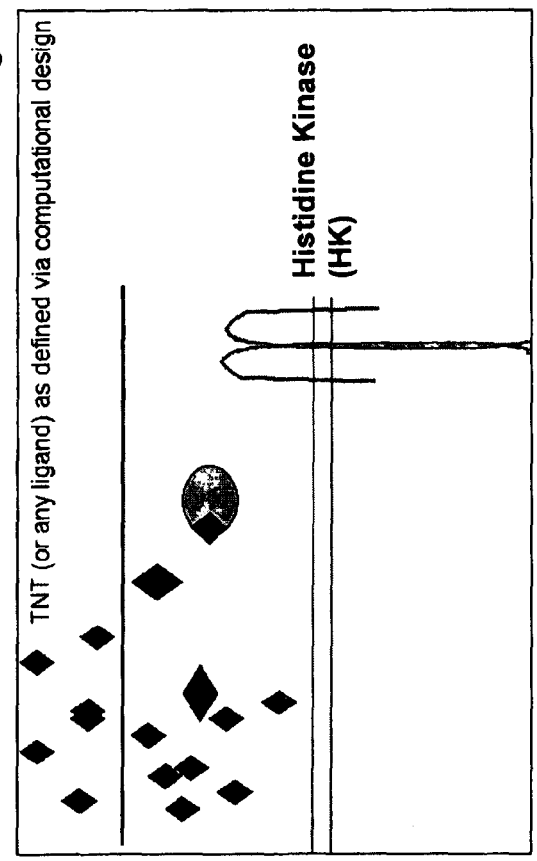
Figure 1E:
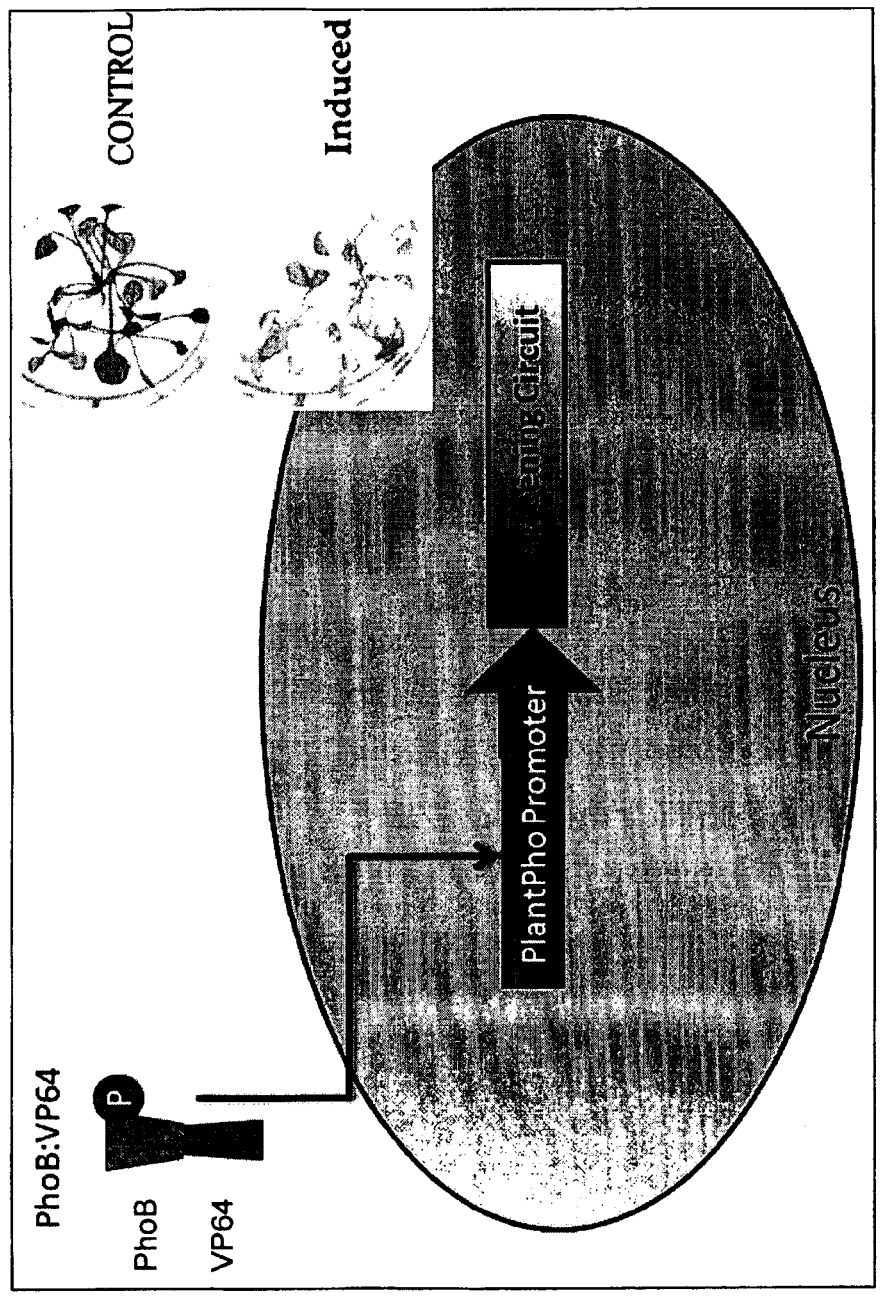

In general the terms and phrases used herein have their art-recognized meaning, which can be found by reference to standard texts, journal references and contexts known to those skilled in the art. The following definitions are provided to clarify their specific use in the context of the invention.

The term, "transgenic plant", is used herein to indicate a plant, or photosynthetic organism including algae, which has been genetically modified to contain exogenous or heterologous DNA to obtain a desired phenotype. Examples of the exogenous DNA molecules that have been transformed into the plants of the invention include those encoding segments of DNA encoding the sensor protein, the transmembrane protein, a shuttling and/or response protein, and a receptive promoter, collectively known as the response circuits and/or those encoding segments of chlorophyll biosynthetic and/or complete degradation enzymes and a promoter which is responsive to a signal.

The term, "plant" as used in the present invention, is intended to cover any plant, vascular or nonvascular, aquatic or terrestrial; algae, and organisms formally and informally recognized as algae now more properly known as cyanobacteria are included within this definition.

The term "non-plant organism" includes, but is not limited to Archea, bacteria, fungi including yeast and cyanobacteria and the like and other organisms containing two-component signaling systems.

The term "degreening", also referred to as a "loss of green color", is intended to indicate a loss of chlorophyll and photosynthetic pigments in the transgenic plants that is distinguishable from normal plants (non-transgenic plants). The degreening can be detected visibly, or with a variety of instruments that measure properties including but not limited to chlorophyll fluorescence, hyper-spectral imaging, infra-red and near-infra-red imaging, multi-spectral imaging, photosynthetic properties and properties related to reactive oxygen species and their damage. The measurement instruments can be hand-held, or instruments that function at a distance, the distance being from aircraft or satellites.

The term, "external signal", or "environmental signal", or "target substance of interest", is intended to mean a signal typically in the form of an analyte or ligand which triggers the signaling pathway in the transgenic plants of the invention and results in the degreening phenotype and/or change such as induction of gene expression of interest. In this sense, the signal can be any biological or chemical agent including environmental pollutants. The substance can be, for example, sugars, herbicides, a poison, a pollutant, a toxin, a nerve gas such as soman, heavy metals such as mercury, lead, arsenic, uranium, cadmium, selenium, polycyclic aromatic hydrocarbon, a benzene, a toluene, a xylene, or a halogenated (chloro, fluoro, and chlorofluoro) hydrocarbon, a steroid or other hormone. In addition, the target substance which binds to a specifically engineered input circuit via the extracellular receptor could be an explosive such as TNT (trinitrotoluene), RDX (cyclonite, hexahydro-1,3,5,-trinitro-1,3,5-triazine), HMX (octagen, octahydro-1,3,5,7-tetranitro-1,3,5,7-tetrazocine) or TATP (triacetone peroxide), or a degradation product of one of the foregoing compounds recognized by the input circuit via specific receptor site binding by the sensor protein. Any target substance for which a sensor protein can be computationally designed (Looger et al., 2003; Dwyer et al., 2004; Marvin and Helling a, 2001) can serve as an external signal in the context of the present invention.

The term "detectable marker" is a change brought about in the plant that is perceivable or capable of being sensed by humans, other organisms such as but not limited to dogs, and/or machines. The change can be visible or invisible to humans. The sensing can involve non-destructive (for example, multi-spectral imaging) or destructive methods (for example, analysis of protein, DNA, RNA or metabolic product).

The term "response regulator domain" is a protein or portion of a protein that contains conserved amino acids collectively functioning to perceive a phosphor-relay from an activated histidine kinase. The conserved domain may contain a phosphor-accepting Asp or His residue or it may contain other residues that can be made capable of accepting the activated phosphate.

The term "response gene" is a gene whose expression is linked to input from the sensor protein or proteins.

The term "sensor protein" is used interchangeably with "receptor".

The term "transmembrane protein" is used interchangeably with "histidine kinase".

The terms "expression construct" or "DNA construct" are used interchangeably herein and indicate a DNA construct comprising particular sequences necessary for transcription of an associated downstream sequence. An expression vector is a plasmid containing an expression construct. If appropriate and desired for the associated sequence, the term expression also encompasses translation (protein synthesis) of the transcribed RNA. The particular sequences contained in the expression vector include a promoter, enhancer, termination signal, transcriptional block (Padidam, M and Cao, Y, 2001) and the like. To prevent transcriptional interference from multiple transgenes, a transcriptional block is placed between appropriate genes on a plant transformation plasmid. A promoter is a DNA region which includes sequences sufficient to cause transcription of an associated (downstream) sequence. The promoter may be regulated, i.e., not constitutively acting to cause transcription of the associated sequence. If inducible, there are sequences present therein which mediate regulation of expression so that the associated sequence is transcribed only when an inducer molecule is present. In the present context, the inducer molecule is analogous to the signal transmitted by an input circuit.

The term "derived from" includes genes, nucleic acids, and proteins when they include fragments or elements assembled in such a way that they produce a functional unit. The fragments or elements can be assembled from multiple organisms provided that they retain evolutionarily conserved function. Elements or domains could be assembled from various organisms and/or synthesized partially or entirely, provided that they retain evolutionarily conserved function, elements or domains. In some cases the derivation could include changes so that the codons are optimized for expression in a particular organism.

The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine;

H, His, Histidine; I, Ile, Isoleucine; K, Lys, Lysine; L, Leu, Leucine; M, Met, Methionine; N, Asn, Asparagine; P, Pro, Proline; Q, Gin, Glutamine; R, Arg, Arginine; S, Ser, Serine; T, Thr, Threonine; V, Val, Valine; W, Trp, Tryptophan; Y, Tyr, Tyrosine.

A protein is considered an isolated protein if it is a protein isolated from a host cell in which it is recombinantly produced. It can be purified or it can simply be free of other proteins and biological materials with which it is associated in nature.

One DNA portion or sequence is downstream of a second DNA portion or sequence when it is located 3' of the second sequence. One DNA portion or sequence is upstream of a second DNA portion or sequence when it is located 5' of that sequence. Alternatively, the DNA sequences can be arranged in a functional polycistronic arrangement (Walker, J. M. and Vierstra, R. D., 2007). Polycistronic messenger RNAs (mRNAs) are those resulting from transcription of two or more open reading frames (ORFs) fused together as one single mRNA from one promoter. A plant operable polycistronic mRNA may be obtained by fusing a ubiquitin moiety between two ORFs.

One DNA molecule or sequence is heterologous to another if the two are not derived from the same ultimate natural source. The sequences may be natural sequences, or at least one sequence can be designed by man, as in the case of a multiple cloning site region or an entirely synthetic DNA sequence that encodes a gene or a fragment of a gene. The two sequences can be derived from two different species or one sequence can be produced by chemical synthesis provided that the nucleotide sequence of the synthesized portion was not derived from the same organism as the other sequence.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter effects the transcription or expression of the coding sequence. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Large amounts of polynucleotides may be produced by replication in a suitable host cell. Natural or synthetic DNA fragments coding for a protein of interest are incorporated into recombinant polynucleotide constructs, typically DNA constructs, capable of introduction into and replication in a prokaryotic or eukaryotic cell, such as *Arabidopsis thaliana*, wherein protein expression is desired. In addition to the *Arabidopsis thaliana* specifically exemplified herein, other plants can be used. Usually the construct is suitable for replication in a unicellular host, such as a bacterium, but a multicellular eukaryotic host may also be appropriate, with or without integration within the genome of the host cell. Desirably, the DNA construct of interest is stably incorporated within the genome of a plant cell of interest for the production of a sentinel plant for environmental monitoring. Commonly used prokaryotic hosts include strains of *Escherichia coli*, although other prokaryotes, such as *Bacillus subtilis* or a *Pseudomonas*, may also be used. Eukaryotic host cells include yeast, filamentous fungi, plant, insect, amphibian and avian species.

Polynucleotides may also be produced by chemical synthesis, e.g., by the phosphoramidite method described by Beaucage and Caruthers (1981) *Tetra. Letts.* 22: 1859-1862 or the triester method according to Matteuci et al. (1981) *J. Am. Chem. Soc.* 103: 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1995) *Current Protocols in Molecular Biology*, Greene Publishing and Wiley Interscience, New York; and Metzger et al. (1988) *Nature*, 334: 31-36. Many useful vectors for expression in bacteria, yeast, fungal, mammalian, insect, plant or other cells are well known in the art and may be obtained from vendors such as Stratagene, New England Biolabs, Promega Biotech, CAMBIA and others. In addition, the construct may be joined to an amplifiable gene so that multiple copies of the gene may be made. For appropriate enhancer and other expression control sequences, see also *Enhancers and Eukaryotic Gene Expression*, Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, kanamycin, hygromycin, BASTA, glyphosate, etc.; (b) complement auxotrophic deficiencies; or (c) supply critical nutrients not available from complex media. The choice of the proper selectable marker will depend on the host cell; appropriate markers for different hosts are known in the art.

Recombinant host cells, in the present context, are those which have been genetically modified to contain an isolated DNA molecule. The DNA can be introduced by any means known to the art which is appropriate for the particular type of cell, or plant or eukaryotic organisms, including without limitation, *Agrobacterium*-mediated, bacterial mediated, transformation, lipofection, particle bombardment or electroporation.

It is recognized by those skilled in the art that the DNA sequences may vary due to the degeneracy of the genetic code and codon usage.

Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. (1985) *Science* 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

It is well known in the art that the polynucleotide sequences of the present invention can be truncated and/or mutated such that certain of the resulting fragments and/or mutants of the original full-length sequence can retain the desired characteristics of the full-length sequence. A wide variety of restriction enzymes which are suitable for generating fragments from larger nucleic acid molecules are well known. In addition, it is well known that Bal31 exonuclease can be conveniently used for time-controlled limited digestion of DNA. See, for example, Maniatis (1982) *Molecular Cloning: A Laboratory Manual*, Cold Spring Harbor Laboratory, New York, pages 135-139, incorporated herein by reference. See also Wei et al. (1983 *J. Biol. Chem.* 258:13006-13512. By use of Bal31 exonuclease (commonly referred to as "erase-a-base" procedures), the ordinarily skilled artisan can remove nucleotides from either or both ends of the subject nucleic acids to generate a wide spectrum of fragments which are functionally equivalent to the subject nucleotide sequences. One of ordinary skill in the art can, in this manner, generate hundreds of fragments of controlled, varying lengths from locations all along a starting nucleotide sequence. The ordinarily skilled artisan can routinely test or screen the generated fragments for their characteristics and determine the utility of the fragments as taught herein. It is also well known that the mutant sequences of the full length sequence, or fragments thereof, can be easily produced with site directed mutagenesis. See, for example, Larionov, O. A. and Nikiforov, V. G. (1982) *Genetika* 18(3):349-59; Shortle, D., DiMaio, D., and Nathans, D. (1981) *Annu. Rev. Genet.* 15:265-94; both incorporated herein by reference. The skilled artisan can routinely produce deletion-, insertion-, or substitution-type mutations and identify those resulting mutants which contain the desired characteristics of the full length wild-type sequence, or fragments thereof, i.e., those which retain promoter activity. It is well known in the art that there are a variety of other PCR-mediated methods, such as overlapping PCR that may be used.

"Expression control sequences" are DNA sequences involved in any way in the control of transcription or translation. Suitable expression control sequences and methods of making and using them are well known in the art. The expression control sequences must include a promoter. The promoter may be any DNA sequence which shows transcriptional activity in the chosen plant cells, plant parts, or plants. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds, Nucleic Acids Res., 15, 2343-61 (1987). Also, the location of the promoter relative to the transcription start may be optimized. Many suitable promoters for use in plants are well known in the art as are nucleotide sequences which enhance expression of an associated expressible sequence.

For instance, suitable constitutive promoters for use in plants include promoters from plant viruses, such as the peanut chlorotic streak caulimovirus (PCISV) promoter (U.S. Pat. No. 5,850,019), the 35S promoter from cauliflower mosaic virus (CaMV) (Odell et al., Nature 313:810-812 (1985)), promoters of *Chlorella* virus methyltransferase genes (U.S. Pat. No. 5,563,328), and the full-length transcript promoter from figwort mosaic virus (FMV) (U.S. Pat. No. 5,378,619); the promoters from such genes as rice actin (McElroy et al., Plant Cell 2:163-171 (1990)), ubiquitin (Christensen et al., Plant Mol. Biol. 12:619-632 (1989) and Christensen et al., Plant Mol. Biol. 18:675-689 (1992)), pEMU (Last et al., Theor. Appl. Genet. 81:581-588 (1991)), MAS (Velten et al., EMBO J. 3:2723-2730 (1984)), maize H3 histone (Lepetit et al., Mol. Gen. Genet. 231:276-285 (1992) and Atanassova et al., Plant Journal 2(3):291-300 (1992)), *Brassica napus* ALS3 (WO 97/41228); and promoters of various *Agrobacterium* genes (see U.S. Pat. Nos. 4,771,002, 5,102,796, 5,182,200 and 5,428,147). Finally, promoters composed of portions of other promoters and partially or totally synthetic promoters can be used. See, e.g., Ni et al., Plant J., 7:661-676 (1995) and WO 95/14098 describing such promoters for use in plants.

The promoter may include, or be modified to include, one or more enhancer elements. Preferably, the promoter will include a plurality of enhancer elements. Promoters containing enhancer elements provide for higher levels of transcription as compared to promoters that do not include them. Suitable enhancer elements for use in plants include the PCISV enhancer element (U.S. Pat. No. 5,850,019), the CaMV 35S enhancer element (U.S. Pat. Nos. 5,106,739 and 5,164,316) and the FMV enhancer element (Maiti et al., Transgenic Res. 6:143-156 (1997)). See also WO 96/23898 and Enhancers And Eukaryotic Expression (Cold Spring Harbor Press, Cold Spring Harbor, N.Y., 1983).

A 5' untranslated sequence is also employed. The 5' untranslated sequence is the portion of an mRNA which extends from the 5' CAP site to the translation initiation codon. This region of the mRNA is necessary for translation initiation in plants and plays a role in the regulation of gene expression. Suitable 5' untranslated regions for use in plants include those of alfalfa mosaic virus, cucumber mosaic virus coat protein gene, and tobacco mosaic virus. It is understood that there should be a ribosome binding site (such as a Kozak sequence which is a DNA sequence which "surrounds" (both ends of) the ATG start signal (for translation of mRNA)) associated with the coding sequence on the mRNA.

For efficient expression, the coding sequences are preferably also operatively linked to a 3' untranslated sequence. The 3' untranslated sequence will include a transcription termination sequence and a polyadenylation sequence. The 3' untranslated region can be obtained from the flanking regions of genes from *Agrobacterium*, plant viruses, plants or other eukaryotes. Suitable 3' untranslated sequences for use in plants include, but are not limited to, those from the cauliflower mosaic virus 35S gene, the phaseolin seed storage protein gene, the pea ribulose biphosphate carboxylase small subunit E9 gene, the soybean 7S storage protein genes, the octopine synthase gene, and the nopaline synthase gene.

The term "RNA interfering molecule" includes but is not limited to diRNA, siRNA miRNA, or an antisense RNA to inhibit synthesis of a related coding sequence. It is part of a mechanism for RNA-guided regulation of gene expression in which double-stranded ribonucleic acid (RNA) inhibits the expression of genes with complementary nucleotide sequences.

As noted above, the DNA construct may be a vector. The vector may contain one or more replication systems which allow it to replicate in host cells. Self-replicating vectors include plasmids, cosmids and viral vectors. Alternatively, the vector may be an integrating vector which allows the integration into the host cell's chromosome of the DNA construct encoding the chlorophyll degrading enzyme and/or the chlorophyll biosynthesis-inhibiting sequence. The vector desirably also has unique restriction sites for the insertion of DNA sequences. If a vector does not have unique restriction sites, it may be modified to introduce or eliminate restriction sites to make it more suitable for further manipulations. It may also contain recombination sites to allow a variety of genes or gene fragments to be assembled or disassembled, accordingly.

The DNA constructs of the invention can be used to transform any type of plant or plant cell. A genetic marker can be used for selecting transformed plant cells ("a selection marker"). Selection markers typically allow transformed cells to be recovered by negative selection (i.e., inhibiting growth of cells that do not contain the selection marker) or by screening for a product encoded by the selection marker. The most commonly used selectable marker gene for plant transformation is the neomycin phosphotransferase II (nptII) gene, isolated from Tn5, which, when placed under the control of plant expression control signals, confers resistance to kanamycin. Fraley et al., Proc. Natl. Acad. Sci. USA 80:4803 (1983). Another commonly used selectable marker gene is the hygromycin phosphotransferase gene which confers resistance to the antibiotic hygromycin. Vanden Elzen et al., Plant Mol. Biol., 5:299 (1985). Additional selectable marker genes of bacterial origin that confer resistance to antibiotics include gentamycin acetyl transferase, streptomycin phosphotransferase, aminoglycoside-3'-adenyl transferase, and the bleomycin resistance determinant (Hayford et al. 1988. Plant Physiol. 86:1216, Jones et al. 1987. Mol. Gen. Genet. 210:86; Svab et al. 1990. Plant Mol. Biol. 14:197, Hille et al. 1986. Plant Mol. Biol. 7:171). Other selectable marker genes confer resistance to herbicides such as glyphosate, glufosinate or bromoxynil (Comai et al. 1985. Nature 317:741-744, Stalker et al. 1988. Science 242:419-423, Hinchee et al. 1988. Bio/Technology 6:915-922, Stalker et al. 1988. J. Biol. Chem. 263:6310-6314, and Gordon-Kamm et al. 1990. Plant Cell 2:603-618).

Additional selectable markers useful for plant transformation include, without limitation, mouse dihydrofolate reductase, plant 5-enolpyruvylshikimate-3-phosphate synthase, and plant acetolactate synthase (Eichholtz et al. 1987. Somatic Cell Mol. Genet. 13:67, Shah et al. 1986. Science 233:478, Charest et al. 1990. Plant Cell Rep. 8:643; EP 154, 204).

Commonly used genes for screening presumptively transformed cells include, but are not limited to, β-glucuronidase (GUS), β-galactosidase, luciferase, and chloramphenicol acetyltransferase (Jefferson, R. A. 1987. Plant Mol. Biol. Rep. 5:387, Teeri et al. 1989. EMBO J. 8:343, Koncz et al. 1987. Proc. Natl. Acad. Sci. USA 84:131, De Block et al. 1984. EMBO J. 3:1681), green fluorescent protein (GFP) and its variants (Chalfie et al. 1994. Science 263:802, Haseloff et al. 1995. TIG 11:328-329 and WO 97/41228). Another approach to the identification of relatively rare transformation events has been use of a gene that encodes a dominant constitutive regulator of the *Zea mays* anthocyanin pigmentation pathway (Ludwig et al. 1990. Science 247:449). Another screening method is to look for functional degreening phenotype as described herein in response to a specific inducer. Allowing the plant to regreen independent of the inducer allows recovery of the transgenic line.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1-4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein. Intermediate cloning of the PCR products can be done using the PCRTerminator end repair kit and CLoneSmart kit vector pSMART (Lucigen, Middleton, Wis.). Various PCR based cloning methods were used and are known to those skilled in the art.

All references cited in the present application are incorporated by reference herein to the extent there is no inconsistency with the present disclosure. References cited herein reflect the level of skill in the relevant arts.

The present invention exploits plants' sensing mechanisms for extracellular signals, with the development of plants that respond to a variety of biological, chemical, and environmental pollutants for substances of interest to produce a readily detectable response or phenotype. In a particular embodiment the plants disclosed herein lose green color when exposed to a specific substance; the degreening is an easily detectable biomarker and does not require sophisticated instrumentation. These plants function as "sentinels" and are especially useful for widespread monitoring of substances in the environment whether interior or exterior.

For the plants to be useful as degreening biomarkers to detect specific chemical agents or to monitor environmental factors, an appropriate input circuit was produced. This input circuit is useful for linking detection to response. When the input circuit is linked to the degreening circuit, a plant detector is produced. In addition, the ability to control response of plants and biological organisms to specific substances provides a useful tool for biotechnology allowing, for example, co-ordination of crop plants, facilitating harvesting and controlling other developmental, tissue or environmental responses.

The present invention provides a highly specific and sensitive method for plants to detect a target substance of interest in their environment, transmit the sensing from outside the plant to the nucleus, induce a specific transcriptional response and a type of output controlled degreening that provides detection to humans. In one embodiment of the invention, the regulatory circuits have two components, referred to herein as input and output circuits. In another embodiment of the invention, the input circuit has an ability to specifically recognize (bind) the target substance of interest and transmit a signal to the nucleus, where a specific response is initiated. The response can be a phenotypic and/or metabolic change of interest or a visible response to produce a plant sentinel. In one embodiment of the invention, one output circuit produces a degreening or other detectable phenotype in the transgenic plant containing the circuits. In one embodiment of the invention, the output circuit is also modular in that a variety of genes can be placed under control of the signal-inducible promoter. In one embodiment of the invention, the input circuit of the invention is modular in that the receptor that is targeted to the extracellular space can be designed to provide specificity and selectivity for binding a given target substance of interest. One specific input circuit specifically exemplified herein provides detection of the explosive trinitrotoluene. One specific output circuit specifically exemplified herein serves as a simple and sensitive marker that can easily be recognized directly (visually), or by remote sensing and/or by monitoring changes in chlorophyll fluorescence, by changes in photosystem I and/or photosytem II, electron transport, by changes in hyper-spectral imaging, and/or by changes in spectral properties.

The input circuit comprises a sensor protein specifically targeted to the extracellular space of the plant with a binding site specific for recognizing a target agent or a target substance of interest, a transmembrane histidine kinase protein, a nuclear shuttling protein, and a synthetically designed signal responsive promoter. Variations and elaborations described herein are found in various research publications, and known to those skilled in the art. One type of output circuit described herein activates the expression of one or more genes, which results in a degreening phenotype in transgenic plants containing the circuits.

The present invention provides a sensor protein or receptor at the cell surface, such that the sensor protein or receptor has a binding site specific for the target substance of interest. The transmembrane protein, a second component of the input circuit has three parts: an interacting domain, a transmembrane domain and a histidine kinase domain. Binding of the target substance of interest causes a conformational change in the sensor protein or receptor, so that it then binds to an interacting domain of the transmembrane protein on the exterior surface. The interaction of the sensor protein:target substance of interest complex results in activation of the histidine kinase, typically by an autophosphorylation mechanism. The interaction of the sensor protein or receptor with the interacting domain produces a conformational change in the transmembrane protein and/or transmembrane histidine kinase. The autophosphorylated histidine kinase domain of the transmembrane protein transfers a high energy phosphate group to a cytoplasmically located protein. A variety of proteins will function in the specific example described here: a synthetically adapted shuttling protein such as PhoB:VP64, other shuttling proteins such as histidine phosphotransferases, *Arabidopsis* histidine phosphotransferase, and other natural proteins such as response regulators from plants, bacteria, fungi, and cyanobacteria systems, including adapted or synthetic proteins that function in histidine kinase mediated signaling systems.

The shuttling protein typically has several functions including reception of the signal from the transmembrane protein, relay of this signal to the nucleus, or specific responding component, and/or activation of transcription. The protein may directly, or indirectly, bring about a cellular response. The typical cellular response is activation of transcription, however, other responses are possible including changes in membrane potential, cell expansion (in the case of engineering a response that would allow expansion of the xylem), or changes in the accumulation of a plant-derived product. At least some proteins are phosphorylated (directly) by the histidine kinase domain of the transmembrane protein. The phosphorylation of the proteins or protein components can cause an increase in binding affinity for a specific sequence of DNA as is the case for OmpR, or in the case of PhoB, allow a conformational change that removes repression, allowing the DNA binding domain to function. One type of response of this is a readout circuit that includes expression of the specifically regulated gene located in the nucleus of the plant and the production of a detectable phenotype, appearance or function of lack thereof or the readout can include activation of a gene controlling a trait of interest, for example, flowering or ripening.

The sensor protein or receptor can be derived from a bacterial (e.g., *Escherichia coli*) periplasmic binding protein (PBP), such as a maltose, ribose or galactose PBP, and the binding site for the target substance of interest can be a naturally occurring binding site or one which is the result of computational design. At the N-terminus there is also a signal peptide sequence for targeting the sensor protein to the exterior of the plant and plant cell; as specifically exemplified, the signal peptide is that of the pollen PEX protein (Baumberger, N. et al., 2003). Substances of interest can include, without limitation, plant hormones, explosives, chemical agents such as a nerve agent (e.g., soman), environmental pollutants including all currently listed environmental pollutants on the Environmental Protection Agency (EPA) superfund site, halogenated hydrocarbons, or degradation products, metal ions such as zinc, a heavy metal, a sugar, neurotransmitter, herbicides, pathogenic products, or an amino acid.

When the target substance of interest is bound to the sensor protein or receptor, there is an interaction with the protein which transmits a signal from the exterior of the plant to a protein by autophosphorylation and activation of the histidine kinase. Upon binding of the target substance of interest, there is an interaction between the sensor protein or receptor and the transmembrane protein (which contains the histidine kinase domain). This interaction causes autophosphorylation of a histidine residue located on the transmembrane protein. The phosphate is then transferred (a mechanism called phosphor-relay or phosphotransfer) to a shuttling protein or transcription activator protein domain, allowing it to translocate to the nucleus or otherwise initiate a response. The phosphorylated protein, protein domain or secondary protein then binds a DNA recognition sequence present in a promoter of a gene (or genes) in the nucleus, which can be a genetically engineered gene, with the result that transcriptional expression of that gene occurs.

The transmembrane protein can be genetically engineered as a translational fusion consisting of the plant and/or bacterial proteins, derived from one or more bacterial or plant proteins, derived from one or more proteins containing histidine kinase-like features, or synthetically synthesized features, provided that it functions in plants in conjunction with a protein or protein domain to transmit the signal to a response unit. As specifically exemplified, it can be a translation fusion of FLS-TRZ (Trg-EnvZ) with AHK4 (see herein below), a translational fusion of FLS-Trg-PhoR, or a translational fusion of FLS-Trg-EnvZ. The intracellular receptive protein or protein domain can be a plant protein, a bacterial protein or a synthetically designed protein, with the proviso that it receives the signal from the transmembrane protein. The receptive protein can either transmit the signal to another protein that initiates a response or translocate to the nucleus in response to the signal. In the case specifically exemplified, the signal receptive protein itself moves to the nucleus, binds DNA and activates gene expression. As specifically exemplified, it can be a plant histidine phosphotransferase or a bacterial protein such as the *E. coli* proteins OmpR or preferably PhoB. Where the signal receptive protein is also a transcriptional activation protein, PhoB, the DNA recognition sequence is CTGTCATAYAYCTGTCACAYYN (SEQ ID NO:14), and it can occur from 2 to 12 times, exemplified 4 or 8 times in the region upstream of the transcription start site, and includes a plant transcriptional start site such as defined by a minimal transcriptional promoter.

The sequence which is expressed in response to detection of, or the presence of, a target substance of interest in the plant environment can be a protein coding sequence or it can be a functional nucleic acid sequence (such as a RNA interfering molecule, diRNA or an antisense RNA to inhibit synthesis of a related coding sequence) or it can be a combination of these. The associated expressed sequence can be a plant gene which is, in nature, expressed constitutively or in a tissue or condition specific fashion, but in the present invention, it is expressed when the target substance of interest or substance which binds to the sensing protein or sensing proteins is present or after the target substance of interest is present. The expressed sequence can be virtually any sequence of interest: a detectable marker such as green or yellow fluorescent protein or another fluorescent protein, β-glucuronidase or β-glucosidase, among others, a positive regulator of flowering or a sterility protein preferably selectively expressed in the appropriate tissue, a bioremediation coding sequence such as mercury reductase, a phytochelatin or metal sequestering protein, an enzyme for detoxifying a contaminant or harmful material, and the production of a specific nutritive or pharmaceutical substance, among others. The expressed sequence can also be a functional nucleic acid (antisense or diRNA to inhibit expression of a related nucleic acid sequence). There can be more than one target substance-regulated gene within a single plant.

In an embodiment of the invention, the sensing circuitry can be used to control features of interest such as, the timing of flowering of a plant or ripening of a fruit such that harvesting is more synchronized, coordination of crops such as cotton, soybean and corn and hence an ability to predict harvest time, and thus, make harvesting more efficient and economical or so that plants are in flower for a particular occasion such as Easter, Mother's Day, Valentine's Day, Administrative Professional's Day or other holiday. Such a gene or response unit is operably linked to a promoter containing the recognition sequence of the specific sensing system or systems.

In another embodiment, the target substance of interest-dependent transcription regulatory system can be used to render plants exposed to the target substance sterile, when a sterility inducing protein is expressed under the regulatory control of the control system of the present invention.

Within the scope of the present invention are one or more DNA constructs containing a plant operable sensor protein as described above, a plant transmembrane protein, a plant operable signal reception and/or transcription activation protein that is activated by the histidine kinase portion of the sensing circuit (via an intermediary endogenous protein, the AHP, or directly by the membrane bound kinase), and a plant operable sequence operably linked to transcription regulatory sequences which include the recognition sequence of the particular transcription activating protein of the invention.

Similarly, the present invention provides transgenic plant cells, transgenic plant parts, transgenic plant tissue and transgenic plants containing one or more constructs of the present invention.

The present invention provides transgenic (sentinel) plants useful for environmental monitoring and for detecting particular biological and chemical agents, environmental pollutants, and/or a specific substance such as herbicides or trigger compounds. Trigger compounds are substances that bind to the natural or computationally designed sensor proteins and thereby increase the sensor proteins affinity for an extracellular protein domain, as specifically exemplified herein, Trg. In a specific embodiment, the plants disclosed herein lose green color within hours of exposure to particular target biological/chemical agents or environmental pollutants. The loss of green color (or a change in the fluorescence of chlorophyll or a change in photosynthetic electron transport) in plants is easily detectable, either by direct observation, with simple hand-held machines, or remotely by aircraft or satellite sensing. The sentinel plants of the present invention comprise genetically engineered DNA constructs which direct the expression of both the input and output circuits, as described below, with the result that the plants lose color when they "sense" the presence of the target substance of interest. An important advantage of the degreening system in these sentinel plants is that they are capable of regreening. They either regreen naturally or at an enhanced rate with treatment of hormones, i.e., the sentinels can be reset for renewed surveillance for the target substance to which they respond (Antunes et al., 2006). In one aspect of the present invention, a transgenic plant wherein degreening has occurred due to the presence of a target substance of interest is able to regreen after removal of the external target substance of interest.

The transgenic plants (sentinel plants) of the present invention can be indoor plants, for example, any of a number of species that are commonly used as decorative accent plants, such as peace lily (*Spathiphyllum*), philodendron, pothos (*Epipremnum*), spider plant (*Chlorophytum*), *Tradescantia* and *Dracaena*, and the like. In addition, the sentinel plants can be crop plants such as corn, wheat, soy, cotton, soybeans and others, or they can be grasses or trees, either deciduous (poplars, aspens, maple, oak, cottonwood, and the like) or evergreen (pines, spruce, junipers and the like) or they can be annuals or perennials used in various types of plantings, or they can be a variety of native species, or they can be aquatic plants including, but not limited to, algae. Nearly all plants and/or plant cells can be readily transformed and transformed seed directly formed or plants produced from the transformed cells, as is well known to the art. The sentinel plants of the present invention can provide a warning of current presence of a target substance of interest or they can provide notice to responders to a scene to allow for appropriate protective measures and/or to prevent exposure to a dangerous condition. In addition, the sentinel plants provide the ability to remotely monitor for the presence of substances. Moreover, the sentinel plants allow for continuous environmental monitoring over extremely large scales (e.g., hundred or thousands of square kilometers) that is not currently possible with any other publicly known method.

The sentinel plants of the invention contain a genetically engineered signaling pathway consisting of two functional parts referred to herein as "input" and "output" wherein one embodiment of the output is the "degreening" circuit". The input gene circuit is a natural or genetically engineered system that recognizes a biological or chemical agent, explosive, or an environmental pollutant or target substance of interest specifically and selectively, then activates an output gene circuit that results in the desired response. In the case of a plant sentinel, the output gene circuit shown here is the degreening circuit, so that the degreening phenotype i.e., white plants, are produced in response to an agent or pollutant. The degreening can be visually detected as a loss of green color or it can be detected as a change in chlorophyll fluorescence or in photosynthetic electron transport or it can be detected with a variety of spectroscopic methods such as hyper-spectral imaging and other methods.

The output and input circuits of the invention are generated by expressing DNA constructs specifically designed to provide a functional system. The input circuit is a system comprising a receptor or a binding protein designed to recognize (e.g. by binding) a signal (e.g. analyte or ligand), and this binding event ultimately activates a response, one of which is transcription of a gene of the output (degreening) circuit to produce a plant sentinel. Thus, the specificity and selectivity of a given response is determined by the input circuit. An example of the input circuit is a receptor or binding protein (sensor protein) which specifically binds a particular explosive, chemical agent or a pollutant, the target substance of interest, which, upon binding of such explosive, agent or pollutant, can transmit a signal via the transmembrane protein to activate transcription of a gene(s) in the output circuit. As specifically exemplified the sensor protein:target substance complex interacts with the exterior domain of the transmembrane protein, with the result that the histidine kinase becomes active. A sensor protein or receptor specific for a given ligand or analyte (target substance of interest), can be designed by using computational design (Looger, et al., 2003; Dwyer, et al., 2003; Marvin, J S and Helling a H W, 2001).

The response system (output, as exemplified by degreening) circuit is generated by transforming a plant with DNA constructs (i.e. expression vectors) comprising one or more nucleic acids encoding, or complementary to a nucleic acid encoding key enzymes or functional fragments thereof in chlorophyll biosynthesis and/or degradation pathway under the control of a promoter which responds to a signal from the input circuit. The term "functional fragment" as used herein, is intended to indicate that the product (i.e., enzyme) can be a truncated protein as long as it retains its enzymatic activity to cause degreening (chlorophyll degradation). One skilled in the art would know that a truncated protein may be able to maintain enzyme activity (U.S. Pat. No. 4,762,914).

Examples of chlorophyll degradation enzymes include, but are not limited to, RCCR, PaO and chlorophyllase. The output/degreening circuit also comprises a target-substance-regulated inhibition of chlorophyll biosynthesis. As specifically exemplified, this is achieved by expression of either antisense, or preferably, interfering RNA molecule (such as diRNA, siRNA) sequences specific to a coding sequence for an enzyme in the chlorophyll biosynthetic pathway. These interfering RNA molecules are examples of functional nucleic acids, and in the context of inhibition of gene expression, a functional fragment of a coding sequence or gene is one which specifically interacts with a transcript of the coding sequence or gene so as to reduce expression of the product of that gene or coding sequence. Examples of the enzymes involved in chlorophyll biosynthesis include, but are not limited to, protochlorophyllide oxidoreductase (POR), GUN4, other GUN genes (genome uncoupling), Mg chelatase and chlorophyll synthetase. It is understood that other targets in the chlorophyll synthesis or degradation pathway can be substituted for those specifically set forth.

The DNA construct for transforming the readout or degreening gene circuit into a plant or plant cell typically contains a nucleic acid encoding at least one chlorophyll degradation enzyme (or a fragment thereof which functions to effect chlorophyll degradation) and/or desirably also a nucleic acid whose expression product inhibits chlorophyll synthesis operably linked to a promoter with transcription regulatory sequences that bind a transcription activator protein that receives the signal from the input gene circuit. Typically it can be a transcriptional activator protein that solely receives the signal from the transmembrane histidine kinase and shuttles to the nucleus or a nuclear localized transcriptional activator protein that receives the signal from the transmission protein which relays the signal from the transmembrane histidine kinase and shuttles to the nucleus. The exterior component of the transmembrane histidine kinase has bound the sensor protein substance complex therefore relaying an input signal generated by an explosive, a chemical or biological agent, a pollutant or a specific substance. In response to the input signal, this dual modulation, i.e. inhibition of synthesis and stimulation of degradation of chlorophyll ensures loss of green color in plants when exposed to a variety of chemical agents or environmental pollutants. As described herein, chlorophyll synthesis can be inhibited by producing interfering RNA or antisense RNA derived from at least one of the genes encoding chlorophyll synthetic enzymes.

Figure 2A:
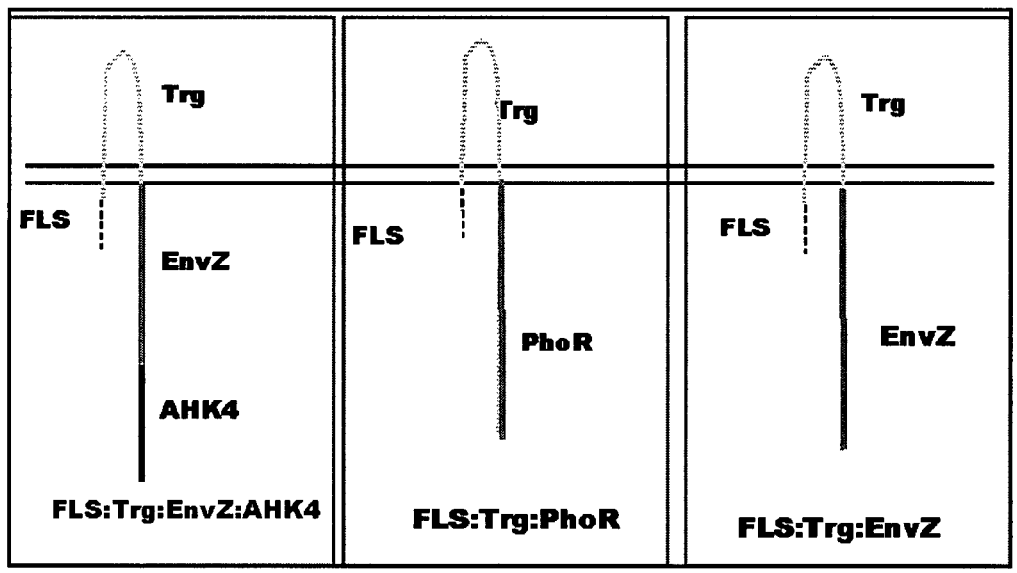
FIGS. 2A-2C show transmembrane proteins (histidine kinases) and their pathways that are used for transcriptional response.
Figure 2B:
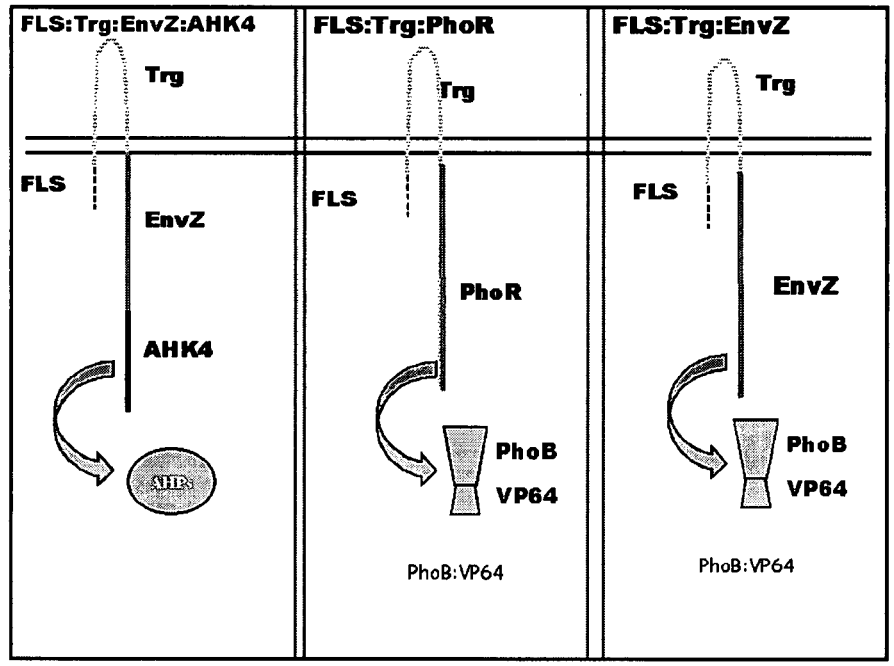
Figure 2C:
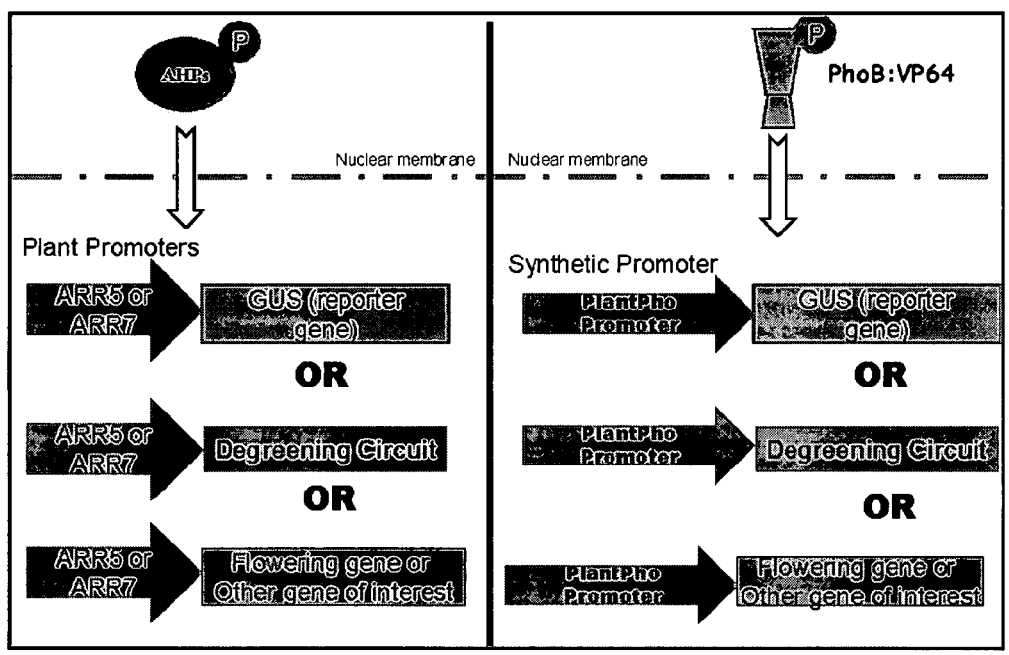

Specifically exemplified herein is an output (degreening) circuit expressing diRNA for POR and/or GUN4, and expressing proteins having RCCR and/or PaO and chlorophyllase activities, all under the regulatory control of a synthetic signal-receptive promoter (PlantPho) whose expression is controlled by an adaptive PhoB:VP64 signal receptive and transaction protein and the input circuit comprising the sensor protein which binds a target substance of interest. The transgenic plants containing the aforementioned degreening circuit lose green color, i.e., turn white, within hours of exposure to the target substance. It is possible to detect other changes in transgenic plants earlier in the process. A specifically exemplified input circuit comprises the SS-TNT sensor protein which interacts with one or more defined transmembrane proteins such as FLS:Trg:EnvZ:AHK4, or plant-bacteria hybrid transmembrane proteins such as FLS:Trg:PhoR or FLS:Trg:EnvZ transmembrane proteins (FIGS. 2A and 2B). The FLS:Trg:EnvZ:AHK4 protein transmits a high energy phosphate signal to a plant histidine phosphotransferase protein specifically exemplified here, AHP, which then activates transcription. The plant-bacteria hybrid transmembrane proteins (FLS:trg:EnvZ:AHK4, FLS:Trg:PhoR and/or FLS:Trg:EnvZ proteins) transmit a high energy phosphate signal to an adapted protein, PhoB:VP64, with the result that the PhoB:VP64 transcription activating protein is phosphorylated, translocate from the cytoplasm to the plant nucleus and activate expression of the degreening genes operably linked to the PlantPho promoter which is induced when the specific substance or substances are in the external environment of the plant or plant cell (FIG. 2C). This results in expression of the linked gene, in the specific case of a plant sentinel the relatively rapid degreening, via the inhibition of chlorophyll synthesis and the stimulation of the degradation of chlorophyll, demonstrating that the DNA constructs of the present invention provide regulated gene expression of the detectable marker.

Accordingly, a transgenic plant containing the input and output circuits disclosed herein loses its green color when exposed to a substance in the environment which activates the input circuit by binding to a specific receptor site (i.e., sensor protein) outside the plant. The substance can be, for example, nerve gas, mercury, lead, arsenic, uranium, cadmium, selenium, polycyclic aromatic hydrocarbon, a benzene, a toluene, a xylene, or a halogenated (chloro, fluoro, and chlorofluoro) hydrocarbon, explosives, any substance listed on the EPA superfund website, specific compounds involved in manufacture of compounds of interest, or a trigger substance to bring about a desired change in the plant or crop. In addition, the target substance which binds to a specifically engineered sensor protein and input circuit via the extracellular receptor could be an explosive such as trinitrotoluene, RDX, HMX or TATP, or a degradation product of one of the foregoing compounds specifically bound by the sensor protein.

The sensing and response system of this invention is modular in that it can be coupled with a variety of input circuits (sensor proteins) to provide specificity and selectivity for a particular chemical agent and/or other environmental factor of interest which is recognized by an available sensor protein that effectively interacts with the exterior domain of the transmembrane protein when the target substance is bound. Similarly, the readout gene which is expressed via the histidine kinase system or systems of this invention can be selected for a desired result, with the proviso that it is operably linked to a promoter and associated control sequences which interact positively with a transcription regulatory protein activated directly or indirectly by the histidine kinase and/or AHP, PhoB or OmpR, described herein. Specifically, receptors which are engineered to bind site specific to the target substance of interest (including but not limited to heavy metals, nerve agents such as soman or a degradation product thereof, such as pinacolyl methyl phosphonic acid), explosives and certain degradation products thereof, environmental pollutants such as MTBE, herbicides such as glyphosate and the like. The sensing circuit further includes the transmembrane protein with an external binding domain which interacts with the sensing protein-target substance complex and an intracellular portion which directs the phosphorylation of a transcriptional activator protein, as specifically exemplified by PhoB and/or modified and/or an adapted version of the PhoB protein. PhoB can also be phosphorylated by an endogenous plant histidine phosphotransferase. The phosphorylated PhoB (activated form) then binds to the PhoB cognate binding sequences which are part of the synthetic promoter operably liked to a chlorophyll degradation enzyme coding sequence (such as chlorophyllase). The transcriptional activator protein can also be a hybrid protein including but not limited to, PhoB:VP64 translational fusion protein and it is expressed in a transgenic plant expressing its coding sequence operably linked to a plant expressible promoter, which can be constitutive or which can include sequences for tissue-specific or condition-specific expression. The activator protein can be any eukaryotic transcriptional activator including, but not limited to VP16, VP64 and GAL4.

Histidine Kinase Signal Transduction System

Two component histidine kinase signal transduction systems are conserved between plants and bacteria (Stock et al., 2000; Koretke et al., 2000; Kakimoto, T., 2003; Kakimoto, T., 1996) and this conservation was the basis of forming a functional input (sensing) circuit.

In bacteria, sensitive chemotactic sensors exist to direct motile bacteria to nutrients, e.g., ribose. When a periplasmic binding protein such as the ribose binding protein binds its ligand, it develops a high affinity for the extracellular domain of bacterial chemotactic receptors such as Trg. Upon binding of the ligand/binding protein complex, a cytoplasmic histidine kinase is activated. Normally in the bacterium, this results in chemotaxis toward the food source. Hybrid histidine kinases have been expressed in bacteria where the cell surface PBP binding domain of Trg has been combined with the interior histidine kinase domain from proteins such as envelope Z (EnvZ) (Looger et al., 2003; Baumgartner et al, 1994). This hybrid protein activates transcription via phosphorylated transcription activator proteins. In the hybrid histidine kinases, the target substance is bound by the sensor protein, and the substance:protein complex binds to the interacting domain of the hybrid histidine kinase at the exterior side of the cell membrane, and that initiates activation of the histidine kinase (HK). The HK starts a phospho-relay (phosphorylation relay) through a bacteria response regulator (e.g., OmpR or PhoB) to activate transcription of bacterial genes. The phospho-relay always goes His→Asp→His, etc. In addition, at least some transcription activator proteins are phosphorylated (activated) by that same kinase domain.

Chemotactic binding proteins (periplasmic binding proteins) have been redesigned using computer-run computational design methods so that instead of binding substances such as ribose or galactose or maltose, the engineered proteins specifically bind a target substance of interest such as TNT, RDX, nerve gas, heavy metals, or other environmental pollutants or harmful substances.

Plants also use a two-component or histidine kinase signaling system that responds to cytokinin (a plant hormone). Plant signal transduction is more complex. The histidine kinases are "hybrid types". The plant HKs in *Arabidopsis* are known as AHKs. Upon sensing cytokinin, plant HKs phosphorylate an internal histidine kinase and initiate a phosphorelay internally to an aspartate residue located in the receiver domain of the same protein. The receiver domain transfers the phosphate group to an independent protein (AHP, *Arabidopsis* histidine phosphotransferase). The AHP moves into the plant cell nucleus upon phosphorylation and then transfers the phosphate group to a nuclear localized protein, ARR Type B, transcription factors that then initiate transcription of ARR Type A genes. Examples of ARR type A genes useful in the present invention include, but are not limited to, ARR5 and ARR7, or any Type A ARR gene. Other functionally equivalent sequences may also be used in the systems described herein.

Computer design enables the design of sensor proteins to bind with great specificity and sensitivity, a variety of compounds or substances. See, for example, US Patent Publications 2004/0118681, and 2004/0229290; Looger et al. (2003); Dwyer et al., (2003) and Allert et al. (2004). Periplasmic binding proteins as starting points for protein engineering are reviewed in Dwyer et al., 2004. In bacteria, the engineered receptors were targeted to the periplasmic space to sense various substances of interest. In plant cells, it is necessary to add (desirably at the N-terminus) a secretory sequence functional in plant cells so that the sensor protein is at the exterior of the cell and can bind the particular target substance of interest and it is necessary to delete the bacterial leader. The starting point is the engineered periplasmic binding protein, and the ending point is a detectable change resulting from a transcriptional response in the nucleus; computer-designed sensor proteins and molecular biological techniques allows for the combination. Hybrids at both the starting point and ending point allowed functional signaling.

To obtain information from outside the plant cell and transmit a signal to the nucleus of the plant cell, specifically engineered target sensing receptors were positioned outside of plant cells. The proof of concept work was done with the receptor or sensor protein for TNT (trinitrotoluene). The original receptors that are computationally designed are the periplasmic binding proteins: RBP, MBP (maltose binding protein) and GBP (galactose binding protein). Importantly, at least in part because the system is modular, PCR can be used to change the receptor/sensor protein portion from a receptor/sensor protein specific for TNT to a target substance of interest (RDX, nerve gas, zinc, heavy metal, environmental pollutant).

Plant Extracellular Space:

Plants are not known to have a functional periplasmic space. However, evidence indicates that there is a functional space between the plant plasma membrane and the outside. Small proteins can freely move and/or diffuse in the plant cell wall, better understood as a complex matrix, and even move and/or diffuse in the plant cuticle, the waxy coating that is found outside some plant organs (Baluska, F et al., 2003; Somerville, C. et al., 2004). In bacteria, the periplasmic binding protein contains a leader peptide portion that targets the protein to the periplasm. In plants, proteins are targeted to the extra-cellular space by way of the endoplasmic reticulum. Because of the different targeting mechanisms, a plant extracellular targeting sequence is needed and the bacterial periplasmic targeting leader must be removed.

Genetically Engineered Plants Capable of Losing Green Color:

The present invention also provides genetically engineered plants capable of losing green color in response to a signal (analyte or ligand) by simultaneously controlling expression of genes involved in chlorophyll biosynthesis and/or degradation. These plants are capable of receiving input from cytoplasmic and extracellular analytes and linking these components to the degreening circuit resulting in the loss of green color. Thus, the plants of this invention serve as a simple and easily detectable biomarker for adverse environmental input.

The degreening circuit is assembled in a "plug and play" manner. Hence, the sensor protein for TNT, which initiates the input, can be replaced by a different computationally designed sensor protein allowing the degreening circuit to respond to a specific target substance or target substances of interest. The principle of the invention is illustrated using the model plant species *Arabidopsis*, which allows rapid optimization of the degreening circuit and its response. However, the circuits described herein are readily introduced into other plant species such as those typical of shopping malls, office buildings, landscapes, forested areas, cropland or aquatic systems.

The plants of this invention that lose their green color in response to a target substance can serve as untiring sentinels reporting on adverse input from the environment (e.g., chemical weapons or pollutants). Plant sentinels would be unthreatening to the general public and can be deployed in shopping malls and office buildings and at special events where most people can recognize a loss of green color and security personnel could easily detect the changes within a short period with inexpensive hand-held machines. In addition, loss of green color or other disruption of chlorophyll, such as chlorophyll fluorescence, or photosystem electron transport or hyper-spectral imaging can be rapidly quantified by authorities with either portable hand-held equipment or simple laboratory equipment (spectrophotometers). In vast geographic areas, detector systems could be introduced into plants typical for landscapes and aquatic systems, allowing satellites to identify adverse environments.

The degreening circuit of the invention induces genes that are involved in chlorophyll breakdown and synthetic genes for inhibiting chlorophyll synthesis. Simultaneous expression of the genes that initiate chlorophyll breakdown and inhibit new chlorophyll biosynthesis would yield the most efficient degreening phenotype. For this reason, the degreening circuit exemplified herein was created using three genes, two in the chlorophyll degradation pathway and one inhibitory gene in the chlorophyll biosynthesis pathway. A person of ordinary skill in the art understands that other combinations of the genes that are known to be involved in chlorophyll synthesis and degradation can be used to obtain the degreening phenotype demonstrated herein. In addition, a person of ordinary skill in the art understands that the reactive oxygen species (ROS) generated in the chloroplast and reported in Antunes et al., 2006, could be used to initiate and generate the degreening within plastids.

The degreening circuit of the invention can respond in two different ways; it can respond to target substances within the cytoplasm as well as those that are extracellular. To test the ability of the degreening circuit to function with cytoplasmic input in plants, a synthetic cytoplasmic receptor is linked to the circuit. In response to binding an analyte, the cytoplasmic receptor is transported to the nucleus where it activates synthetic transcriptional promoter(s) fused to genes whose products degrade chlorophyll while preventing new chlorophyll biosynthesis. To test the ability of the degreening circuit to function with input from outside the plant, an input circuit containing a chimeric receptor or binding protein can be linked to the degreening circuit. In response to binding an analyte, the extracellular receptor initiates a signal transduction pathway and activates a signal receptive synthetic transcriptional promoter fused to genes whose products degrade chlorophyll while preventing new chlorophyll biosynthesis.

Figure 1F:
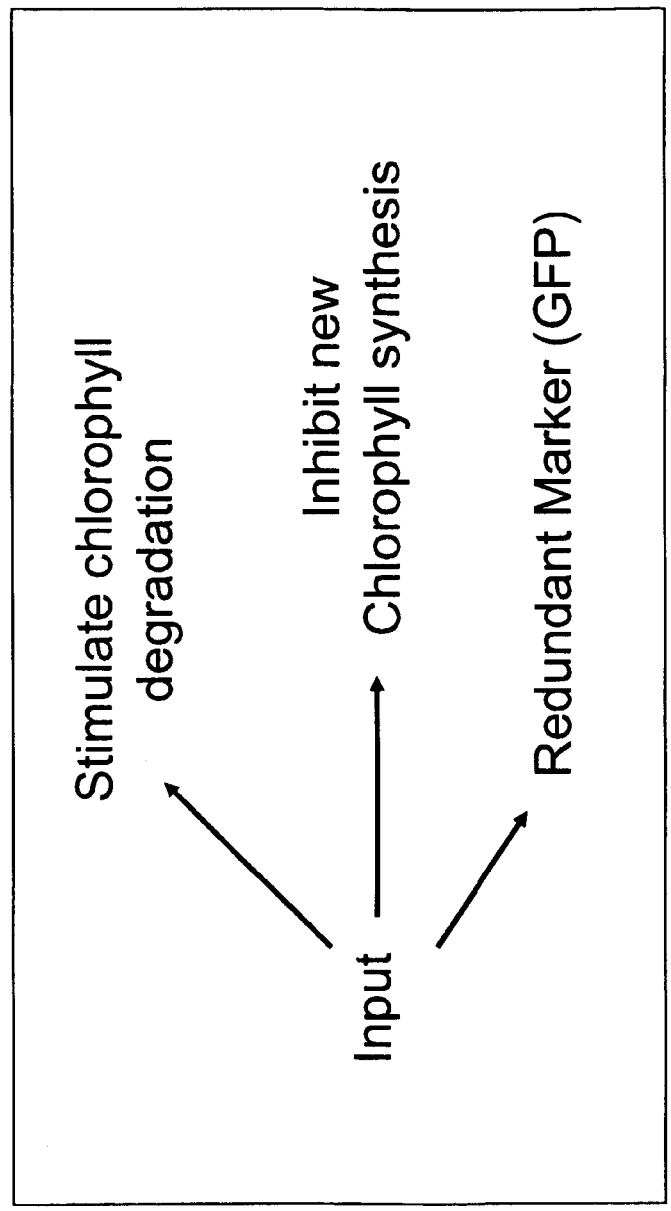

Normal time periods for notable loss of green color in plants varies widely from days to weeks depending on whether the loss is triggered from environmental changes, development (e.g., flower petals) or stress (e.g., pathogens). To develop a system that can lose green color rapidly in response to a signal, both the chlorophyll biosynthesis and chlorophyll breakdown pathways were modified to construct a "degreening circuit". The degreening circuit is shown schematically in FIG. 1F. In addition to genes involved in chlorophyll metabolism, a redundant marker, green fluorescent protein (GFP) can be included in the degreening circuit as a control. The GFP marker is similarly (optionally) linked to the input part of the circuit and serves to eliminate false positives that might arise.

There has been only one study where genes involved in chlorophyll metabolism have been purposely altered in transgenic plants (Benedetti and Arruda, 2002). In their study, the chlorophyllase gene was over-expressed in *Arabidopsis* plants and the plants remained green, but had an enormous increase in the level of the breakdown product chlorophyllide. To ensure that the degreening phenotype appears rapidly, two genes (for example, chlorophyllase and RCCR) were used in the degreening circuit exemplified herein. Although it was not measured, the turnover in chlorophyll is strongly believed to have stimulated feedback induction of new chlorophyll biosynthesis. To prevent this from occurring in the degreening circuit, expression of the protochlorophyllide oxidoreductase (POR) gene, the rate-limiting enzyme in chlorophyll biosynthesis was inhibited.

One approach to prevent expression of (silence) a specific gene involves the production of an interfering RNA molecule that contains a sequence identical to the gene of interest (McManus and Sharp, 2002; Wang and Waterhouse, 2002). Typically, the plants are genetically engineered to express inverted repeats (500-700 bp) to the gene of interest. The resulting double-stranded RNA is homologous to an endogenous transcript. Transgenic plants containing diRNA show high turnover rates of the homologous transcript and complete silencing of the endogenous gene expression (Chuang and Meyerowitz, 2000; Welsey et al., 2001; Wang and Waterhouse, 2002). An interfering RNA molecule has been shown to be more efficient than antisense RNA in blocking the expression of a desired gene with silencing frequency between 90-100% (Waterhouse et al., 1999; Chuang and Meyerowitz, 2000; Smith et al., 2000; Welsey et al., 2001; Stoutjesdijk et al., 2002; Wang and Waterhouse, 2002). Based on these studies, the initial degreening circuit is generated using double stranded RNAs to silence the POR gene in a transgenic plant and hence prevent the de novo synthesis of chlorophyll after input from an analyte. A series of convenient *Arabidopsis* vectors for making dsRNA constructs (developed by Jorgensen and Chandler) can be obtained from the *Arabidopsis* Biological Resource Center, Ohio State University. These vectors are based on the binary vector pBCAM-BIA1200 (Cambia, Black Mountain, AU) and contain a cassette for cloning a desired gene or gene portion in the sense and antisense orientations. The cassette has two pairs of unique restriction enzyme recognition sites flanking a 335 base pair GUS (β-glucuronidase) fragment that separates sense and antisense regions of the inverted repeat and facilitates formation of the dsRNA. The vectors are a series of plasmids that replicate in both *E. coli* and *Agrobacterium tumefaciens* allowing easy cloning and plant transformation, respectively. Vectors are available carrying the Bar or NptII genes, the plants containing the introduced genes can be selected with the herbicide BASTA (glufosinate ammonium) or the antibiotic kanamycin, respectively. A chloamphenicol or spectinomycin gene provides bacterial selection. The conserved region of protochlorophyllide oxidoreductase (POR) gene is cloned as described below in the sense and antisense direction to produce the diRNA molecule specific for the POR genes. The vectors are designed to direct expression of the diRNA molecule with a strong constitutive promoter (CaMV 35S). To place the diRNA vector in the degreening circuit, this promoter, which is flanked with unique restriction sites, is replaced with promoters that place expression under control of perception of cytoplasmic or extracellular analytes for example, using the Pho promoter described.

Plant transformation methods are routine, with *Arabidopsis* transformation among the easiest. *Arabidopsis* transformation is easily accomplished by spraying, dipping or contacting flowers with a solution of disarmed *Agrobacterium tumefaciens* containing the genes of interest (Bechtold et al., 1993; Clough and Bent, 1998; Chung et al., 2000; Desfeux et al., 2000). The various constructs can all be introduced into binary plant transformation vectors that provide the plants with resistance to kanamycin, BASTA or hygromycin. Once the individual components are assembled in binary plant transformation plasmids, they are then introduced into a disarmed strain of *Agrobacterium tumefaciens* (e.g., ASE or GV4111) (Fraley et al., 1985). The *Agrobacterium* cells are then grown to an $A_{600}$ of 0.5 in one liter batches, prepared as described (Clough and Bent, 1998; Chung et al., 2000) and effectively contacted with flowering *Arabidopsis* plants. The plants are allowed to set seed, the mature seed collected and transformed plants selected by either resistance to the antibiotics kanamycin and hygromycin or herbicide resistance to BASTA.

Assembly and Testing of Degreening Gene Circuits.

In many biological responses, sensing of a specific substance leads to a transcriptional response. The synthetic sensing system for plant sentinels links input to transcriptional output (Looger et al., 2003); hence, we created a test readout system triggered by a transcriptional response (signal-regulated induction of gene expression). Numerous transcriptional induction systems are available which provide a model in which to test the chlorophyll reporter system. A synthetically designed, steroid inducible system was modified to function in plants. In the presence of a synthetic steroid (4-hydroxytamoxifen, 4-OHT), a chimeric transcriptional regulator relocates to the nucleus and induces expression of a promoter made up of specific response elements and the −46 region of the CaMV35S promoter, designated 10XN1P. The 4-OHT induction system is essentially analogous to other transcriptional inducible systems (Zuo et al., 2000).

In order to use plants to monitor large areas for pollution or terrorist agents, a reporter or readout system is needed. Prior gene reporter systems were developed for laboratory use and do not provide characteristics needed for a plant sentinel. A synthetic degreening circuit was developed that allows the green pigment chlorophyll to be used as a biosensor readout system. Induction of the degreening circuit allows remote detection, displays a rapid response, provides a reset capacity, and results in a phenotype readily recognized by the general public. Because the degreening circuit produces a white phenotype, it is easy to distinguish it from plants stressed from biotic or abiotic conditions, which produce yellow (or other color) phenotypes via senescence-related pathways. The inability to reset biosensors has been the major limitation to their use. The degreening circuit provides a simple capacity to be reset. Plants regreened after removal of the inducer, and this regreening was enhanced by a brief cytokinin treatment. Because the transcriptional inducer used (4-OHT) is relatively stable, the degreening circuit may not fully switch to an "off" position immediately following removal of the inducer, and the regreening process may not start until the inducer within the plant degrades. Hence, it should be possible to substantially reduce the time needed for regreening, currently 3 days.

It should also be possible to reduce the response time from less than two hours to minutes. Our initial time point at two hours detected substantial reduction in $\phi_{PSII}$, one of the most robust parameters in chlorophyll fluorescence imaging. The rapid decline seen at two hours suggests we could detect changes earlier; indeed, detailed statistical analysis of the fluorescence parameters should allow us to accurately determine when the first significant changes can be detected. In addition to improving remote detection ability, the genetic circuitry could be further enhanced by rationally applying principles developed for synthetic gene circuitry (McDaniel and Weiss, 2005). For example, gene circuitry could be designed to be activated and remain active upon a single exposure to a small amount of inducer (via the sensing pathway) using a trigger function as described in FIG. 9.

The degreening circuit, combining "stop-synthesis" with an "initiate breakdown" function, caused loss of chlorophyll with unprecedented speed. When each function was introduced separately, plants did not visibly degreen in the 48 hour timeframe except in the cotyledons. Expression of the "initiate degradation" circuits (CHLASE and PAO, or CHLASE and RCCR) failed to produce rapid degreening, suggesting that plants can enhance chlorophyll biosynthesis when needed. Likewise, the "stop synthesis" circuits (diRNA specific to POR or GUN4) failed to produce rapid degreening, supporting the concept of a large amount of metabolically stable chlorophyll within the plant. The rational combination of these two functions in one T-DNA construct produced a synthetic "degreening circuit". The designed gene circuit is successful with respect to signal responsiveness, as indicated by three types of data: response of excised leaves to dark-induced senescence, distinctive ultrastructural changes, and microarray data showing a difference in genes regulated by the degreening circuit and normal chlorophyll loss in senescence.

Because of the massive damage to the photosystems, evidence of reactive oxygen species (ROS) was determined. FIG. 5D shows massive accumulation of ROS in the degreening leaf cell but not in the untreated leaf cell.

Light was shown to be important for the rapid degreening process to occur, as induced plants incubated in the dark failed to turn white, even after 72 hours of induction. When induced plants were transferred to light, degreening proceeded at an enhanced rate (FIG. 5E). These results suggest that the degreening circuit is poised to respond in darkness, but not able to initiate rapid degreening without light. Chlorophyll biosynthesis and breakdown intermediates are potentially phototoxic (Matile et al., 1999). Because the degreening circuit interferes with the normal balance of chlorophyll and likely its metabolic intermediates, it is possible that, upon light exposure, these molecules cause photo-oxidation of pigments. A similar light requirement for degreening was observed for detached leaves. Under standard light conditions degreening induction caused detached leaves to fully degreen within 48 hours. However, darkness failed to induce full degreening in detached leaves, even after 72 hours of induction. Because darkness has been shown to induce senescence in *Arabidopsis* detached leaves (Weaver and Amasino, 2001), these results suggest that chlorophyll loss from the degreening circuit is distinct from senescence.

Because light is required for rapid chlorophyll loss, we looked at how light is handled by plants induced to degreen by the detection of an environmental signal. The use of remote measurements of chlorophyll fluorescence provides an easy detection system for plant sentinels. $\phi_{PSII}$ measures the proportion of the light absorbed by chlorophyll associated with photosystem II (PSII) that is used in photochemistry. It is an indication of the plant's overall photosynthesis (Maxwell and Johnson, 2000). Degreening plants show a rapid decline in $\phi_{PSII}$ within 2 hours of induction, suggesting that induction of the degreening circuit quickly disrupts photosynthesis, and provides a quick way of detecting changes in plant sentinels. $F_v/F_m$, a widely-used parameter used for assessing the plant's level of stress, has an initial value of 0.8 in uninduced plants, indicating non-induced plants are not stressed. Induction of the degreening circuit causes a decline in $F_v/F_m$ values, when compared to controls, also an indication that the photosynthetic ability of degreening plants is disrupted.

Decreases in $F_v/F_m$ typically result from a combination of two processes: increases in the rate constant for thermal dissipation and/or decreases in the rate constant for photochemistry. Because light is required and the plants lose chlorophyll and yellow pigments, one possibility is that excitation energy is dissipated from chlorophyll by interaction with xanthophylls and other accessory pigments. De-excitation of chlorophyll was shown to occur by a rapidly reversible electron exchange between chlorophyll and zeaxanthin (Holt et al., 2005). If chlorophyll dissipates energy through zeaxanthin, we predicted a substantial change in non-photochemical quenching (NPQ). However, while NPQ measurements changed with induction, these changes were variable both in time and among the degreening circuits, indicating that it was not the primary means through which the degreening circuit functions. Hence, the decrease seen in $F_v/F_m$ was not primarily caused by enhanced thermal dissipation. Because $\phi_{PSII}$ and $F_v/F_m$ decrease prior to substantial decreases in chlorophyll levels, our data suggested that the degreening circuit functions by the inactivation or removal of PSII cores, which precedes substantial removal of chlorophyll. If the degreening circuit functions through inactivation or removal of PSII cores, there should be a large production of reactive oxygen species (ROS).

In degreening plants, ROS was first detected after 8 hours with substantial accumulation of ROS seen at 30 hours, consistent with the hypothesis that the degreening circuit functions by loss or damage of PSII cores. A mechanism proceeding via ROS action on photosystem cores would also account for the results that degreening circuits with varying gene compositions all produce a similar phenotype.

If ROS and/or damage to photosystem cores are key to initial degreening circuit function, the microarray analysis at 24 hours should indicate that genes typically involved in photosystem repair are significantly down-regulated. DegP2, encoding a protease that is responsible for initial repair of damaged PSII proteins (Haussuhl et al., 2001) is down-regulated. In addition, FtsH6, a chloroplast LHCII protease (Zelisko et al., 2005) is likewise down-regulated. Further analysis of microarray data suggests that various PSII- and PSI-related genes are down-regulated, while ROS-related genes are simultaneously up-regulated, indicating a process largely distinct from normal chlorophyll loss in senescence.

The degreening circuit provides an effective means to control chlorophyll levels in plants. The trigger for the degreening circuit is a specific input, resulting from sensing of the binding of a target substance of interest outside the plant, with signal transduction via histidine kinase within the cell and nuclear transcription activation. The steroid-inducible 10XN1P promoter used with the degreening circuit as a model can be replaced with other promoter elements, such as those responsive to signal transduction (Sakai et al., 2000) or the synthetic PlantPho promoter, as readily understood in the art. By combining the controlled chlorophyll loss as a reporting element with a sensing system such as computationally designed receptors or sensor proteins that provide input via transmembrane histidine kinases (Allert et al., 2004; Looger et al., 2003), plants are produced to serve as inexpensive monitors for terrorist agents, environmental pollutants or other target substances of interest. Degreening indicating presence of the target substance can be observed visually at close range or detected from a distance by remote sensing, as known to the art.

All DNA constructs, transgenic plant cells, tissue and plants, and methods for detecting a target substance of interest or for obtaining gene expression in response to the presence of the target substance of interest are within the scope of the present invention. It is further understood that other evolutionarily conserved signal transduction components and systems, transcription regulatory components and can be substituted for those recited herein, provided that there are functional input and/or output circuits responsive to the presence of a target substance.

EXAMPLES

The following examples are provided for illustrative purposes, and are not intended to limit the scope of the invention as claimed herein. Any variations in the exemplified articles which occur to the skilled artisan are intended to fall within the scope of the present invention.

In plant pollination, a large number of proteins are targeted to the extracellular space as a means of protein pollen-pistil (male-female) recognition. An example of one of these proteins is PEX (Pollen Extension-like protein). The leader peptide from a pollen protein called PEX (At1g49490=PEX) targeted proteins outside the pollen during the fertilization process (Baumberger, N. et al., 2003). Using overlapping PCR technology the coding sequence for this leader was fused to the periplasmic binding proteins' coding sequences to target them to the extra-cellular space in plant cells. In addition, an N-terminal bacterial leader which properly targets the periplasmic binding protein to the periplasm in bacteria was removed (interfered in proper targeting in plant cells). The PEX SS(SS, secretory sequence) and the computationally designed RBP coding sequence yielded a chimeric coding sequence of 900 bp (SS:TNT). See SEQ ID NO:7 and SEQ ID NO:8.

Figure 3A:
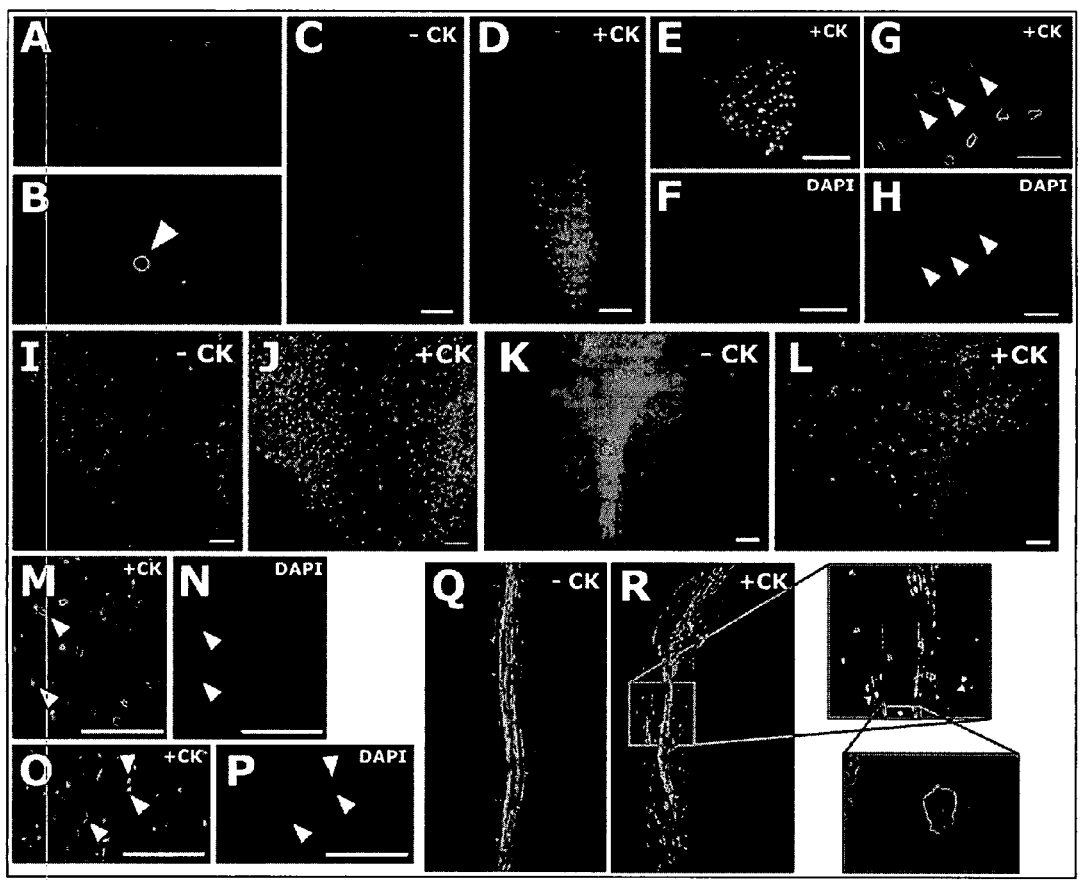
FIGS. 3A-3E show evidence for signal-dependent nuclear shuttling of bacterial response regulators in plants.
Figure 3B:
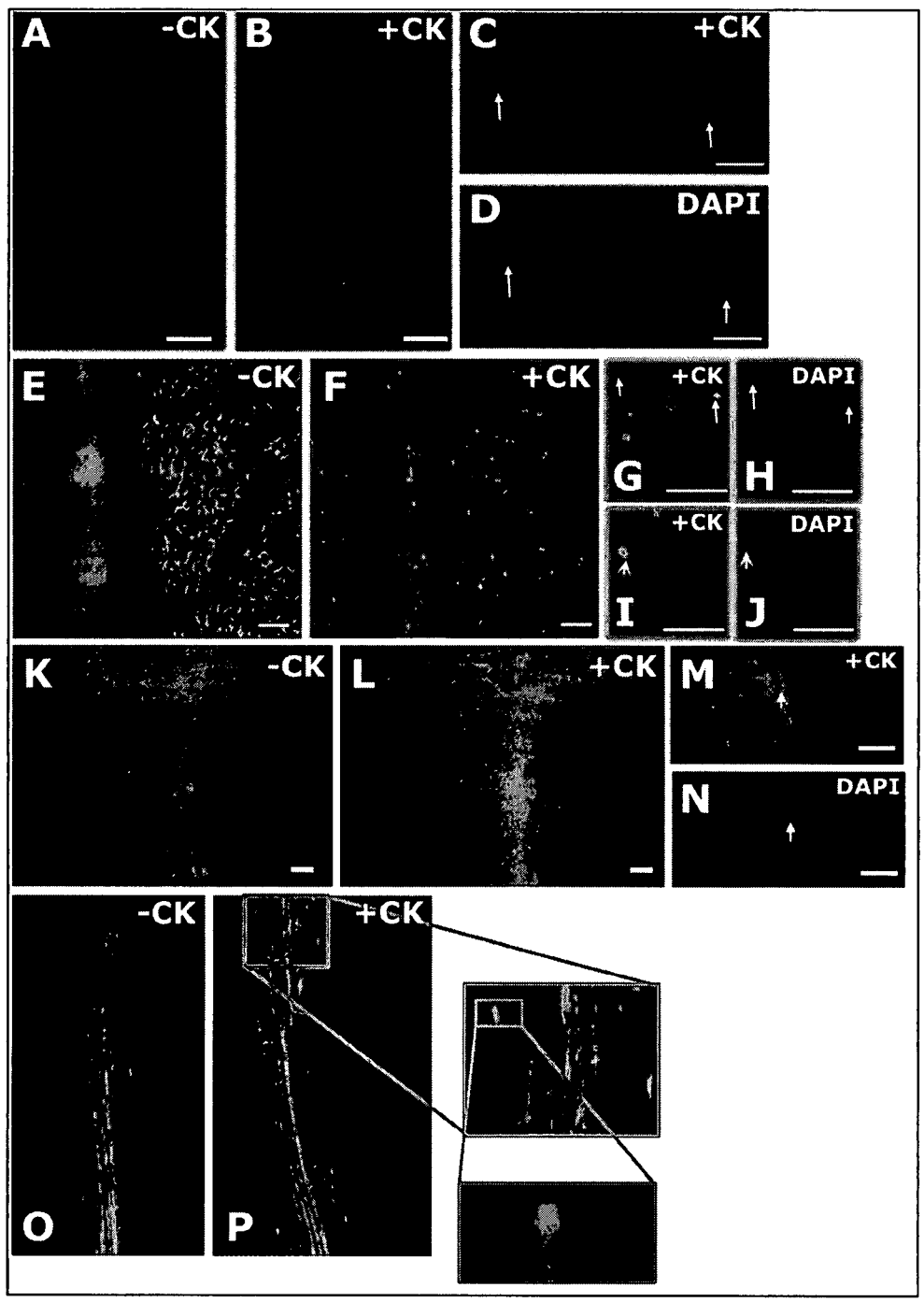
Figure 3C:
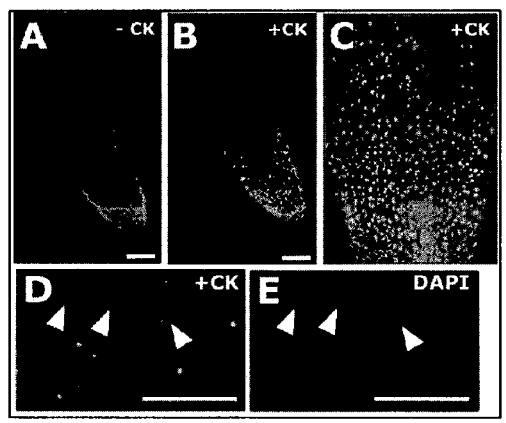

Fusion proteins with GFP (green fluorescent protein) and the above listed constructs were made and transient assays (particle bombardment of nucleic acid constructs into onion epidermal cells) were used to determine if any of these constructs were properly targeted to the outside of the plant cell. These assays showed that SS:RBP was present throughout the cell, with no specific localization to the plant cell wall. Removal of the bacterial leader and addition of the PEX leader was found to properly target the periplasmic binding protein to the extracellular space, the cell wall matrix.

It is possible that the highly hydrophobic nature of the native bacterial signal peptide might interfere with the plant signal peptide and interfere with proper targeting. In the ssRGDRBP fusion protein, the PEX SS is separated from the RBP hydrophobic signal peptide by the RGD motif. This separation kept the bacterial sequence from interfering with the PEX SS. Two new ssRBP fusions were also designed. The first fusion has the RGD motif minus the amino acids RGD between the SS and RBP (ss-linker-RBP), and the second fusion had the SS fused to RBP with the bacterial hydrophobic signal peptide deleted from the RBP protein (ssRBP no RBPss). Both fusions were able to target the RBP outside of the plasma membrane.

Constructs described above properly targeted the periplasmic binding protein to the plant cell wall. The bacterial hydrophobic leader was removed and replaced in its entirety with the plant leader (SS PEX). The amino acids RGD were removed from the linker and the linker was used to separate the plant leader (SS-PEX) from the bacterial leader.

Cells were plasmolysed to show proper targeting of the periplasmic protein (in this case RBP) to the plant extracellular space. Plasmolysis causes the plant protoplast to shrink away from the cell wall revealing localization of the periplasmic protein in the extracellular space. Plasmolysis of cells expressing the GFP fusion protein showed that targeting takes the periplasmic protein to the extra-cellular space. The data suggested that the targeted periplasmic binding protein fusion (SS-RBP:GFP) can freely diffuse in the cell wall.

A quick assay for reliable function was developed to show proper targeting of bacterial histidine kinases in plants. Plant systems transfer two-component signaling information from the membrane localized histidine kinase to the nucleus via histidine phospho-transferases. In plants, all published reports indicate this transfer is transient. In bacteria, information is transferred from the membrane localized histidine kinase to the bacteria chromosome via proteins called response regulators.

In planta nuclear shuttling ability of both plant AHPs (histidine phosphotransferases) and bacterial response regulators using translational GFP fusions were tested. The fusions were first tested in transient assays and then stably introduced into transgenic plants. In bacteria, both the plant AHPs and bacterial RRs function in a signal dependent manner. Hence, it is possible to test both the normal plant AHPs and the bacterial RRs using a normal plant signaling molecule, the hormone cytokinin, using evolutionary functional cross-talk between kingdoms.

Bacterial Response Regulators:

Bacterial response regulators and other heterologous signaling components are determined to be able to function in plants and shuttle to the nucleus. Two bacterial response regulators (PhoB and OmpR) were fused to GFP and transformed into *Arabidopsis* plants. OmpR is the bacterial response regulator which has been used in certain engineered systems. In bacteria, OmpR receives a phospho-relay signal from the bacterial histidine kinase EnvZ (envelope Z), with the result that affinity for bacterial promoter elements is increased. PhoB is a bacterial response regulator that will also pick up a phosphorylation signal from EnvZ, although its natural histidine kinase is the bacterial PhoR. Once PhoB receives a phosphorylation signal, its conformation changes and it develops a high affinity for bacterial promoters. When the phosphorylated PhoB protein is bound to the promoter, transcription is activated. In plants this was studied with the GFP fusion in leaves, petioles, roots and the crown (stem-like region in *Arabidopsis*). FIGS. 3A and 3B show that a signal-(cytokinin) dependent movement of the bacterial response regulators into plant cell nucleus was observed. There was a signal-dependent movement of the bacterial response regulators into the plant nucleus in every tissue and cell type examined. The PhoB:GFP shows strong signal dependent nuclear shuttling. OmpR also showed signal dependent nuclear localization, through somewhat less efficiently.

Transgenic roots were examined using a confocal microscope to confirm that the bacterial response regulators (PhoB:GFP, OmpR:GFP) moved into the nucleus, rather than associating with the nuclear membrane. If the PhoB and OmpR fusions were caught at the nuclear membrane, a roundish or 'donut' shape would be seen in a confocal microscope. However, confocal microscopy of PhoB:GFP transgenic roots indicated that there was nuclear localization in response to the cytokinin signal. There was no evidence of PhoB at the nuclear membrane. OmpR:GFP also is localized to the nucleus, but showed less shuttling than the PhoB:GFP fusions. Thus, the bacterial response regulators (PhoB and OmpR) act as membrane-to-nucleus shuttling proteins for the phospho-relay.

To rule out the possibility that the bacterial response regulators accumulate in the nucleus simply because they can diffuse through the nuclear membrane (both proteins have a molecular mass of approximately 27 kDa), a larger fusion protein was made by adding the β-glucuronidase (GUS) coding region to the C-terminal end of the PhoB:GFP fusion protein. The resulting protein, PhoB:GFP:GUS, has a predicted molecular masses of 122 kDa. This larger fusion protein was transformed into *Arabidopsis* and transgenic plants analyzed. Transgenic roots were examined before and after the cytokinin treatment under an epi-fluorescence microscope. FIG. 3C shows that PhoB:GFP:GUS fusion protein accumulates in the nucleus after cytokinin treatment. DAPI staining confirmed the compartments' identity as nuclei. Therefore, the bacterial response regulator PhoB move into plant nuclei in a signal-dependent manner, and that the movement is not through diffusion.

Figure 3D:
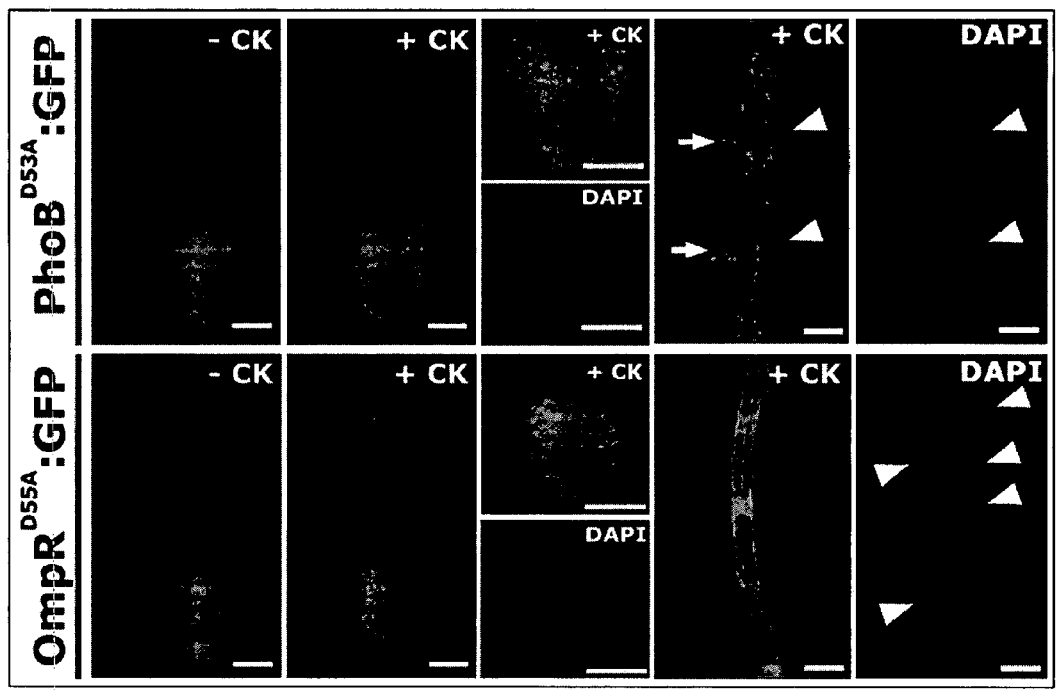

In bacterial cells, PhoB and OmpR proteins are phosphorylated at conserved Asp residues (D53 in PhoB and D55 in OmpR) by their cognate histidine kinase. Transgenic plants were generated that contained mutated forms of PhoB:GFP and OmpR:GFP, where the conserved Asp residues were mutated to Ala. FIG. 3D shows that fluorescence from PhoB$^{D53A}$:GFP is diffuse in an untreated root. The same root after cytokinin treatment shows a different pattern of PhoB$^{D53A}$:GFP localization when compared to wild-type PhoB:GFP. A detailed view of the root shows that nuclear localization of PhoB$^{D53A}$:GFP is variable and sporadic (arrowheads point to nuclei). In most cases, PhoB$^{D53A}$:GFP seems to accumulate at the base of cortical cells (arrows and some nuclear accumulation was seen in vascular cells only. In contrast, mutation of Asp55 in OmpR completely abolishes its signal-dependent nuclear shuttling.

Hybrid Histidine Kinases:

Because bacterial cell membranes and plant cell membranes differ substantially in components, it had not been expected that both the extracellular receptor which responds to the computationally designed periplasmic binding proteins and the transmembrane histidine kinase could be derived from bacteria. It was believed that hybrid histidine kinases with plant and bacterial segments would be required for the transcription regulatory circuits of the present invention to be functional. Certain hybrid histidine kinases had already been made with bacterial components. However, with the incorporation of a plant secretory sequence, both types of histidine kinases were successful.

While the specifically exemplified transmembrane proteins described herein include segments from the bacterial histidine kinase TRG (or TRZ) and the plant AHK4 histidine kinase, other transmembrane proteins can supply the kinase function in a chimeric transmembrane protein. Additional histidine kinases are described in Inouye, Mand Dutta, R., eds. (2003) Histidine Kinases in Signal Transduction, Academic Press, NY. Examples of bacterial HKs which can be utilized in the transmembrane protein of the present invention include por S, arc B, bar A and evg S. A Trz-PhoR fusion with a plant signal sequence has also been produced; see SEQ ID NO:2, SEQ ID NO:3 and SEQ ID NO:12.

It was discovered that in building up complex phosphate relays using protein domains with strong functional homology from different organisms (yeast, bacteria, and plants), the best fusion points for preserving functionality are unexpectedly within the domains at homologous sequences that are involved in the actual function of the domain. An example of such a fusion is the TRZ-AHK4 fusion, which has been adapted for plant gene expression and targeted to the cell membrane. The fusion is within the G2 (GLGL/I) box in the hATPase domain of the histidine kinase. Fusions at the end of the domains did not function properly.

One of the bacterial histidine kinases that is capable of phosphorylating PhoB and OmpR is TAZ. TAZ is a previously characterized hybrid of two types of bacterial kinases. It has an aspartate receptor from the chemotactic receptor Tar in the extracellular space fused to the EnvZ component inside the membrane. The gene fusion is at an Nde site at the end of the Tar HAMP domain. TAZ sends a signal dependent phospho-relay to PhoB, and PhoB (and PhoB:GFP fusion) upon receiving a signal, shuttled to the nucleus in a signal-dependent manner. TAZ function in plant cells using nuclear shuttling of PhoB:GFP was used as an assay. It is known that plant histidine kinases are known to function in bacteria and hence as shown herein, bacterial histidine kinases can function in plants and that the transmembrane activation mechanisms are conserved.

Bacteria-plant Hybrid:

One way for getting the computationally designed receptors to work in plants is forming a bacteria-plant hybrid molecule at some point in the signal transduction pathway. One powerful aspect of the two-component systems used here is that they provide a molecular foundry for quickly testing constructs' function in bacteria and then transferring the functional components into plants (with the appropriate plant leaders and expression components added). It has been shown that plant histidine kinases could activate bacterial signal transduction pathways causing the signal-dependent production of the reporter gene β-gal. Multiple fusions of bacterial and plant histidine kinases were studied. Aiding this process was a modular foundry where the fusion could be rapidly tested in bacteria and a plant leader added and the same fusion tested in plants.

The bacterial histidine kinase TRZ, a known functional hybrid between TRG (which binds the periplasmic binding protein RBP) and the histidine kinase EnvZ (which signals to the response regulator OmpR), was used to form a fusion with the plant histidine kinase AHK4 (At2g01830). In plants, AHK4 signals via a phospho-relay to the plant AHPs. The phosphorylated plant AHP moves into the nucleus and activates expression of nuclear localized transcription factors, called type B ARRs. Type B ARRs activate transcription of cytokinin responsive genes including the type A ARRs. One of the ARRs that AHK4 activates is ARR5. Plants containing the ARR5 promoter fused to the plant reporter genes GFP and GUS were described in Romanov et al. (2002). In addition, the ARR7 promoter can also be used to regulate GFP expression in transgenic plant cells. However, the promoter for any type A ARR would also work.

The functional bacteria:plant HK was produced by a fusion at the G2 domain of the histidine kinase ATPase. The G2 domain is common to both TRZ and AHK4. The fusion essentially adds the receiver domain of AHK4 to the bacterial histidine kinase, in effect, synthetically evolving the bacterial histidine kinase 'upward' to a plant histidine kinase (FIG. 2). The bacteria:plant hybrid histidine kinase was found functional in bacteria. To determine if the bacteria:plant hybrid histidine also functioned in plants GUS/GFP expression was monitored from either the ARR5 or ARR7 promoters. Hybrid histidine kinases found to be functional in bacteria were modified for proper expression in plants using a plasmid construct containing the NOS promoter:plant leader (FLS): hybrid-HK:NOS terminator (NOS 3'). In addition, the test plasmid also contained a construct called ssTNT. See SEQ ID NO:7. This is the secretory construct shown to target periplasmic binding proteins to outside the plant when fused to the designed TNT receptor.

A "synthetic" signal transduction pathway was constructed. It was determined that the bacterial response regulators (PhoB, and to a lesser extent OmpR) moved into a plant nucleus in a signal dependent manner. PhoB was the response regulator of choice because of its strong signal-dependent nuclear localization and because it is well characterized in bacterial systems.

Bacteria, yeast, and plants can sense aspects of their environment through conserved, two-component or histidine kinase (HK) signal transduction systems. The protein components of these systems are typically comprised of multiple, relatively modular domains, arranged in various combinations and compositions. These domains tend to be conserved across pathways and species. Transfer of phosphates between components can exhibit a considerable amount of cross-talk, establishing networks that integrate multiple signals, rather than linear pathways that link a single stimulus to a response. Sequence conservation and cross-talk was determined to be extended across kingdoms and therefore used to establish a synthetic signal transduction system in a plant. The cross-talk between HK systems was utilized and the bacterial response regulators, PhoB and OmpR, were adapted for plant function. In response to cytokinin-mediated HK signaling, these bacterial proteins shuttled to the plant nucleus.

PhoB shuttling to the plant nucleus is not simple diffusion; some type of active transport is required. Nuclear pores in plant cells exclude molecules larger than 60 KD. One possibility for the observed signal-dependent shuttling of PhoB is that it is simply an increased accumulation in the nucleus. For example, PhoB is a small protein and could freely diffuse in and out of the nucleus. Upon phosphorylation, PhoB's affinity for DNA could cause it to non-specifically bind a plant DNA. To test this, a PhoB:GFP:GUS fusion where the predicted protein is 120 KD was produced. This allowed for testing whether PhoB freely diffuses or whether it is transported. A GUS reporter (β-glucuronidase) was fused at the C-terminus of PhoB:GFP. The protein fusion constructs were transformed into *Arabidopsis* plants, always selecting plants with a single T-DNA insert and then movement of the PhoB:GFP:GUS fusion protein into the nucleus in a signal-dependent manner was monitored. Prior to cytokinin treatment, PhoB:GFP:GUS was found diffused throughout the cells with some weak accumulation in the nuclei. The weak nuclear accumulation may be due to endogenous histidine kinase signaling coupled with the inability of the PHoB:GFP:GUS protein to leave the nucleus. However, after cytokinin treatment PhoB:GFP:GUS nuclear accumulation was significantly enhanced. These data indicate that the nuclear translocation of PhoB and OmpR cannot be explained by diffusion, indicating that they are transported into the nucleus and that plant factor(s) unexpectedly recognize conserved regions of these bacterial response regulators.

Cytokinin induced PhoB movement to the nucleus does require aspartate used in bacterial signaling. Two component signaling pathways involve His→Asp phosphor-relays. In bacteria, the PhoB response regulator is normally phosphorylated at an Asp residue (D53). It was then determined if this critical Asp is also used in planta. In plants, transmembrane histidine kinases autophosphorylate at a His residue and then transfer the phosphate to an Asp residue within the protein. Normally, the phosphate is then transferred to a His on the histidine phosphotransferase proteins, AHPs.

The nuclear shuttling unexpectedly requires the bacterial conserved phosphor-accepting Asp residue. Because of this discovery, PhoB's DNA biding and transactivation properties were used and adapted to function in plants, in combination with a synthetic, PhoB-responsive, promoter (PlantPho). In response to a cytokinin signal the adaptive protein, PhoB:VP64, shuttles to the nucleus, binds Plant:Pho and activates expression of the β-glucuronidase reporter gene. These observations show that adaptive horizontal gene transfer can be used to produce synthetic eukaryotic signal transduction pathways.

Figure 3E:
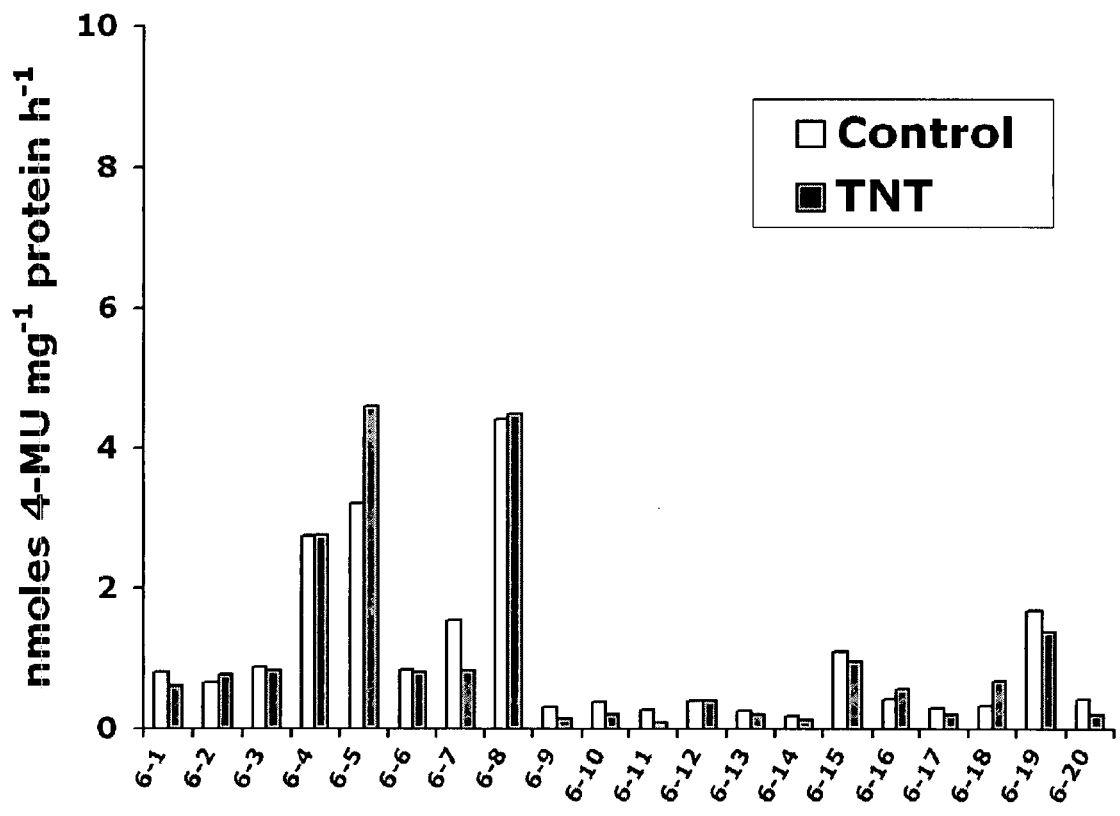
Figure 3E:
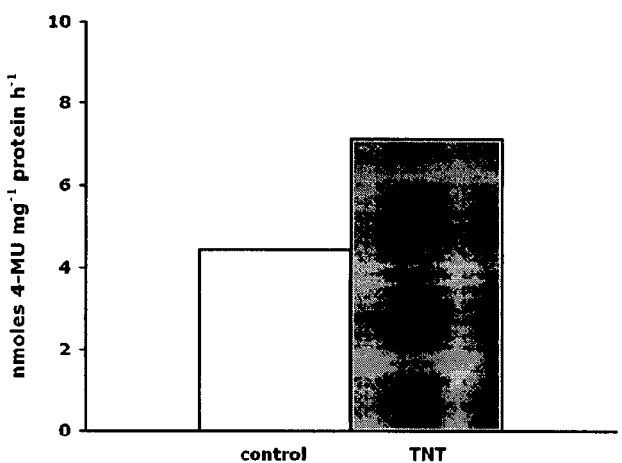
Figure 4A:
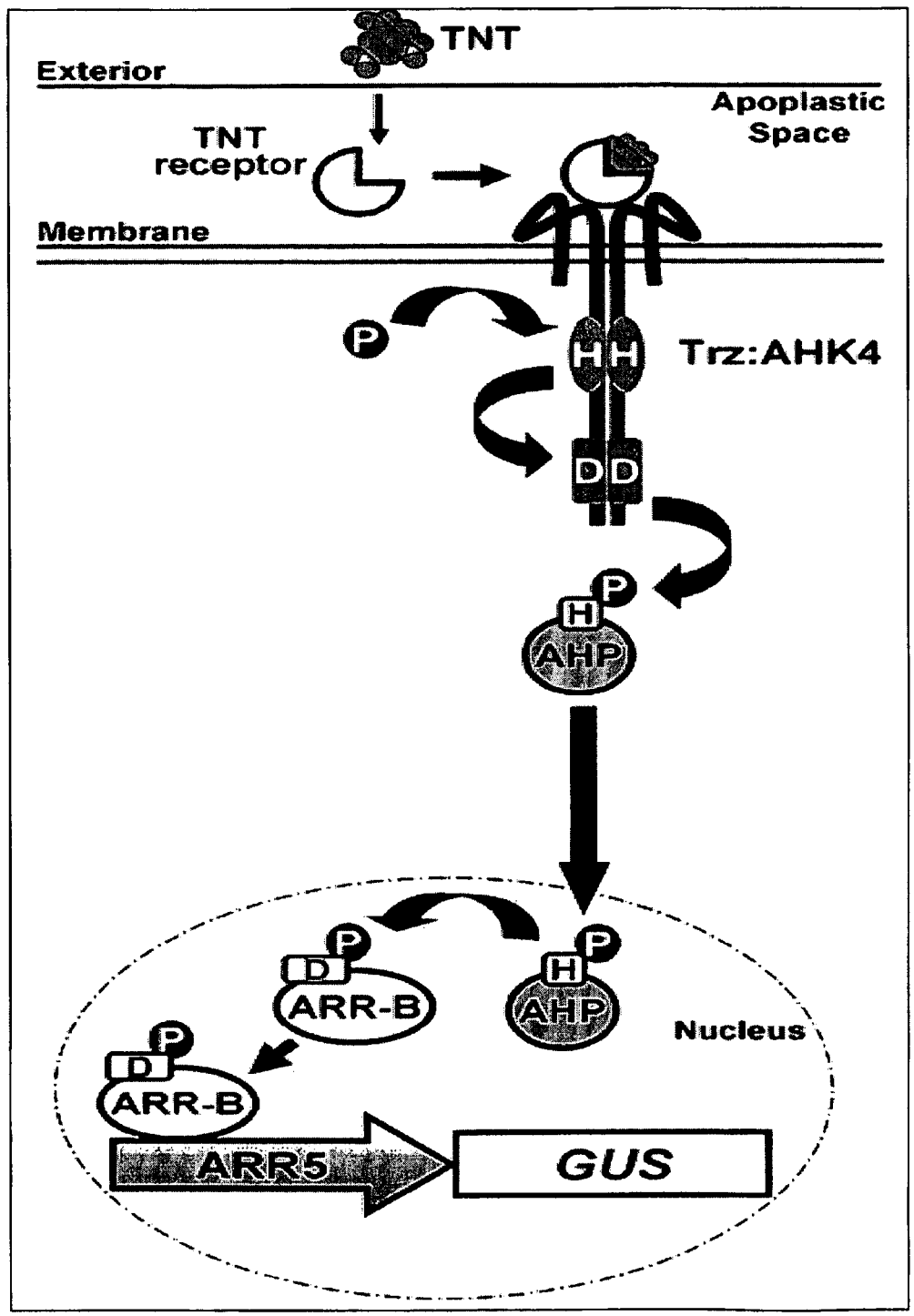
FIGS. 4A-4D show data for function of computationally designed receptors and hybrid histidine kinases in plants as measured by GUS activity.
Figure 4A:
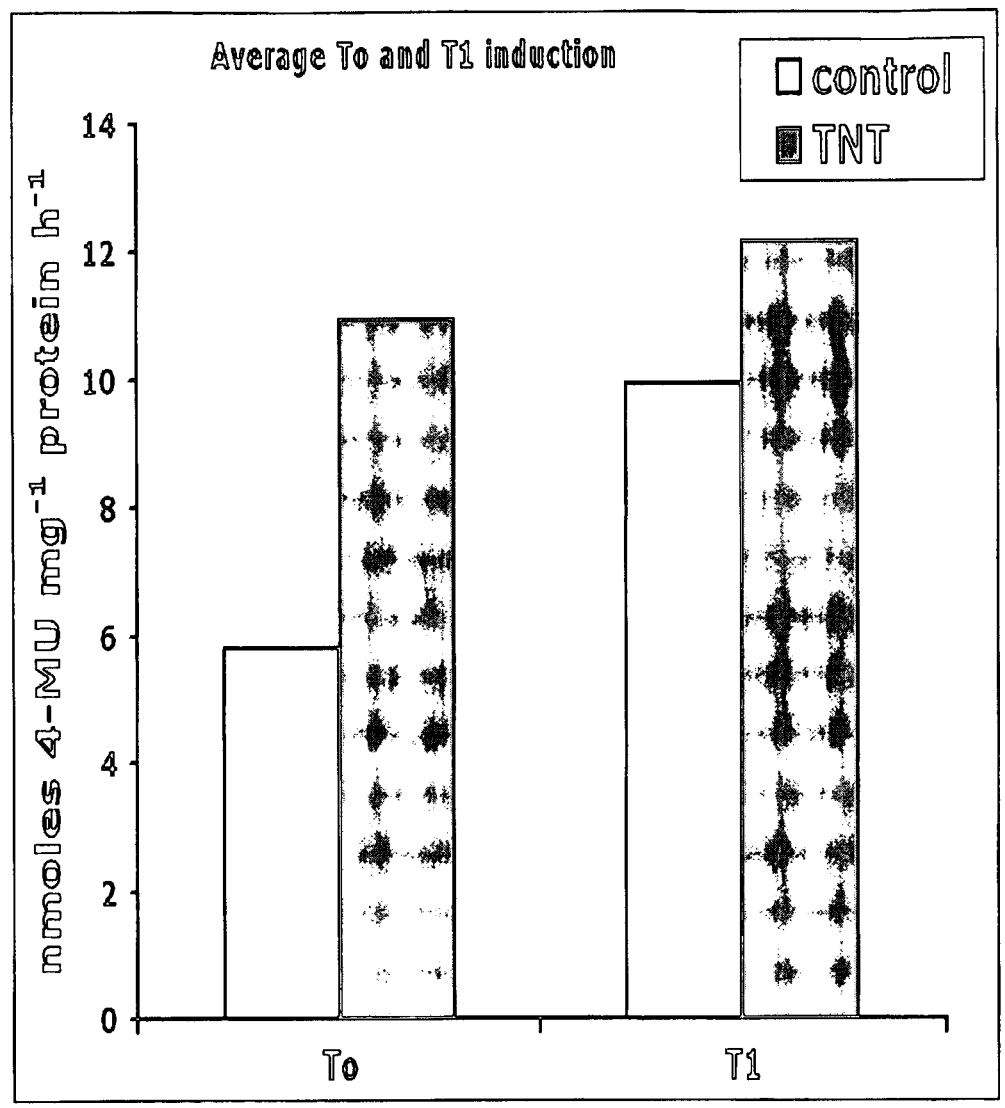
Figure 4B:
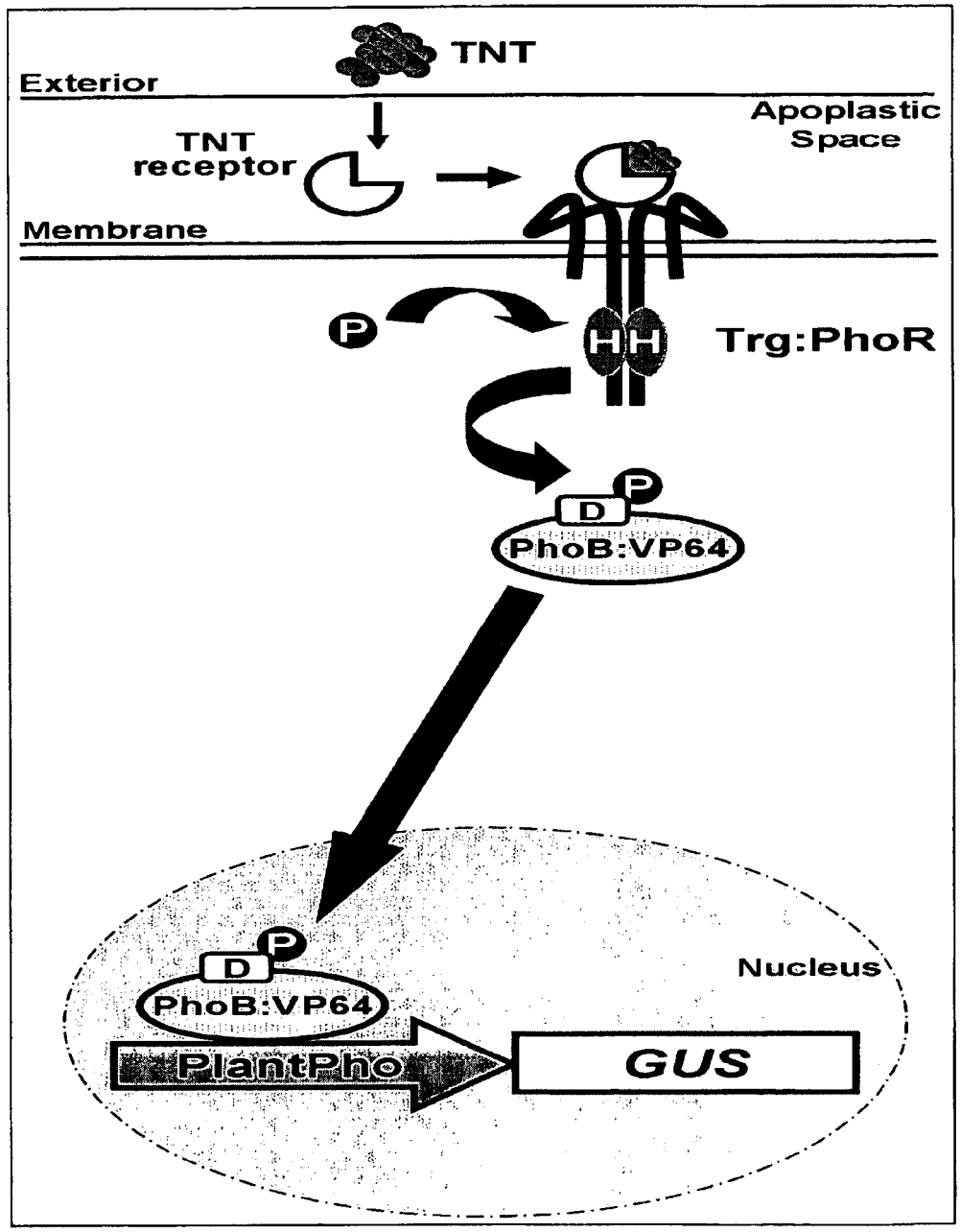
Figure 4B:
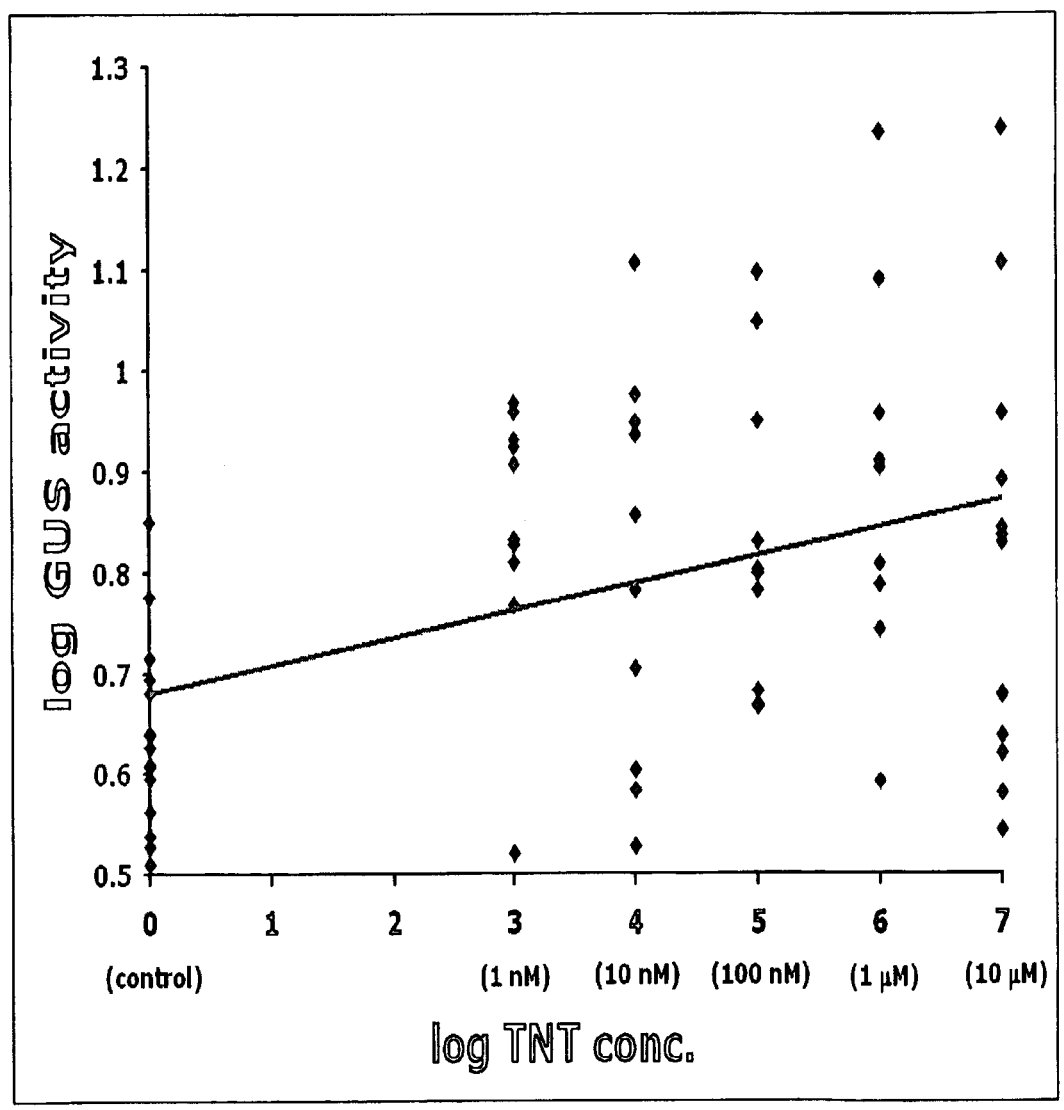
Figure 4C:
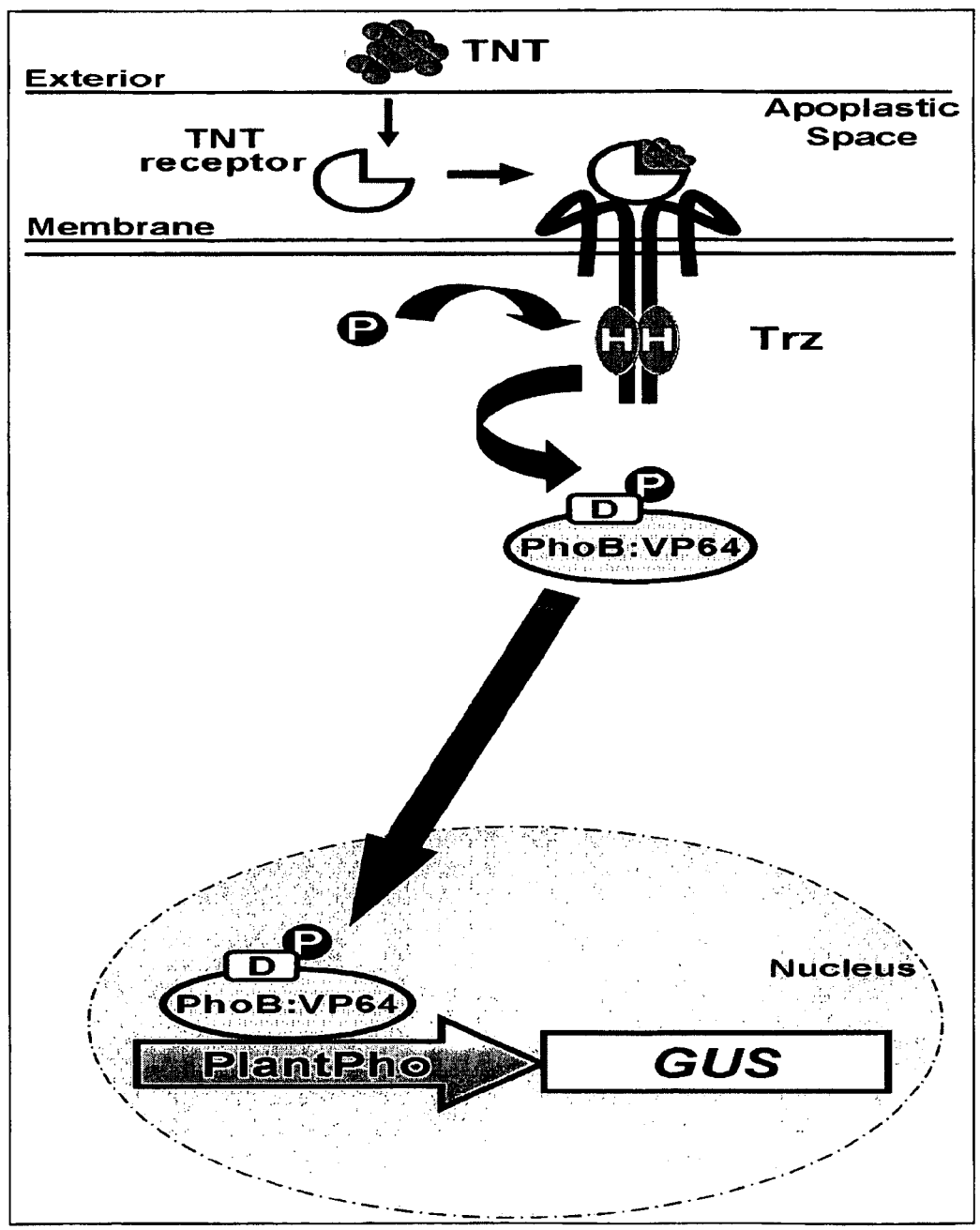
Figure 4C:
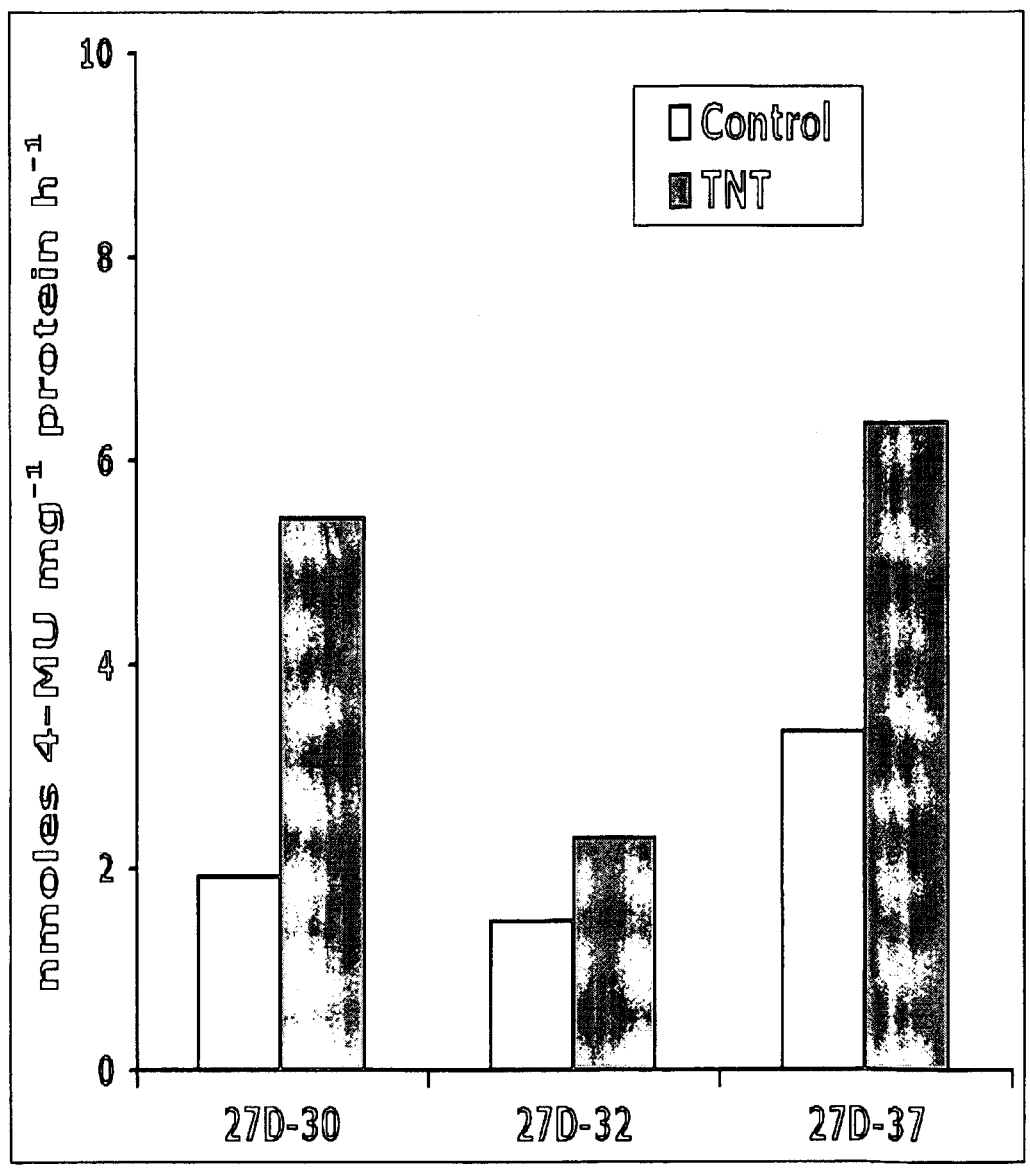
Figure 4D:
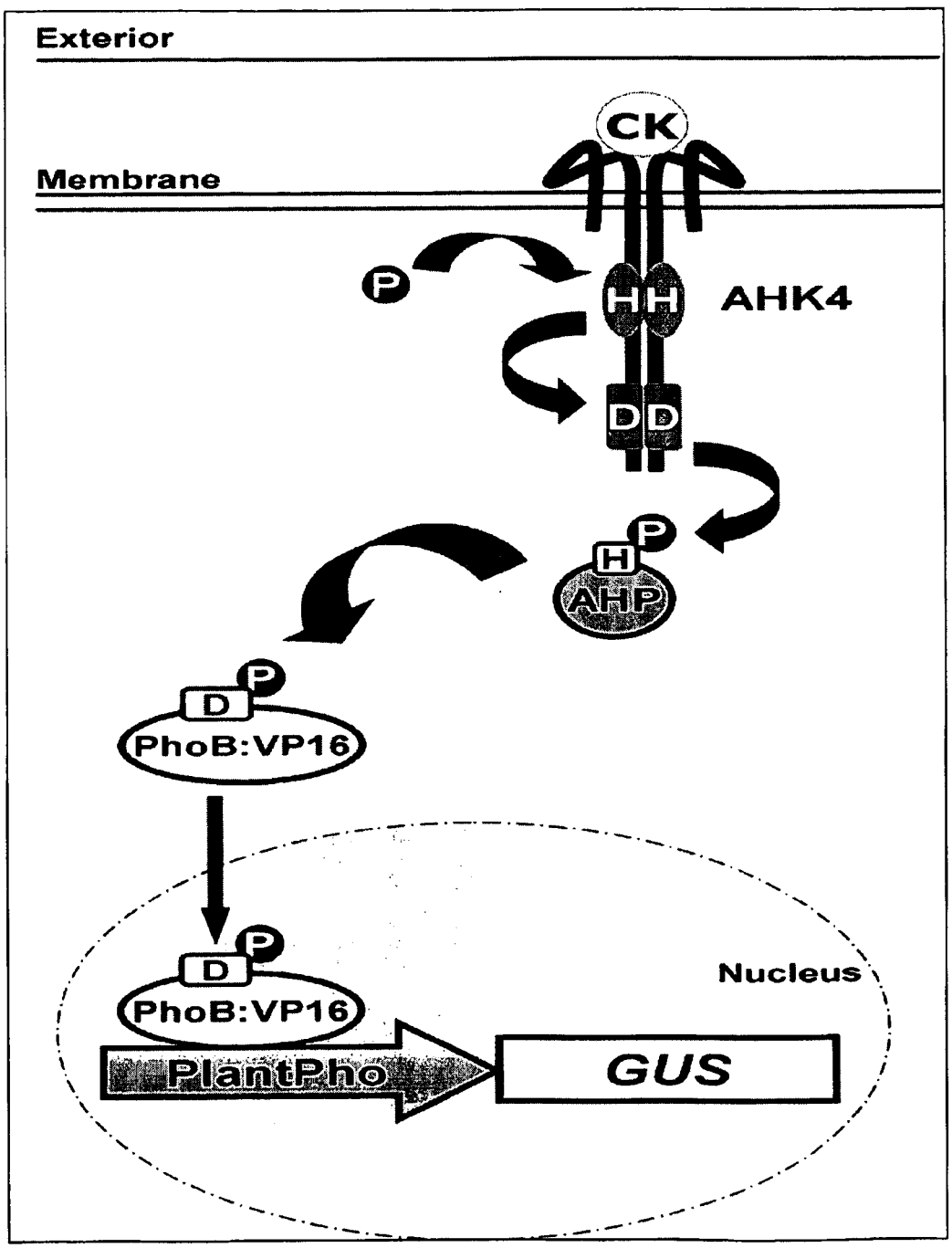
Figure 4D:
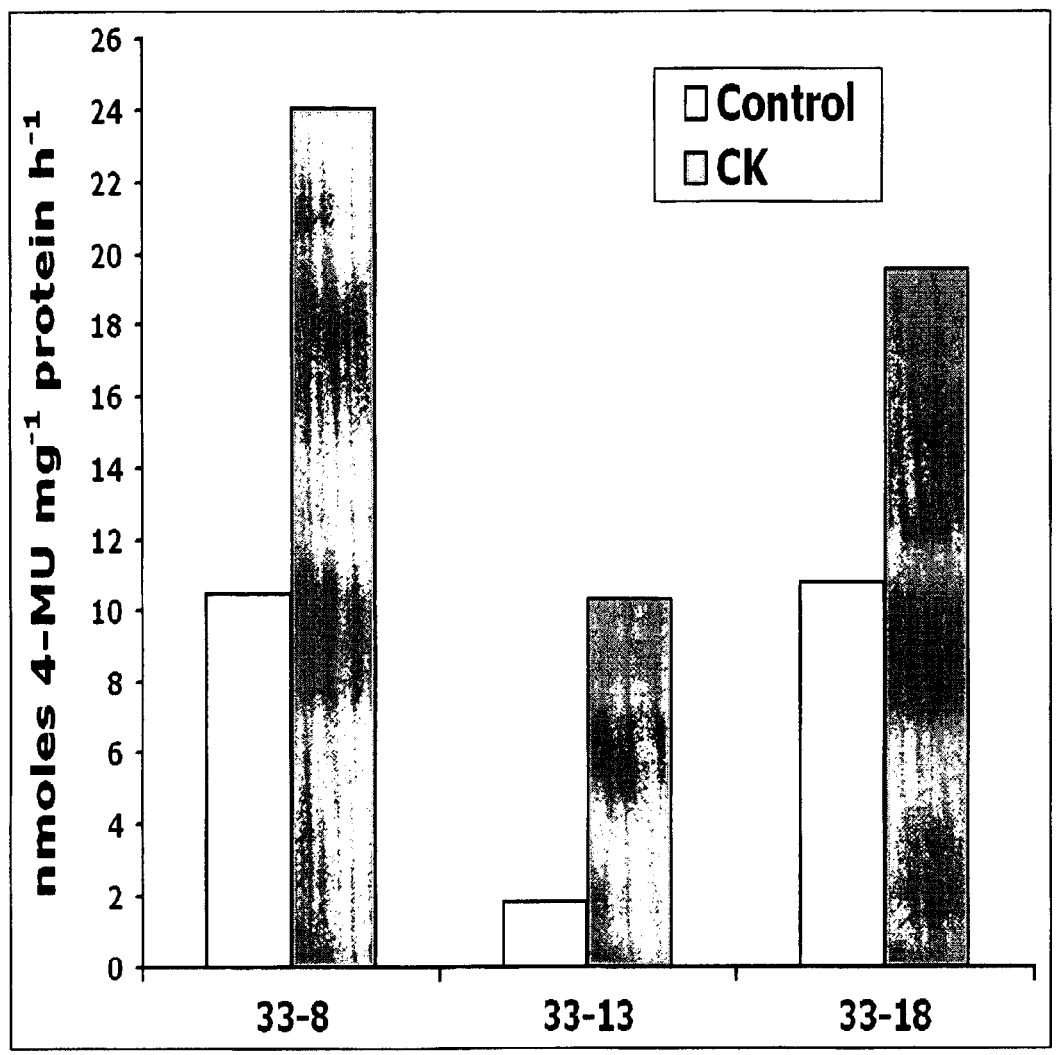

The D53 in PhoB, that is fused with GFP, was mutagenized (Asp 53 to Ala), the DNA sequence verified, and then transferred into *Arabidopsis* plants (FIG. 3D). PhoB$^{D53A}$:GFP was assayed for function in plants by activating the histidine kinase signaling pathway with cytokinin. In most cells PhoB$^{D53A}$:GFP did not accumulate in the nucleus in response to the cytokinin signal (FIG. 3D). There was some accumulation in cells of the vascular tissues. However, these cells accumulate some PhoB:GFP without an exogenous signal (FIG. 3A) and it is possible that the bacteria response regulator in plants uses residues in addition to the D53 for shuttling. Like PhoB, mutagenesis of the bacterial conserved aspartate in OmpR also disrupts nuclear shuttling. FIG. 3D shows that OmpR$^{D55A}$:GFP did not show nuclear localization in response to the exogenous cytokinin signal. For PhoB, it was also shown that the Asp53 residue is important in quantitative GUS assays with the TNT sensor protein and hybrid HKs described below. FIGS. 3D and 3E show that background (control) levels of TNT induction were close to 4 nM MU/mg protein/hour whereas induced levels are consistently at 6 nM MU/mg protein/hour or better (FIG. 3D). FIG. 3E shows that in plants containing PhoBD53A:VP64 signaling to activate expression of GUS, levels are significantly less than 4 and only one plant (out of twenty) had levels approaching that of the control.

These observations show that adaptive horizontal gene transfer can be used to produce synthetic eukaryotic signal transduction pathways. PhoB, upon phosphorylation, has both DNA binding and transcriptional activation capabilities via its binding to "Pho Boxes" in the promoter region of phosphate-responsive genes in the Pho regulon (VanBogelen et al. 1996). The crystal structure of bound PhoB (Blanco et al. 2002) showed that PhoB binds to a Pho Box as a homodimer as well as to multiple Pho boxes in tandem. In the non-phosphorylated form, PhoB's receiver domain functions as a repressor, preventing the DNA binding/transactivation domain from functioning.

Although PhoB has both DNA binding and transcriptional activation functions, the differences between prokaryotic and eukaryotic transcriptional activation are considerable. Without wishing to be bound by theory, it is believed that the PhoB transcriptional activation function would not work in a plant; therefore, the VP64 transcriptional activator was added to the C-terminal end of PhoB as a translational fusion. The PhoB DNA binding and transcriptional activation activities overlap in the bacterial protein and hence we did not believe they could be easily separated. VP64 is a transcriptional activator domain consisting of four copies of the well-characterized VP16 activation domain (Triezenberg et al. 1988 Genes Dev. 2:730-742; Triezenberg et al. (1988) ibid. 71-8-729), and was added to the C-terminal region of PhoB to create a synthetic protein PhoB:VP64. This synthetic protein was engineered to be expressed in plants with a strong constitutive promoter (FMV, figwort mosaic virus promoter) and a common 3' termination signal. A nopaline synthase (Nos) transcription termination sequence was added at the 3' end of the chimeric gene. The DNA binding consensus sequence for PhoB is CTGTCATAYAYCTGTCACAYYN (SEQ ID NO:14).

Other possibilities for the Response Regulator Protein:

Response regulator proteins are modular with a receiver domain that is phosphorylated and an effector domain which has DNA binding activity. These two domains are joined by a linker region, which varies among different response regulators. These linkers have been shown to be important for proper activity in bacteria (Walthers et al., 2003). A fusion of a receiver domain linker region (which includes but is not limited to OmpR's receiver domain linker region) with an effector domain (which includes but is not limited to PhoB's effector domain, which essentially has the DNA binding activity to the PlantPho promoter) is made. It is expected that OmpR's receiver domain will be phosphorylated more efficiently (when compared to PhoB) by Trz. It is assumed that OmpR's receiver domain will still be able to interact with PhoB's effector domain and the protein will shuttle to the nucleus and bind the PlantPho promoter.

In another example, specific amino acids will be modified in a receiver domain (which includes but is not limited to PhoB) to enable the receiver domain to interact more effectively with Trz. These amino acid modifications include, but are not limited to, T103P and S107N. The amino acids that are modified include, but are not limited to, amino acids that are responsible for the specificity of the interaction between the response regulators and their respective histidine kinases (which include, but are not limited to PhoR and EnvZ) (Li et al 2003). Once the amino acids have been modified, transgenic plants are generated that contain a target substance of interest receptor (which includes, but is not limited to ssTNT), a histidine kinase (which includes, but is not limited to FLS-Trz), a response regulator with a modified receiver domain (which includes, but is not limited to $PhoB^{T103P,S107N}$:VP64) and a PlantPho promoter (which includes, but is not limited to PlantPho:Gus). It is expected that by modifying specific amino acids in PhoB (or any other receiver domain) to amino acids found in a cognate receiver domain (such as OmpR), the interaction of the new receiver domain with Trz will be improved.

Because of the high amount of evolutionary conservation of the response regulators and histidine kinases in bacteria, fungi, cyanobacteria and plants, other response regulators and functional histidine kinases will also work. The response regulators and the histidine kinases can be the cognate components from a specific system and/or functional components that transmit a phospho-relay in plants.

PlantPho Promoter:

The PlantPho promoter was designed to allow for signal dependent PhoB transcriptional activation in plants. The DNA binding consensus sequence for PhoB is CTGTCAT-AYAYCTGTCACAYYN (SEQ ID NO:14). Eight tandem PhoB binding sequences (TGTCA) were linked to a plant transcription start site, the −46 region from the CaMV 35S promoter. The PhoB boxes and −46 promoter, collectively constitute the "PlantPho promoter" (SEQ ID NO:1).

To prove this functions, the synthetic PlantPho promoter was placed upstream of and operably linked to various genes. These various genes include laboratory reporter genes such as the Green Fluorescent Protein (GFP) or β-glucuronidase (GUS), or the wide scale readout reporter genes and constructs of the degreening circuit. It could also include other genes involved in the induction of a specific process such as flowering or production of a metabolic or pharmaceutical compound. These genes are cloned together with the FMV::PhoB-VP64-Nos construct into a plant transformation vector. Transgenic *Arabidopsis* plants with one simple insert were obtained. In the sentinel plant this promoter is operably linked to at least one chlorophyll degradation enzyme coding sequence, and also desirably to an antisense or diRNA determining region for inhibiting expression of a chlorophyll biosynthetic enzyme.

In the sentinel plants of the present invention, the PhoB:VP64 moves into the nucleus in response to the binding of the target substance to the sensor portion (or ligand binding domain) on the exterior of the cell. In a model system, we looked for PhoB:VP64 to bind to the PlantPho promoter and activate GUS or GFP expression. Plants were incubated for approximately 16 h in the presence or in the absence of the ligand, of 0.5 μM t-zeatin (a cytokinin). −Cytokinin-dependent induction of GUS expression of up to 7.8-fold was observed. The data indicated that PhoB:VP64 (synthetic response regulator designed from bacterial components and with eukaryotic transcriptional activator) could direct external signal-dependent expression from the synthetic PlantPho promoter.

The cytokinin dependent induction showed that the signaling components worked and that horizontal gene transfer can be used to produce artificial signal transduction pathways in higher eukaryotic organisms. To link this synthetic signal transduction pathway with input from the computationally designed receptors, the extracellular targeted sensor protein was added (FIG. 1) and separately, the various hybrid histidine kinases shown in FIG. 2. To prove this system functions, perception of the target substance (TNT) was linked to quantitative expression of the GUS reporter gene.

FIG. 4A-C show that three separate signaling systems all function in transgenic plants to report the presence of the TNT ligand. In FIG. 4A, plants are exposed to TNT, TNT binds the sensor protein, the sensor protein develops affinity for the exterior of the histidine kinase (Trg), the histidine kinase is activated, and the operably linked interior AHK4 transmits a high energy phosphate group to AHPs, that then shuttles to the nucleus and activates transcription of a Type B ARR gene (such as ARR5).

In FIG. 4B, plants are exposed to TNT, TNT binds the sensor protein, the sensor protein develops affinity for the exterior of the histidine kinase (Trg), the histidine kinase is activated, and the operably linked interior (PhoR) transmits a high energy phosphate group to PhoB:VP64 that then shuttles to the nucleus and activates transcription of the PlantPho promoter linked to GUS. FIG. 4B also shows detailed statistical data (ANOVA) indicating that the data are significant. All assumptions for this analysis were tested and met. In addition, FIG. 4B shows that the system is responding to extremely low levels, 10 picomoles, of TNT.

In FIG. 4C, plants are exposed to TNT, TNT binds the sensor protein, the sensor protein develops affinity for the exterior of the histidine kinase (Trg), the histidine kinase is activated, and the operably linked interior (EnvZ) transmits a high energy phosphate group to PhoB:VP64 that then shuttles to the nucleus and activates transcription on the PlantPho promoter linked to GUS.

In FIG. 4D, the eukaryotic activation domain (VP64) is replaced with a smaller version, VP16. Cytokinin induction or cross kingdom signaling (with cytokinin induction) shows that other eukaryotic activation domains can also work in addition to VP64. GUS induction is somewhat better with VP16 than VP64.

Shuttling Protein/Response Regulator:

Hybrid histidine kinases containing both bacterial and plant segments were unexpectedly shown to be functional in both bacteria and plants. This discovery is important because all hybrid histidine kinases to date are ones made from portions of similar bacterial histidine kinases. In addition, it provides a molecular foundry to rapidly move genes between bacteria and plants, opening the door for directed evolution approaches.

In a specific example, a hybrid was created between the bacterial periplasmic histidine kinase (TRZ) and the plant histidine kinase (AHK4) normally found within the plant cell membrane. Hence, when the hybrid histidine kinase is activated by binding of a ligand bound receptor, the signal is transmitted via a phosphor-relay to an AHP via phosphorelay that moves into the nucleus and activates transcription (ARR5 or ARR7 promoter).

Quantitative (GUS) and qualitative (GFP) data were obtained for transgenic Arabidopsis plants homozygous for the ARR5 promoter fused to GUS and GFP, respectively, retransformed with the computationally designed receptor for TNT (SS:TNT) and the hybrid histidine kinase (plant leader (FLS):TRZ:AHK4). In response to TNT, the ARR5 promoter was activated causing an approximate 2-fold increase in GUS expression.

Components of the pathway were separately deleted. When the histidine kinase was deleted, no induction was seen and when the TNT receptor was deleted, no induction was observed. Our experimental data show that we can build a synthetic signal transduction that functions in plants from bacterial and designed components. The pathway shown to function is FLS:TRZ:AHK4→AHP→type B ARR→type A ARR promoter.

TRG:

The coding sequence of the TRG receptor (exterior) with EnvZ (interior) is assembled via molecular biological techniques (Baumgartner J M, et al., 1994). The EnvZ on the membrane interior sends a phospho-relay to its cognate response regulator OmpR and also to PhoB. The bacterial response regulator PhoB's cognate histidine kinase is PhoR. Two functional fusions of TRG (exterior) to PhoR interior have been made and shown to function in bacterial cells (SEQ ID NO:2, SEQ ID NO:3 and SEQ ID NO:12). They were then incorporated in a complete signaling pathway (with the designed receptors) in plants. The complete signaling pathway in this case is: SS-TNT→FLS:TRG:PhoR→PhoB: VP64→PlantPho promoter:GFP or PlantPho promoter:GUS.

The sensing by the computationally designed receptor for TNT occurs when SS-TNT binds TNT, then develops high affinity for and binds Trg. Binding Trg activates the histidine kinase to start a phospho-relay system to PhoB:VP64. Upon phosphorylation, PhoB:VP64 moves into the nucleus, where it binds to the synthetic PlantPho promoter and activates transcription of the GFP or GUS gene in the demonstration project, and the degreening circuit in the sentinel plants of the present invention. It could also activate expression of any type of plant response gene typical for plant biotechnology such as those involved in flowering or those involved in initiating a metabolic or pharmaceutical pathway. In the degreening circuit, the synthetic PlantPho promoter is operably linked to the coding sequence of a chlorophyll degradation enzyme such as chlorophyllase, and desirably a synthetic PlantPho promoter is also operably linked to sequences encoding antisense or small interfering RNA specific to at least one chlorophyll biosynthetic enzyme.

T0 represents the first generation of transgenic plants whereas T1 represents the second generation (T0 seed self-pollinated). Seed from two of the T0 parental lines has been obtained. These lines segregate for the two T-DNA inserts that contain the signaling components. One T-DNA contains the genes for the receptor and histidine kinase (SS-TNT, FLS: Trg:PhoR) while the other T-DNA contains the genes for the response regulator (PhoB:VP64) and the PlantPho promoter fused to GUS (PlantPho:GUS). In bacterial sensing and signaling systems, the sensitivity and response systems are extremely sensitive to the other's levels. In the transgenic plants, the two genetic sets segregate in a classic 9:3:3:1 pattern.

It is possible to substantially improve the sensing and signaling systems by modulating the expression levels of receptor/HK and signaling components (PhoB:VP64, PlantPho promoter) via expression controls (promoter, translational enhancer etc.) and via copy number. Microarray data from the degreening circuit indicate the response required an eight-fold increase in the expression levels of the degreening circuit genes' expression levels. The data from FIG. 4 shows that there is about a two-fold increase in expression with sensing TNT in model plants. The degreening system is linked to the Pho (synthetic) sensing system (the sentinel plants) and provides similar sensitivity to the target substance for which the specific binding site is engineered into the sensing portion of the input circuit. Specifically, the 10XN1 Plant promoter driving the degreening circuit genes is replaced by the synthetic Pho promoter. Because the system is modular, the TNT receptor can be replaced with any designed specific receptor site for a target substance of interest. It is important to note that the sensing system has been shown to work with two independent signaling systems. The designed receptors provide an extremely high level of sensitivity (nanomolar) and extremely high specificity, as demonstrated in the bacterial system (Looger et al., 2003)

Protochlorophyllide oxidoreductase (POR) is the key enzyme in chlorophyll biosynthesis (Malkin and Niyogi, 2000). Arabidopsis contains three genes for POR (Oosawa et al., 2000; Pattanayak and Tripathy, 2002). To block expression of all three AtPOR (Arabidopsis thaliana POR) genes, a diRNA construct to a region conserved in each of the genes was produced. A conserved region of approximately 500 bp was identified located from nucleotides 700-1200 within the AtPOR 1708 bp cDNA that is conserved in all three genes. Standard PCR methods were used to amplify this conserved region from a full-length cDNA (AT1G03630). To facilitate cloning, forward and reverse primers with restriction sites were used for AscI and BamH1 in the forward primer and SwaI and XbaI on the reverse primer. The target DNA in POR genes lacks the sites for these restriction endonucleases. The conserved region of the POR gene was amplified and its sequence was verified by sequencing. The PCR product was then digested with AscI and SwaI and ligated to AscI-SwaI-cleaved dsRNA vector. Subsequently, the PCR product was digested with BamH1 and XbaI and ligated into flanking sequences of the vector to produce a construct that will express an inverted repeat of the conserved region of the POR genes. By doing so, expression from all three POR genes can be silenced by the dsRNA produced.

Chlorophyllase:

The complete chlorophyll degradation pathway is known to the art. To produce the degreening circuit, two key genes in this pathway were induced. One of the key enzymes involved in chlorophyll breakdown is chlorophyllase (Matile et al., 1999; Tsuchiya et al., 1999; Benedetti and Arruda, 2002). Constitutive expression of the chlorophyllase gene (At-COR1) leads to a massive accumulation of the breakdown product chlorophyllide (Benedetti and Arruda, 2002). Because the chlorophyllide product still has a green color (light green for chlorophyllide versus dark green for chlorophyll), a second gene was included to further degrade the breakdown product. The next gene in the chlorophyll breakdown pathway is magnesium dechelatase that removes the Mg from the four-ring structure. Action of this enzyme leads to formation of pheophorbide a, a molecule that still retains some of the green color (Dangl et al., 2000). Because of this, one of the two enzymes involved in opening the ring structure was used to eliminate the remaining green color. In chlorophyll breakdown, ring opening occurs by the joint action of pheophorbide a oxygenase (PAO) and red chlorophyll catabolites reductase (RCC reductase) (Matile et al., 1999). Intracellularly, PAO and RCC reductase are thought to be juxtaposed with PAO located on the inner membrane of the chloroplast envelope and RCC reductase located just inside in the stroma (Matile et al., 1999). While the *Arabidopsis* genome contains several candidates for PAO, biochemical proof that these genes encode PAO is lacking. In contrast, the *Arabidopsis* RCC reductase gene has been isolated and characterized (Wuthrich et al., 2000; Mach et al., 2001). Therefore, RCC reductase was used in the present work. Both the chlorophyllase gene (AtCOR1) and RCC reductase (NCBI Accession No. Z99707) can be placed under control of promoters that induce expression in response to input from either cytoplasmic or extracellular analytes.

Rapid degreening requires the inhibition of chlorophyll synthesis concurrent with the induction of degradation. Accordingly, we first assembled each function separately under control of the signal-responsive transcriptionally inducible system. Two means to inhibit net chlorophyll synthesis ("stop synthesis" circuits) were used: directly, through its biosynthetic pathway; or indirectly, through a precursor/trafficking pathway. The rate-limiting enzyme in chlorophyll biosynthesis is NADPH:protochlorophyllide oxidoreductase. In *Arabidopsis* this enzyme is encoded by three POR genes (PORA, PORB, PORC) (Frick et al., 2003; Masuda et al., 2003; Oosawa et al., 2000). POR is a light-dependent enzyme that catalyzes the conversion of protochlorophyllide a (Proto) to chlorophyllide a. GUN4, Genomes Uncoupled 4, is a single copy gene that functions in regulating chlorophyll biosynthesis, precursors trafficking, and may have a role in photoprotection (Larkin et al., 2003; Verdecia et al., 2005). GUN4 has been shown to bind and activate Mg-chelatase, an enzyme complex that produces Mg-protoporphyrin IX (MgProto). A diRNA construct was prepared to a conserved POR gene region, its expression placed under control of a signal-dependent inducible promoter, and the construct introduced into *Arabidopsis* plants. A diRNA construct to GUN4 was also prepared, and likewise placed under control of the inducible promoter. A signal-dependent induction of the diRNA to POR or GUN4 alone did not cause plants to lose their green color.

Genes encoding key enzymes in chlorophyll breakdown have also been identified (Eckhardt et al., 2004). Chlorophyll breakdown involves a series of enzymatic steps, with key processes being hydrophobic tail removal by chlorophyllase (CHLASE) (Benedetti and Arruda, 2002; Tsuchiya et al., 1999), porphyrin ring cleavage by PAO (pheide a oxygenase) and subsequent action of RCCR (red chlorophyll catabolite reductase) (Pruzinska et al., 2003; Pruzinska et al., 2005; Wuthrich et al., 2000). Two distinct gene circuits designed to initiate chlorophyll degradation were assembled ("initiate breakdown" circuits), containing CHLASE and either PAO or RCCR under control of the signal-dependent promoter. Even after 48 hours of induction of the chlorophyll "initiate breakdown" the plants also remained green, despite the over-expression of the two major genes involved in chlorophyll metabolism. These results are consistent with our hypothesis that plants are able to partially compensate for changes in chlorophyll levels by regulating overall metabolism.

"Stop-synthesis" constructs with the "initiate breakdown" genes were combined in one T-DNA to test if a rapid, regulated chlorophyll loss system could be developed. The constructs/genes were brought together in various combinations to produce 5 different "degreening gene circuits" (Table 1, FIG. 5A). Each "degreening circuit" consists of an inducible diRNA to either POR or GUN4 genes, CHLASE inducible expression, combined with PAO and/or RCCR inducible expression. Degreening circuits were also obtained by crossing plants containing the separate gene circuits and produced comparable results.

TABLE 1

Genes used in constructing each of the complete degreening circuits

| Degreening Circuit # | Stop Synthesis | Initiate Breakdown |
|---|---|---|
| 1 | POR | CHLASE, RCCR |
| 2 | GUN4 | CHLASE, RCCR |
| 3 | POR | CHLASE, PAO |
| 4 | GUN4 | CHLASE, PAO |
| 5 | GUN4 | CHLASE, RCCR, PAO |

Figure 5A:
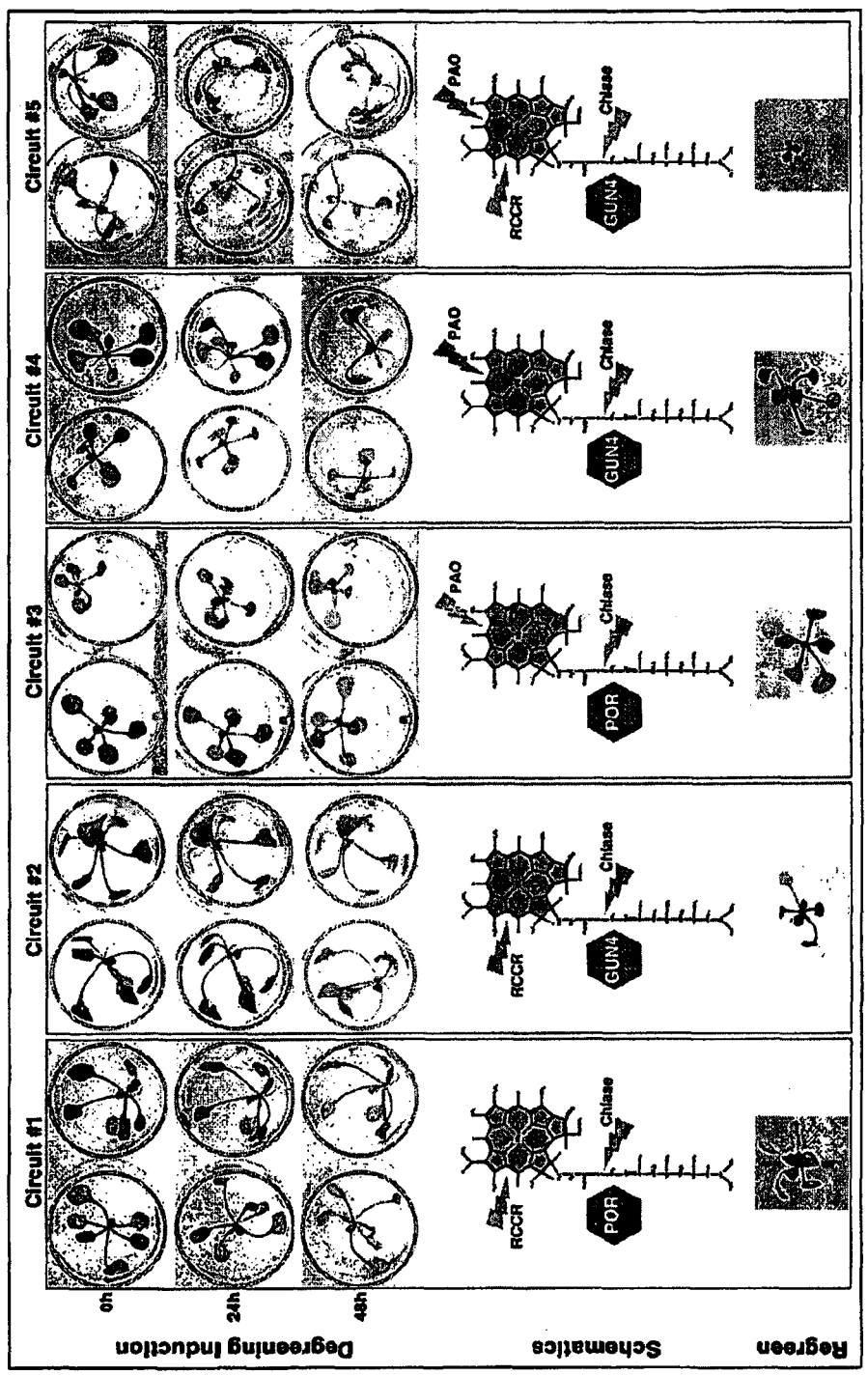
FIGS. 5A-5F show function of the degreening circuits used as output.

FIG. 5A shows that induction of the degreening circuits caused a loss of chlorophyll from all regions of the plant, with less effect early on in the shoot apex. Chlorophyll loss is extensive with plants becoming white within 24-48 hours after induction. In senescing *Arabidopsis*, loss of chlorophyll typically reveals yellow carotenoid pigments; the white phenotype observed upon induction of the synthetic degreening circuits suggests that carotenoid pigments are also lost.

A notable feature of chlorophyll loss by the degreening circuits is that the rational design of the synthetic circuit (simultaneous regulation of biosynthesis and breakdown) leads to a similar white phenotype regardless of the specific gene combination. Only a slight difference was seen between stopping synthesis with diRNA to POR and diRNA to GUN4 (compare circuit #1 to #2, or circuit #3 to #4). Inclusion of the RCCR gene with CHLASE to initiate breakdown produced slightly better chlorophyll reduction than breakdown initiation that involved PAO and CHLASE (compare circuit #1 and #2 to circuit #3 and #4). Degreening circuit #5 differs from the others as it contains the PAO and RCCR (as well as CHLASE) genes to initiate breakdown. Plants containing circuit #5 lose chlorophyll within 24 hours; however, the plants are light green prior to induction.

Figure 5B:
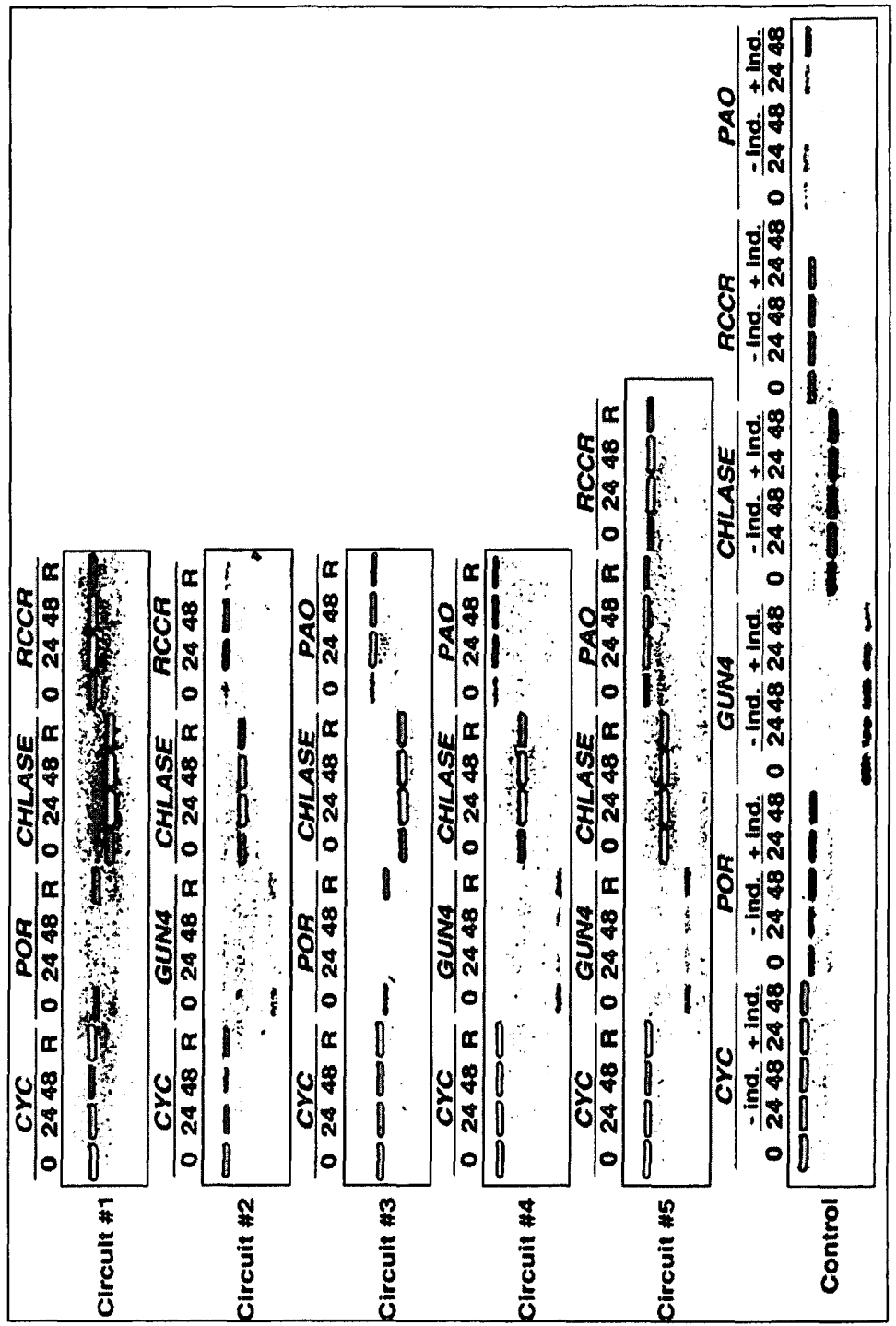

Changes in the expression of degreening circuit genes were verified with semi-quantitative RT-PCR (FIG. 5B). As predicted, induction of diRNA constructs lead to decline in the respective mRNAs: POR mRNA declined in plants with circuits #1 and #3; GUN4 mRNAs declined in circuit #2 and to a lesser extent in circuits #4 and #5. mRNAs for genes that are induced were found to dramatically increase: CHLASE and RCCR increased in plants containing circuit #1 or #2. For plants containing circuit #3 or #4, CHLASE levels increased and PAO induction showed a strong increase in circuit #3, with a more modest induction in plants containing circuit #4. Plants containing circuit #5, which were light green prior to induction, appear to have lost regulation of the CHLASE and RCCR genes. Levels of cyclophilin mRNA were used as a control and in some lines these levels declined, likely reflecting the decline in total RNA at 24 and 48 hours of induction. Consequently, the RT-PCR results likely under-estimate reductions/increases in levels of degreening circuit gene mRNAs. This is confirmed by analysis of CHLASE in circuit #3; RT-PCR results indicate a 3-fold induction, whereas microarray analysis showed it was induced >8 fold.

To determine if decreased levels of POR and GUN4 transcripts produced corresponding decrease in the proteins, Western blots using antibodies to POR and GUN4 were performed. Induction of the degreening circuits led to dramatic decrease in POR and GUN4 proteins, with levels decreasing by 70-90% within 24 hours.

Reset capacity is an essential feature both in a plant functioning as a sentinel for terrorist threats, to allow multiple or repeated threats to be detected, and as a plant environmental monitor for long-term pollutant monitoring. Attempts have been made to develop reset capacities in plant reporter genes by decreasing mRNA stability. The use of the degreening circuit as a reporter system provides an endogenous means to reset the system. Plants that had lost their chlorophyll from induction of the degreening circuit re-developed their green color or regreened after the inducer was removed (FIG. 5A, Regreen). The regreening process was enhanced with cytokinin treatment, providing a simple and readily available means to reset the reporter system. Furthermore, regreened plants can be induced to degreen again. Regreening is most apparent in rapidly expanding leaves. However, partially degreened leaves and tissues are also capable of regreening. Older leaves that completely degreened early in the process, and have lost turgor, did not regreen. In regreening plants, the levels of POR and GUN4 transcripts increased, while levels of CHLASE, PAO, and RCCR mRNAs decreased to levels approaching normal (FIG. 5B).

Because light plays an essential role in chlorophyll metabolism, we asked if light is required for degreening. Plants grown under different light intensities (50 to 350 $\mu E \cdot m^{-2} \cdot s^{-1}$) and different temperatures (14° C. to 30° C.) were not affected in their ability to degreen. However, when plants were grown under standard light conditions and induced to degreen in complete darkness, the effects of the degreening circuit were muted (FIG. 5E, part a). After 24, 48 or 72 hours of induction in complete darkness the plants eventually pale, but are still a light green, indicating that light is required for rapid chlorophyll loss. If plants induced in complete darkness were subsequently transferred to the light, degreening proceeded at an enhanced rate.

In *Arabidopsis*, detached leaves and whole plants show a distinct response to dark-induced senescence (Weaver and Amasino, 2001). Darkness is known to induce senescence in detached leaves but not in whole plants. To determine if the degreening circuit functioned similar to senescence we induced degreening in detached leaves. As expected, under standard light conditions degreening induction caused detached leaves to fully degreen within 48 hours (FIG. 5E, part b). However, darkness by itself failed to induce full degreening in detached leaves even after 72 hours (FIG. 5E, part c). We conclude that the degreening circuit is inducing a synthetic pathway that is distinct from chlorophyll loss found in senescence.

Signal-induced chlorophyll loss provides an easily recognizable phenotype (white plants) that is distinct from stressed plants, and a reset capacity. The two remaining characteristics needed for a readout system in a plant sentinel are rapid response and remote imaging capacity.

Light energy absorbed by chlorophyll follows several competing paths: photosynthetic electron transport drive, heat dissipation through the xanthophyll cycle, re-emission as fluorescence, or formation of triplet chlorophyll (Maxwell and Johnson, 2000). Because the pathways are competing, and the sum of rate constants is unvarying, information about the plants physiological state can be inferred by remote analysis of chlorophyll fluorescence (West et al., 2003; Zarco-Tejada et al., 2002). In addition, because plants must quickly respond to changing light conditions, chlorophyll responses are rapid.

To determine if chlorophyll fluorescence measurements would provide rapid diagnostic and remote imaging capacities to the degreening circuit system, we used commercially available chlorophyll monitor and software (Fluorcam, Photon Systems Inc.) to measure how chlorophyll fluorescence behaved before and after induction of the degreening circuit.

Figure 5C:
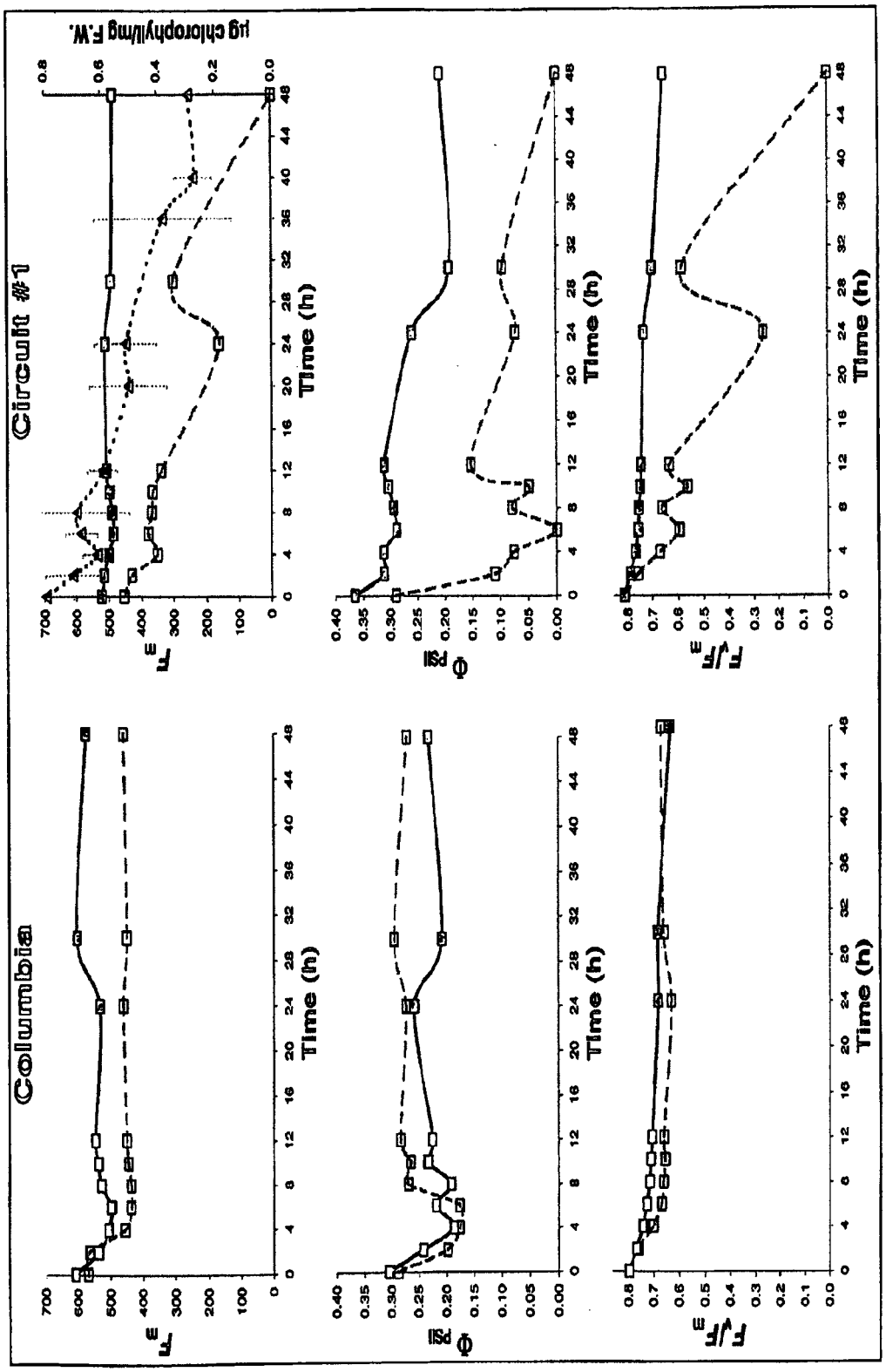
Figure 5D:
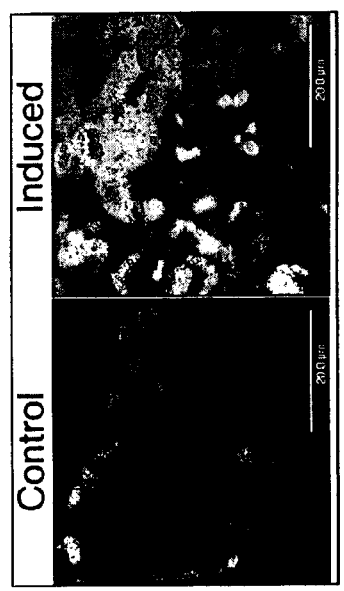
Figure 5E:
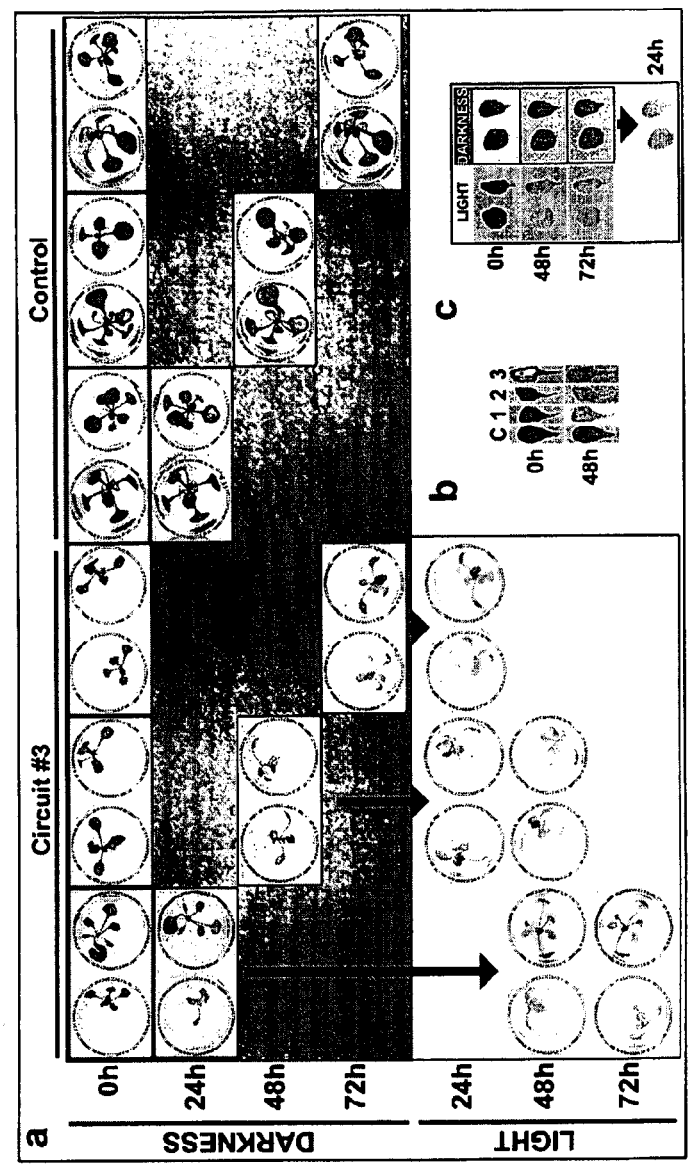

Control plants, both induced and uninduced, showed only slight changes in all parameters measured (FIG. 5C). $F_v/F_m$ measures the maximum quantum efficiency of PSII in dark-adapted plants and is often used as a measurement of plant stress (Maxwell and Johnson, 2000). Uninduced plants containing the degreening circuit had an initial $F_v/F_m$ value of 0.8 (FIG. 5C bottom). An $F_v/F_m$ value of 0.8 is close to the maximum possible PSII efficiency observed in normal, non-stressed plants (Adams et al., 1990). These results indicate that there are little physiological effects of the presence of the (silent) degreening circuit in uninduced plants. Upon induction of the degreening circuit, $F_v/F_m$ declines. Initial declines in $F_v/F_m$ were seen within 2 hours, and more substantial reductions observed at 6 hours.

$F_m$ is a measure of maximum chlorophyll fluorescence and an indirect measurement of total chlorophyll in dark-adapted plants. After degreening circuit induction, $F_m$ showed some initial variability, with stable reductions seen after 12 hours (FIG. 5C top). These initial variations in $F_m$ are similar to those found when total chlorophyll levels were measured spectrophotometrically (FIG. 5C top). Without wishing to be bound by any particular theory, this is believed to reflect plant mechanisms to attempt to compensate for enhanced chlorophyll degradation.

One of the most robust parameters derived from chlorophyll fluorescence measurements is $\phi_{PSII}$, representing the portion of light absorbed by chlorophyll in photosystem II (PSII) used in photochemistry. $\phi_{PSII}$ can also be measured in light grown plants under natural conditions (Maxwell and Johnson, 2000). FIG. 5C (middle) shows that plants induced to degreen had a large (nearly 60%) reduction in $\phi_{PSII}$ within 2 hours, the first time point measured. These results show the measurement of $\phi_{PSII}$ provides a straightforward means to rapidly and remotely detect induction of the degreening circuit reporting system.

Figure 5F:
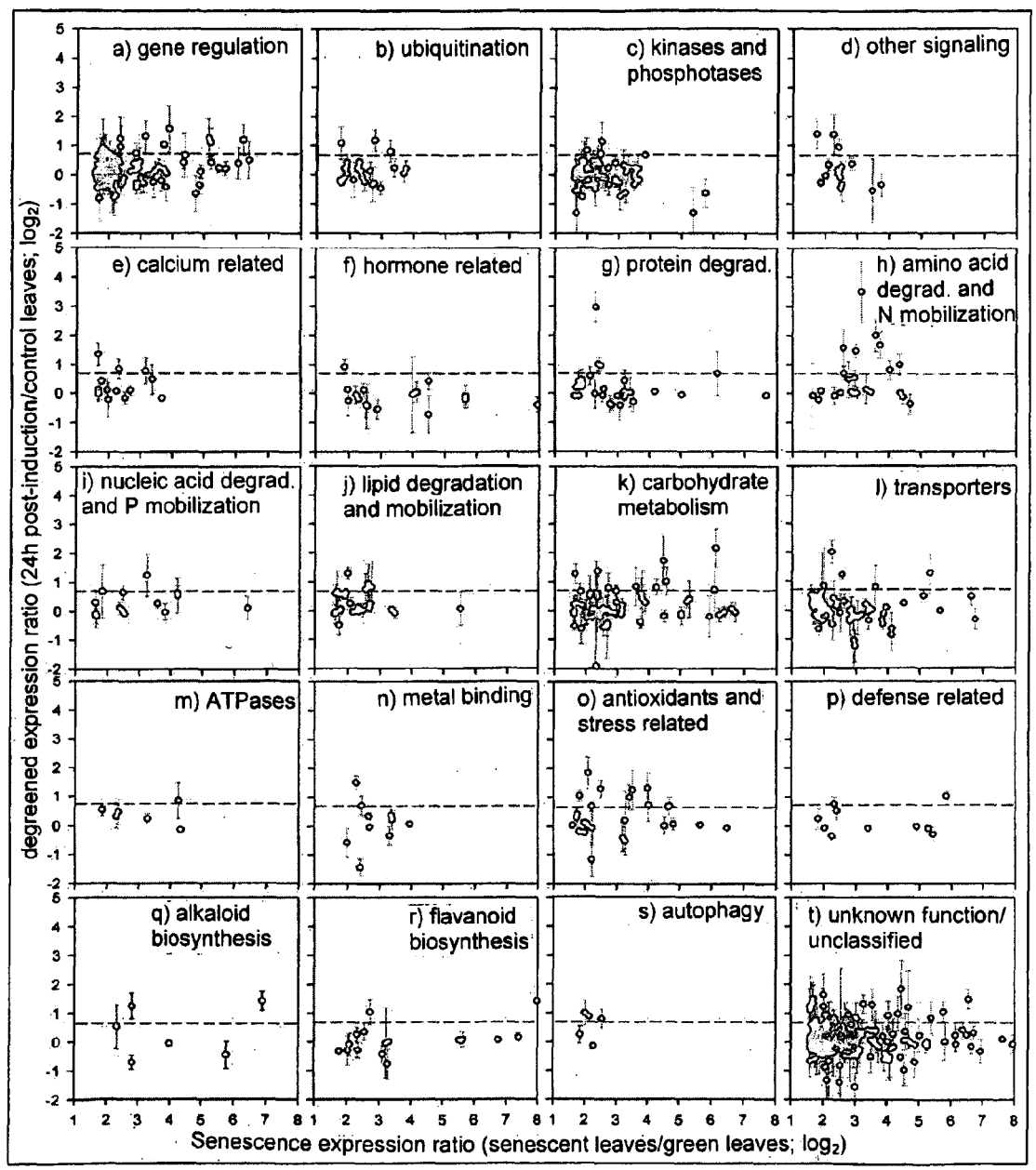

Global changes in gene expression during degreening are distinct from those of senescence. The degreening circuit causes chlorophyll loss relatively quickly, with response of leaves to dark treatment and ultrastructural aspects distinct from normal chlorophyll loss observed during senescence. To further test the idea that the degreening circuit initiates a synthetic process distinct from the chlorophyll loss in senescence, we employed microarray analysis. If the degreening circuit initiates a synthetic process, the genes involved in senescence should be relatively unaffected while genes encoding photosystem components might be affected. FIG. 5F shows plots comparing major classes of genes down-regulated by the degreening circuit to those down-regulated by senescence. As expected, the majority of annotated PSII- and PSI-related genes (e.g., light-harvesting chlorophyll a/b binding and oxygen-evolving complex proteins) are down-regulated within 24 hours of induction, the first time point measured. This includes PSII subunits (PSO1, PSO2, PSP1, PSP2, PSQ1, PSQ2) and PSI subunit precursors (Kieselbach and Schroder, 2003). Other notable down-regulated genes include DegP2, encoding a protease that is responsible for initial repair of damaged PSII proteins (Haussuhl et al., 2001), and FtsH6, a chloroplast LHCII protease (Zelisko et al., 2005). After 48 hours, these genes are also down-regulated. Also notable among the group down-regulated by the degreening circuit is PsbS (NPQ4), which allows excessive energy to be dissipated by photosynthetic antennas through the xanthophyll cycle (Holt et al., 2005; Li et al., 2004). While most photosystem genes are down-regulated, a few known photosystem genes were found to be up-regulated, including PsbP and genes encoding lumen proteins of unknown function (e.g., At1g03600, At3g09490).

In addition, microarray analysis shows that genes involved in ROS are up-regulated by the degreening circuit. Genes involved in anti-oxidative processes (Mittler et al., 2004), and genes involved in detoxifying products of lipid peroxidation (Loeffler et al., 2005) are induced by degreening (redox regulation and oxidative stress), including glutathione transferase, microsomal glutathione S-transferase, type 2 peroxiredoxin, NADP-dependent oxidoreductase, glutaredoxin, thioredoxin, peroxiredoxin, alternate oxidase, ferritin, blue copper protein, glutathione peroxidase, and several other peroxidases. The majority of genes known to be up-regulated during senescence were not induced by the degreening circuit (FIG. 5F). Genes that are strongly induced during senescence, but not during degreening, include enzymes for degradation of macromolecules (e.g. proteases, nucleases, lipases), transcription factors, kinases/phosphatases, defense related genes and flavonoid/anthocyanin biosynthetic genes (Buchanan-Wollaston et al., 2005). Within certain categories, small subsets of genes were commonly induced by both senescence and degreening, including chaperones, redox, autophagy, and alkaloid-like biosynthetic genes. Genes down-regulated in senescence were likewise largely not induced along with the degreening circuit. The prominent exception, where down-regulated senescence genes were down-regulated in degreened plants, is most of the nuclear encoded components of the photosynthetic machinery, including PSII, PSI, and Calvin Cycle genes.

Figure 6A:
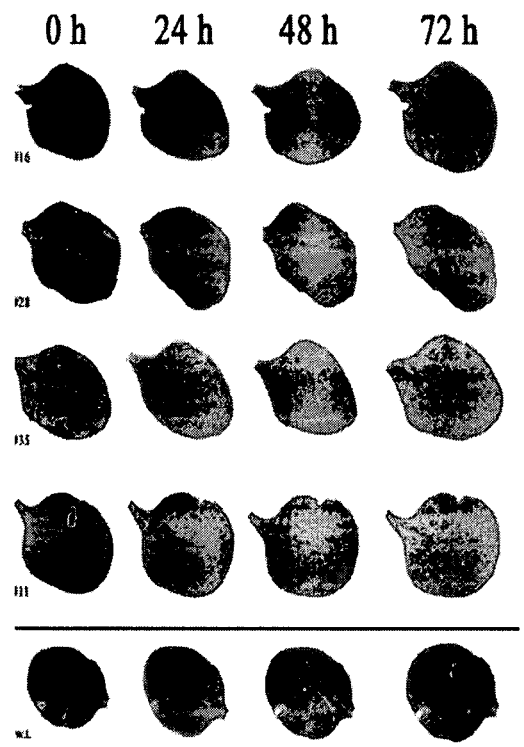
FIGS. 6A-6D show functional plant sentinel via linking input to degreening circuit. TNT induced Degreening: Transgenic *Arabidopsis* or Tobacco leaves containing ssTNT. FLS: Trg:PhoR, PhoB:VP64, and the PlantPho promoter controlling expression of the degreening genes, were excised and submerged in TNT. The progress of degreening was followed in one day increments.
Figure 6B:
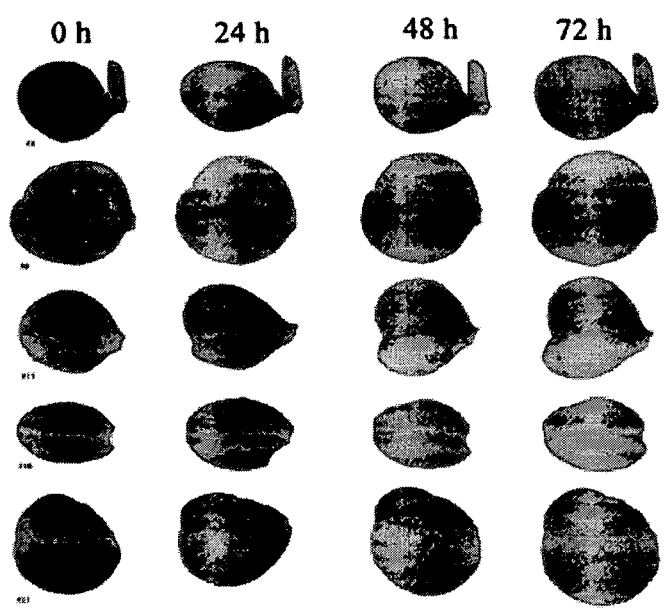
Figure 6C:
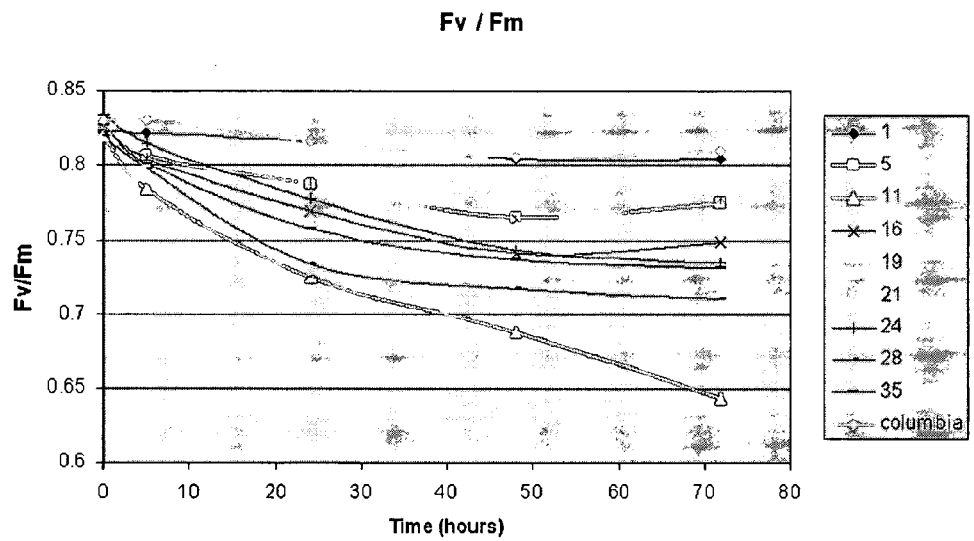
Figure 6D:
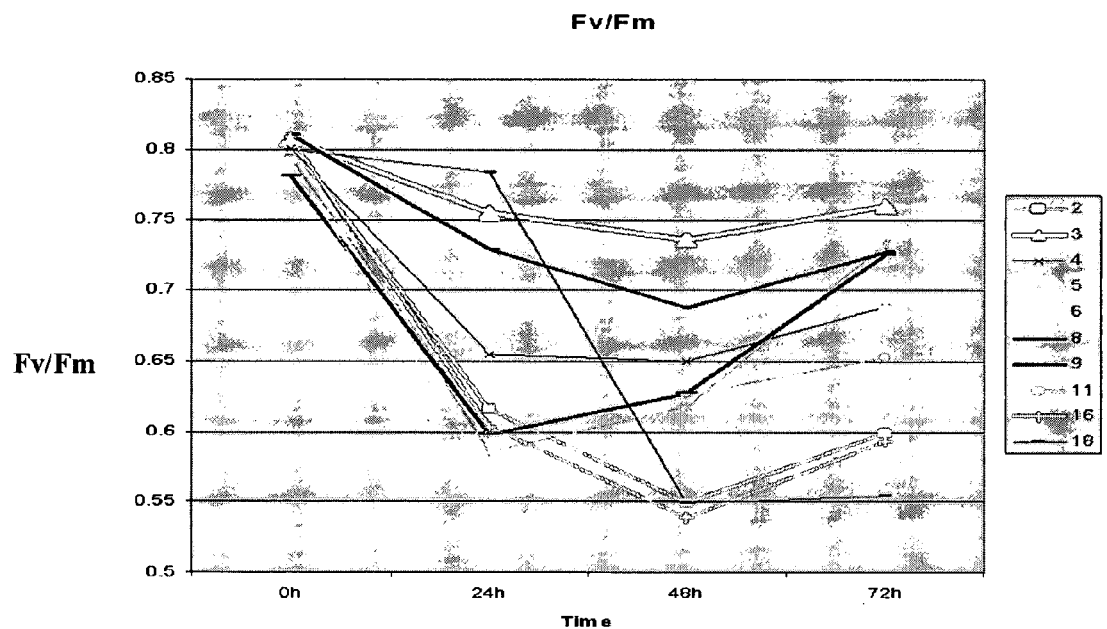

Computational Designed Receptors Used to Activate Degreening Circuit:

In order to demonstrate that the signal transduction pathway activated via computational designed receptors can activate the degreening circuit the 10XN1P promoters from the model degreening circuit were replaced with PlantPho promoters. *Arabidopsis* and tobacco plants were then co-transformed with the PlantPho promoter-degreening circuit and the SS-TNT, FLS:TRG:PhoR, PhoB:VP64 construct. FIG. 6 shows that both *Arabidopsis* and tobacco leaves incubated in the presence of TNT showed a degreening phenotype. FIG. 6A shows that the degreening circuit is induced with 100 pM (23 parts per trillion) of TNT in transgenic *Arabidopsis* plants resulting in white leaves. FIG. 6C shows this induction could be detected within 5 hours using remote techniques. FIGS. 6A and 6C show that a functional plant sentinel can be built. FIGS. 6B and 6D show that the technology also works in tobacco. FIG. 6B shows that notable degreening in these plants was induced with 10 μM TNT and the remote readout (chlorophyll fluorescence) was notably different at 24 hours.

Figure 7:
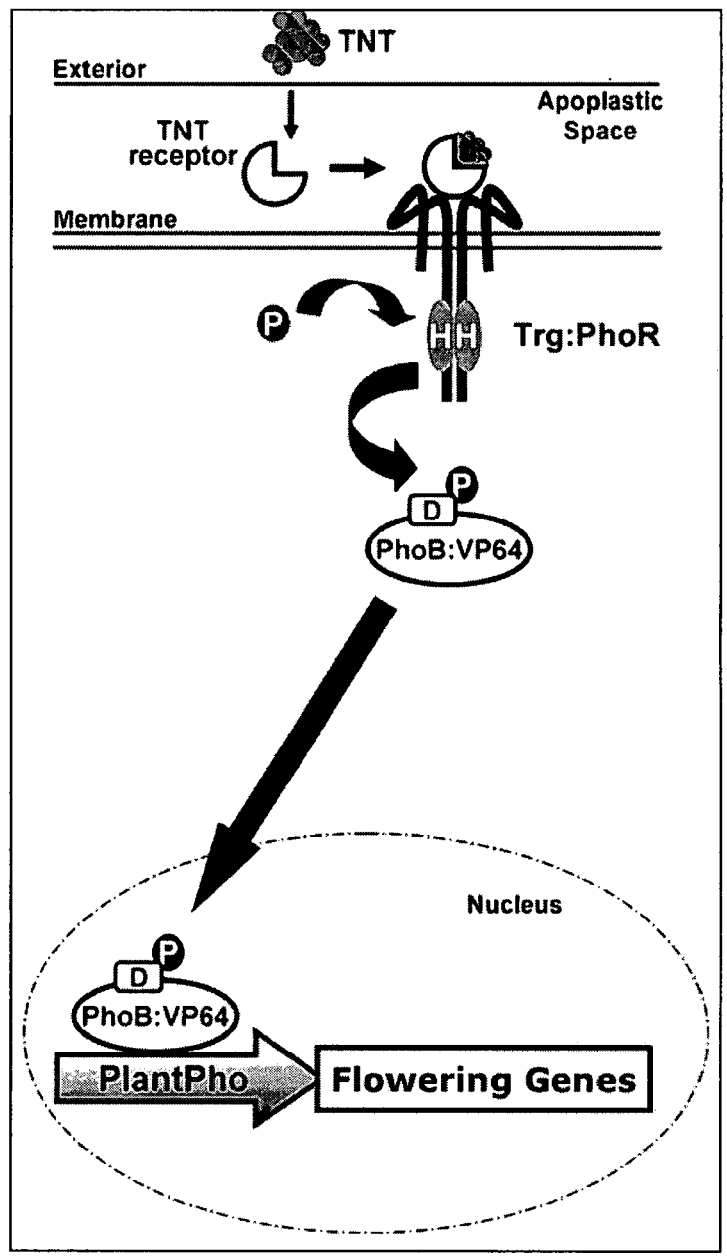
FIG. 7 shows a diagram of the function response circuit for flowering time in plants. This system could also be used to control processes other than degreening. As exemplified in the diagram, the detection and signaling systems could be linked to other outputs, for example, control of flowering time in plants. Control of flowering time in response to TNT is used here. Furthermore, the input could also be changed, simply by designing a new receptor (sensor protein), as detailed in the specification. Genes that control flowering time in plants, such as FT (Flowering Locus T), SOC1 (Suppressor of overexpression of CO 1), and others, could be placed under control of the PlantPho promoter. This would provide an input-sensitive system to control flowering time.

The above studies demonstrate that the degreening circuit of the invention can exhibit the degreening phenotype specifically and selectively in response to a signal. The loss of green color is quick, sensitive, and easy to detect directly or by remote sensing. Furthermore, the components of the degreening circuit are modular in that each component can be replaced with a specific component (e.g. binding protein/receptor or promoter) to provide a specific and selective response for a given input signal (target substance). FIG. 7 shows an example where the input (using for example TNT) activates transcription of a specific gene such as the FT (Flowering Locus T) gene critical for the conversion to flowering. Because of the modularity in the system, the input control could readily be changed so that, for example, the FT gene is induced by glyphosate, ribose or any of the computationally designed receptors.

Figure 8:
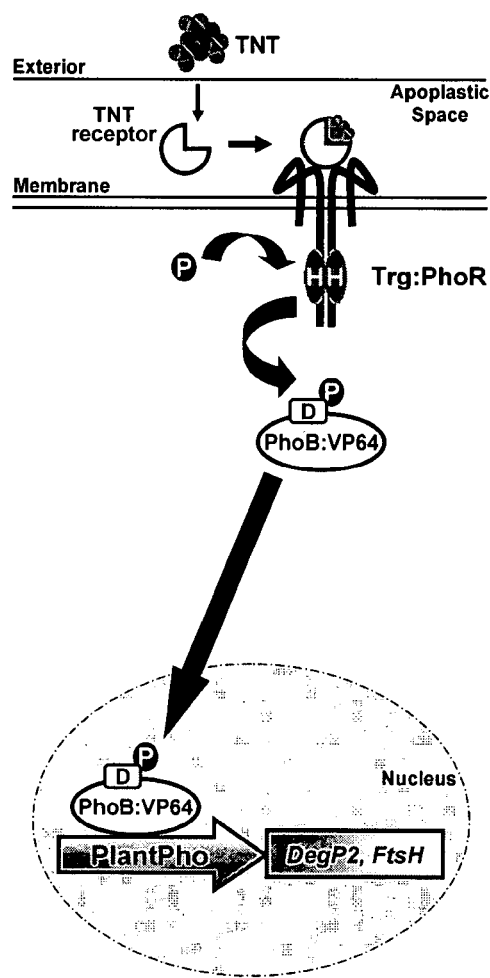
FIG. 8 shows TNT induction of the degreening circuit independent of light exposure. TNT-induced degreening of plants independent of light can be obtained by using the PlantPho promoter to direct expression of one or more genes encoding chloroplast-localized proteases that are involved in turnover of the D1 reaction center protein. Examples of proteases that could be used include, but are not limited to, DegP2, FtsH.

FIG. 8 shows enhancements to the degreening circuit that were evident from the microarray analysis. Both the DegP2 and FtsH gene encodes proteases involved in photosystem repair. Both genes have altered expression during the degreening process. By directing their expression with the PlantPho promoter the degreening readout system is faster and more independent of light.

Figure 9A:
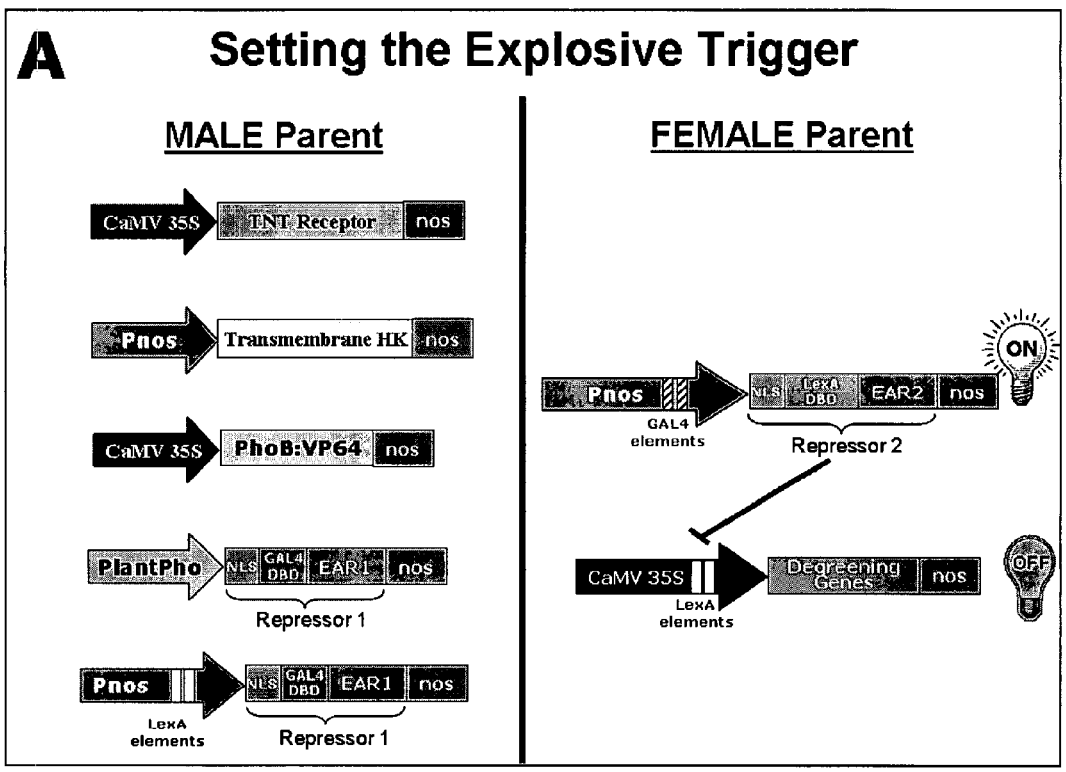
FIGS. 9A-9C show diagrams of the "trigger circuitry" for rapid induction of the degreening circuit in response to a single exposure to an input (TNT exemplified).
Figure 9B:
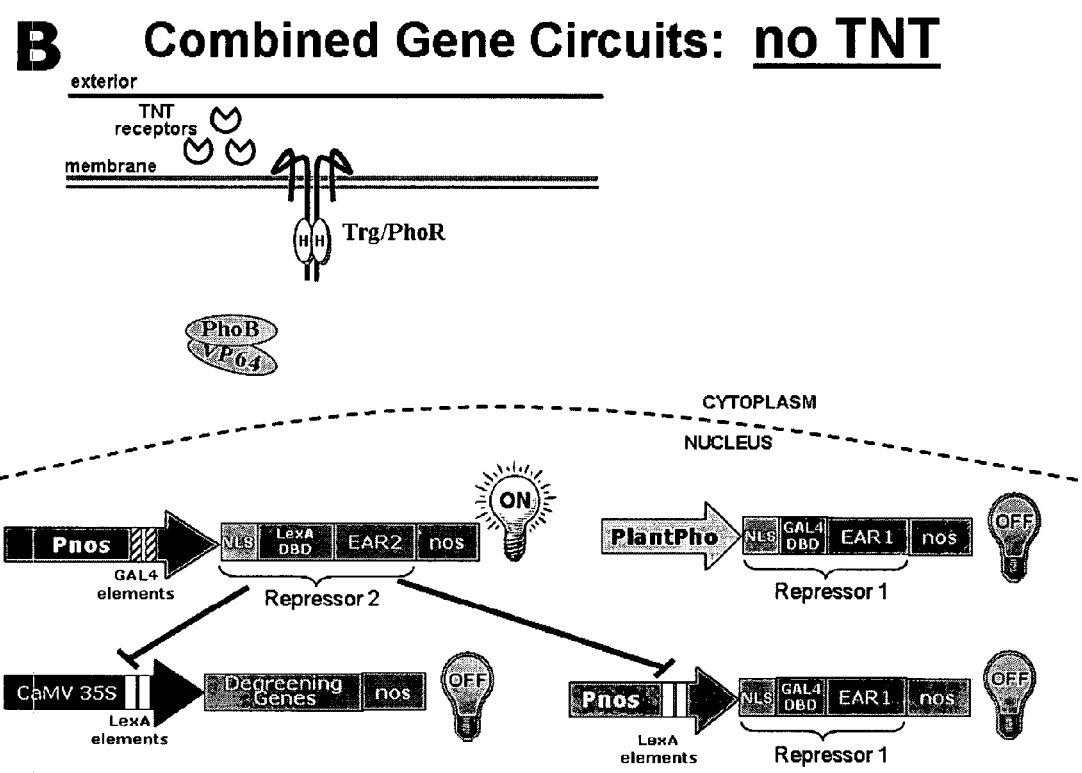
Figure 9C:
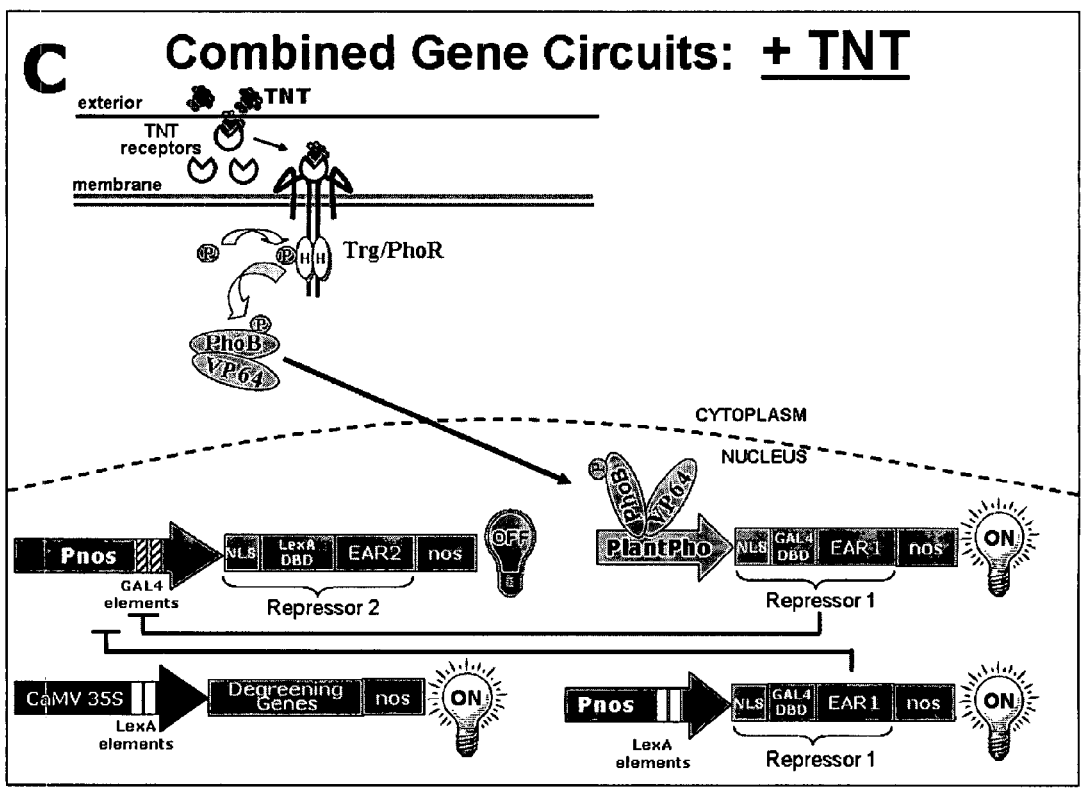

FIG. 9 shows details for making a "trigger" circuit that will allow response to a single exposure to a specific ligand. The features describe a series of feedback genes (repressors) that are tuned with synthetic biology for proper function. Critical to the setting process is using the fact that genes are not transcribed in the male pollen whereas they are transcribed in the female egg sac.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Experimental Details

Plant materials, growth conditions and transgenic plant production. *Arabidopsis thaliana*, ecotype Columbia (Col-0) plants were used for analysis and transgenic plant production. Standard growing conditions were 25° C., approximately 100 $\mu E\ m^{-2} \cdot s^{-1}$ light in either a Percival AR75L growth chamber (250±1° C.) or light shelf (250±2° C.), with a day/night cycle (16 h light, 8 hour dark), in Metro Mix 200 growth media (Scotts, Marysville, Ohio), supplemented with MIRACLE-GRO fertilizer. Transgenic plants were produced using the floral dip method (Clough and Bent, 1998). Plasmids were assembled as described below, transferred into *Agrobacterium tumefaciens* strain GV3101 by electroporation, and the selected *Agrobacterium* used for *Arabidopsis* transformation. Transgenic lines were selected on Murashige and Skoog (MS) media (Murashige and Skoog, 1962) containing 50 mg/L kanamycin or 5 mg/L glufosinate (Crescent Chemical Co., Islandia, N.Y.), depending on the vector, and 100 mg/L cefotaxime. $T_0$ lines were selected and allowed to self-pollinate, and only lines segregating for one T-DNA insert (3:1) and not showing any obvious phenotypic lesion were analyzed further. When possible, homozygous transgenic lines were obtained and used for analysis (degreening circuits #1, #2, and #3). With two degreening circuits (#4 and #5), homozygous lines could not be obtained or the homozygous lines set seed too poorly for detailed analysis. For plants containing these circuits, heterozygous lines were used.

Chemicals and Enzymes. MS salts, vitamins, and 4-hydroxytamoxifen (4-OHT) were all purchased from Sigma-Aldrich (St. Louis, Mo.). 5 mM 4-OHT stock solutions were prepared in ethanol and stored at −20° C. Enzymes used for cloning and DNA amplification were obtained from commercial suppliers and used according to the manufacturer's instructions.

Plasmid Construction. To test and develop the model degreening gene circuits, a chemically inducible transcription system was assembled for plants using the synthetic zinc finger proteins and DNA binding elements as described by Barbas and colleagues (Beerli et al., 2000; Segal et al., 2003). This steroid-regulated transcription system in plants is very similar to estrogen inducible systems previously described (Zuo et al., 2000), and use of these components in plants has been previously described (Stege et al., 2002).

The regulatory elements for the inducible system were first assembled. A steroid binding chimeric transcription factor (NEV) was placed under control of a strong constitutive promoter (FMV, figwort mosaic virus) (Bhattacharyya et al., 2002; Sanger et al., 1990), translation enhanced with the omega enhancer at the 5' end (Gallie et al., 1987), and expression terminated with the 3' end of the Nos (nopaline synthase) gene. NEV is a fusion protein, containing the synthetic N1 zinc finger DNA-binding domain (N), an estrogen receptor domain (E), and four copies of the herpes simplex virus (VP16) transcriptional activation domain (V) (Beerli et al., 2000). In animal cells, the NEV protein translocates to the nucleus and binds the synthetic N1 DNA element in the presence of the inducer. To make this system functional in plant cells, we synthesized the 10 copies of the N1 DNA element upstream of the minimal −46 CaMV35S promoter (Odell et al., 1985) (Egea Biosciences, Inc., San Diego, Calif.), creating a 223 bp promoter fragment referred to as 100XN1P. Both the chimeric transcription factor (FMV::Ω-NEV-Nos) and the synthetic N1 promoter 10XN1P were cloned into the plant transformation vectors pCAMBIA2300 or pMLBART.

To produce a synthetic degreening circuit, genes regulating chlorophyll biosynthesis and breakdown were placed under control of the inducible 10XN1P promoter and introduced into plant transformation vectors. Because multiple genes (up to 4) were introduced, a transcription block was placed between each gene or the genes were placed in a manner so as to prevent interference with expression of those genes (Padidam and Cao, 2001). The complete degreening circuit combines two types of genetic circuits: a gene circuit to inhibit biosynthesis of new chlorophyll biosynthetic enzymes, and thus chlorophyll synthesis, and a gene circuit to stimulate chlorophyll breakdown. All chlorophyll regulatory genes in the different constructs were placed under control of the 100XN1P promoter, allowing a coordinated expression upon addition of the 4-OHT inducer.

To inhibit biosynthesis of chlorophyll, diRNA constructs were assembled specific to the GUN4 gene (Larkin et al., 2003) or a conserved region found in the POR genes (Masuda et al., 2003; Oosawa et al., 2000). To generate the diRNA constructs, POR sense-intron-POR antisense, or GUN4 sense-intron-GUN4 antisense were cloned into pBluescript KS(+), including approximately 500 bp GFP coding sequence used as intron sequences at NotI/EcoRV. POR sense/GUN4 sense was cloned in via SacI/NotI and POR antisense/GUN4 antisense cloned in via EcoRV/XhoI (XmaI/XhoI for the GUN4 diRNA construct), then subcloned downstream of 10XN1P in p2300-FMV::Ω-NEV-nos-10XN1P at the AvrII/MluI sites. An octopine synthase (ocs) terminator was added at the MluI site, resulting in p2300-FMV::Ω-NEV-nos-10XN1P::POR diRNA-ocs, or p2300-FMV::Ω-NEV-Nos-10XN1P::GUN4 diRNA-ocs.

The gene circuit to initiate the breakdown of chlorophyll contains the Chlorophyllase1 (CHLASE) (Tsuchiya et al., 1999) gene to remove chlorophyll's hydrophobic tail, and a gene or gene(s) to open the porphyrin ring, Red Chlorophyll Catabolite Reductase (RCCR) (Wuthrich et al., 2000) and/or Pheophorbide a Oxygenase (PAO) (Pruzinska et al., 2003). Chlorophyll degradation genes were added as a combination of either CHLASE and RCCR, or CHLASE and PAO; or, in its final form as CHLASE, PAO and RCCR. These gene combinations, all under control of the 10XN1P promoter, were first assembled in pBluescript KS(+). CHLASE was placed downstream of 10XN1P via BstXI/NotI, and the Nos terminator was added at the SpeI/SmaI sites; RCCR was fused with 10XN1P via PstI/EcoRI, and the Nos terminator (EcoRI/ApaI). Transcription blocks (TB) were included between the Nos terminator and 10XN1P via SmaI/PstI. The RCCR gene was replaced with PAO using the same restriction sites described above, to generate the CHLASE-PAO combination. Assembled 10XN1P::CHLASE-Nos-TB-10XN1P::RCCR-Nos or 100XN1P::CHLASE-Nos-TB-10XN1P::PAO-Nos was added to the 3' end of either POR or GUN4 diRNA in p2300-FMV::Ω-NEV-Nos-10XN1P::POR diRNA-ocs (or p2300-FMV::Ω-NEV-Nos-10XN1P::GUN4 diRNA-ocs), as an ApaI fragment, to complete degreening circuits. The "initiate breakdown" constructs (CHLASE+RCCR, and CHLASE+PAO) were assembled by first PCR-amplifying FMV::Ω-NEV-Nos-TB from p2300-FMV::Ω-NEV-Nos-TB using primers FMVFwd, 5'-ATTTAGCAGCATTCCAGATTGGGTTC-3' (SEQ ID NO:15), and TBRev, 5'-AGAGAAATGTTCTGGCACCTG-CACTTG-3' (SEQ ID NO:16). The PCR product was cloned as a blunt fragment into SpeI-digested and Klenow-treated pART27-based vector pMLBART (Gleave, 1992), resulting in pMLBART-FMV::Ω-NEV-Nos-TB. The CHLASE and RCCR genes, as well as the CHLASE and PAO genes, all under control of the 10XN1P promoter were excised from vectors containing degreening circuits #1 and #3, respectively, as ApaI fragments. After flushing the ends, these fragments were ligated into NotI-digested, Klenow-treated pMLBART-FMV::Ω-NEV-Nos-TB. All gene fusions and all chlorophyll regulatory genes were verified by sequencing (Macrogen Inc., Seoul, Korea) before final assembly into pCAMBIA2300 and pMLBART vectors.

Generation of transgenic plants. ssTNT, FLS:Trz:AHK4 construct:A fusion between the Pex secretory sequence and the periplasmic ribose binding protein engineered to bind TNT (the procedure for this fusion will work on any engineered RBP) was formed using a variation of standard PCR techniques. Primers were designed that created a sequence overlap between the secretory sequence and RBP. Two initial PCR reactions were performed using standard PCR conditions in 50 μl reactions. One reaction on the Pex secretory sequence using primers 5'-CTTCGGATCCATGGAGAG-GCCCTTTG-3' (SEQ ID NO:17) and 5'-CGCGATGGT-GTCTTTGGCCACGACGGTATA-3' (SEQ ID NO:18). The second reaction on the engineered RBP gene used primers 5'-TATACCGTCGTGGCCAAAGACACCATCGCG-3' (SEQ ID NO:19) and 5'-AGGAGAGCTCTACTGCTTAA-CAACCAG-3' (SEQ ID NO:20) An MJ thermocycler and a high fidelity polymerase (expand high fidelity Taq polymerase, Roche) were used. The products from the initial PCR contain overlapping sequence homology at the junction point between the secretory sequence (SS) and the RBP sequence. The PCR products were diluted to about 10 ng/μl and placed in a standard PCR reaction mix which lacked any primers. The PCR reaction mix was subjected to a PCR cycle of 95° C. for 2 min, 52° C. for 1 min and 72° C. for 3 min overall for 3 cycles. This allowed the overlapping sequences between the Secretory Sequence (SS) and RBP to anneal together. The annealed ends of the PCR products can then act as primers to facilitate a reaction where the Taq polymerase replicates or "fills-in" the rest of the gene fusion creating a double stranded SS-RBP (or ssTNT) gene fusion. After 3 cycles the upper primer used on the Secretory sequence 5'-CTTCGGATC-CATGGAGAGGCCCTTTG-3' (SEQ ID NO:21) and the lower primer used on the RBP sequence 5'-AGGAGAGCTC-TACTGCTTAACAACCAG-3' (SEQ ID NO:22) were added to the PCR tubes. This allowed for amplification of the full length SSTNT product after 27 cycles using standard PCR conditions. Intermediate cloning of the PCR products was done using PCRTerminator end repair kit and CloneSmart kit vector pSMART from Lucigen and coding sequence integrity was confirmed by sequencing. The SS upper primer contains a BamH1 site and the lower RBP primer contains a SacI site allowing cloning of the ssTNT gene fusion into the BamH1 and SacI sites between the 35S promoter and Nopaline Synthetase Terminator of the plant transformation vector pCB302-3. A similar procedure was performed to form a fusion between the FLS2 signal sequence and the Trz:AHK4 gene using the same techniques describe above, and using primers 5'-GTTGCGGATCCATGAAGTTACTCTCAAAG-3' (SEQ ID NO:23) and 5'-GATACGGTTAAT-CATTTTCGCTAGTGCAAT-3' (SEQ ID NO:24) for the plasma membrane targeting sequence of FLS2 and primers 5'-ATTGCACTAGCGAAAATGATTAACCGTATC-3' (SEQ ID NO:25) and 5'-GCGATCGCTTACGACGAAGGT-GAGATAG-3' (SEQ ID NO:26) for Trz:AHK4. Fls:Trz: AHK4 was cloned into the BamHI and SgfI sites of a pBluecript plasmid which contained a Nopaline Synthetase Promoter (PNOS) and the Nopaline Synthetase Terminator (TNOS) fused to a transcription block(TB). A PCR segment containing the entire PNOS-Fls:Trz:AHK4-TNOS-TB sequence with HindIII sites at the 5' and 3' ends was generated using the primers 5'-CTTCAAGCTTGATTCCCCGGAT-CATGAG-3' (SEQ ID NO:27) and 5'-CTTCAAGCTTA-GAGAAATGTTCTGGCAC-3' (SEQ ID NO:28). The PNOS-Fls:Trz:AHK4-TNOS-TB was ligated into the HindIII site of the pCB302-3 vector containing ssTNT. The construct containing ssTNT-Fls:Trg:PhoR in pCB302-3 was created using primers and techniques essentially as above with the exception that a PhoR specific lower primer was used in making the Fls:Trg:PhoR fusion. The PhoR lower primer sequence used is 5'-GCAAGCGATCGCTTAATCGCT-GTTTTTGGCAA-3' (SEQ ID NO:29).

TNT Induction of *Arabidopsis* Plants. TNT (ChemService, West Chester, Pa.) stock solution was prepared by dissolving TNT powder in DMSO. Final solutions containing different concentrations of TNT were prepared in water. Plants were incubated in water (control) or water plus 10 uM TNT for 16 hours.

GUS fluorometric assays. After incubation of plants with inducer of the gene circuit (CK, TNT, etc.), plants/leaves were ground in extraction buffer (50 mM NaHPO$_4$, pH 7.0, 10 uM β-mercaptoethanol, 10 mM Na$_2$EDTA, pH 8.0, 0.1% Sarcosyl, 0.1% Triton X-100). GUS Reaction: Protein extract combined with extraction buffer was incubated and then stopped with reaction stop buffer (0.2 M Na$_2$ CO$_3$) and 4-MU fluorescence read on a DyNA Quant 200 Fluorometer (Hoefer, Inc., San Francisco, Calif.) (Gallagher, S. R., 1992).

Plant material, transgenic plant production and growth conditions. Wild type *Arabidopsis thaliana* (ecotype Columbia) were used for analysis and transgenic plant production. Plasmids were assembled as described above and transferred into *Agrobacterium tumefaciens* strain GV3101 by electroporation. *Arabidopsis* plants were transformed with this *Agrobacterium* strain containing the assembled plasmids by floral dip method (Clough and Bent, 1998). Transgenic T$_0$ plants were selected on standard germination medium (GM) containing full strength Murashige and Skoog Salts (Murashige and Skoog, 1062). Leaves from wild-type tobacco plants (cultivar SR1) were transformed using *Agrobacterium tumefaciens* strain GV3101 by electroporation (same as the *Arabidopsis* plants). Leaves were co-cultivated with the *Agrobacterium* for 2-3 days. Transgenic tobacco plants were regenerated on standard MS selection media supplemented with 50 mg/l Kanamycin (sigma) and 5 mg/l glufosinate (Crescent Chemical Co). Once shoots formed plants were transferred to MS media for rooting. Media is as above except that it lacked BAP and NAA (Dandekar et. al., 2005).

Induction of plant degreening and regreening. For the induction of degreening, 14-day old transgenic plants containing a single copy of the specific gene circuit were grown aseptically on MS medium with 50 mg/L kanamycin but without sucrose. Individual plants were incubated in 24-well Cellstar culture plates (Greiner Bio-one, Longwood, Fla.), each well containing 2 mL of liquid MS media without sucrose, supplemented (induced) or not (control) with the inducer, 10 μM 4-OHT. Induction of the degreening circuit typically started 1 hour into the 16 hour light period, but results were the same regardless of when the induction started. Plants were returned to the growth conditions described above and incubation continued for the different time periods or conditions described in the text. After degreening, plants were induced to regreen by incubation in 1 μM t-zeatin for 6 hours, then transferred to plates containing MS media, and allowed to regreen for up to 7 days. Plants regreened without use of the cytokinin, however, cytokinin treatment enhanced the process.

Semi-quantitative RT-PCR analysis. Total RNA was isolated from whole plants using the AURUM Total RNA Mini kit (Bio-Rad Laboratories, Hercules, Calif.), according to the instructions from the manufacturer. cDNA synthesis and PCR amplification were performed with 200 ng total RNA, using the ACCESSQUICK RT-PCR System (Promega, Madison, Wis.) and gene-specific primers. Even though the RT-PCR system uses a DNase step, primers were designed to span an intron-exon junction except for GUN4, which lacks introns. The following primers were used: Cyclophilins, 5'-GCGT-TCCCTAAGGTATACTTCGAC-3' (SEQ ID NO:30) and 5'-CCCATGAGAACACACCAAAC-3' (SEQ ID NO:31); GUN4,5'-ACGCAAAATCTGGTTAAAAGT-GAA-3' (SEQ ID NO:32) and 5'-TTGTGAGCGGTAAGT-GTCCTAAAG-3' (SEQ ID NO:33); POR, 5'-TTGACCAT-CAAGGAACAGAGAA-3' (SEQ ID NO:34) and 5'-TATTTGTGTTTCCTGTTATAGA-3' (SEQ ID NO:35); CHLASE, 5'-TAGCCCCACAGTTGTGCAAATT-3' (SEQ ID NO:36) and 5'-AAGTCCGTTGGTGCGCATGGTG-3' (SEQ ID NO:37); RCCR, 5'-AATCTTCTCCGAT-TGATTTTGT-3' (SEQ ID NO:38) and 5'-CTAGAGAACAC-CGAAAGCTTCT-3' (SEQ ID NO:39); PAO, 5'-TCTAT-GAACAAAATTGAGTTAG-3' (SEQ ID NO:40) and 5'-CTACTCGATTTCAGAATGTACA-3' (SEQ ID NO:41). PCR amplification consisted of 1 cycle at 95° C. for 2 min, followed by 25 cycles each of 95° C. for 40 sec, 52° C. for 30 sec, 72° C. for 1 min, and a final extension step at 72° C. for 5 min. Amplification products were separated on 2% agarose gels, and photographed under UV light using a Scion Image Capture System.

Total chlorophyll and protein measurements. Chlorophyll was extracted in 2.5 mM sodium phosphate buffered (pH 7.8) 80% acetone. Absorbance of the resulting solution was measured at 646.6 and 663.6 nm on a Shimadzu UV-1201 spectrophotometer, and total chlorophyll content (μg/mL) was calculated using the formula: $17.76 A_{646.6}+7.34 A_{663.6}$ (Porra et al., 1989). Total proteins were estimated using the Bradford reagent (Bio-Rad, Hercules, Calif.) using BSA as a standard (Bradford, 1976).

Western blot analysis. Plants (3-5 per time point) were ground in liquid nitrogen and resuspended in 250 μL 12.5 mM sodium phosphate buffer (pH 7.8). Protein concentration was determined using the Bradford reagent (Bradford, 1976). Protein samples were loaded based on equal fresh weight on 12% SDS-PAGE gels, electrophoresed for 40 minutes at 200 V, and transferred to Hybond-P (Amersham Biosciences) membranes. Western hybridizations were performed with the ECL plus western blotting detection system (Amersham Biosciences). The GUN4 antibody was provided by Dr. R. M. Larkin (Michigan State University, East Lansing, Mich.) and used as recommended. Briefly, this consisted of blocking with 5% Blotting Grade Blocker non-fat dry milk (Bio-Rad) in PBS (pH 7.5), followed by incubation with the GUN4 antibody at a 1:1600 dilution and the secondary antibody (HRP-conjugated anti-rabbit IgG, Pierce Biotechnology, Rockford, Ill.) at a 1:20,000 dilution. The POR antibody was provided by Dr. G. A. Armstrong (Ohio State University, Columbus, Ohio). Blocking conditions were similar to those described for GUN4, followed by incubation with POR antibody at 1:500 dilution and secondary antibody at 1:10,000 dilution. Western blots were scanned and quantified using a Molecular Dynamics Storm 840 system.

Microarray. 14 day-old transgenic plants bearing degreening circuit #3 were harvested before induction, 24 h and 48 h post-induction with 10 μM 4-OHT, and also after being allowed to regreen for 3 days. Treatments were replicated in two biologically independent experiments. Total RNA was isolated from each sample (8 plants/treatment) using Aurum™ Total RNA Mini kit (Bio-Rad Laboratories, Hercules, Calif.). Paired 2.5 μg aliquots from each treated and control RNA sample were reciprocally labeled with either Cy3 or Cy5 dendrimers using the Array 900™ system (Genisphere, Hatfield, Pa.), such that RNA from each treatment was labeled and hybridized (in parallel with a contrastingly labeled control sample) four separate times, for a total of twelve microarrays balanced with respect to treatment, dye, and biological replication. Microarrays were spotted at high-density on SUPERAMINE slides (Telechem, Sunnyvale, Calif.) using amine-modified 70-mer oligonucleotide probes (ATH1 version 1, Operon, Huntsville, Ala.) representing essentially every predicted gene in the Arabidopsis genome. Microarray signal intensities were quantified and analyzed using the TM4 software suite (Saeed et al., 2003). Raw signal intensities were normalized within array blocks using the Lowess function, and normalized, $log_2$ transformed signal intensities of >10 units (on a scale of 0-26) were subjected to statistical tests (t-test, one way ANOVA) to identify expression ratios that differed significantly from the mean.

Chlorophyll fluorescence imaging. To visualize early changes in photosynthetic efficiency due to the degreening process, images of chlorophyll fluorescence were obtained using the Fluor Cam (Photon Systems Instruments, Brno, Czech Republic). Plants were induced to degreen as described above, and were compared to non-induced, as well as wild-type Columbia plants as a control. Plants were dark-adapted for minutes prior to fluorescence measurements. Data were obtained using the default fluorescence Quenching Analysis protocol, with the following modifications: a 30 sec dark pause after the $F_m$ measurement was used; pulse fluorescences were subtracted for $F_m$ measurement of the "dark" level and for $F_m$ measurements during Kautsky induction. Data analysis was performed using the manufacturer's software (Fluorcam v. 5.0). Time course plots of the relevant parameters were generated using Microsoft Excel.

Reactive oxygen species (ROS) detection. To investigate the production of ROS during the degreening process, the probe CM-$H_2$DCFDA (Molecular Probes, Eugene, Oreg.) was used. DCFDA is a cell-permeant indicator which is non-fluorescent until the acetate groups are removed by intracellular esterases and oxidation occurs within the cell. ROS production was visualized under an Olympus FVX-IHRT Fluoview confocal laser scanning microscope using an Argon (488 nm) laser. Chlorophyll auto-fluorescence was visualized following excitation with a HeNe (543 nm) laser.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

References

Adams, W. W., 3rd, Demmig-Adams, B., Winter, K. and Schreiber, U. (1990) The ratio of variable to maximum Chi fluorescence from Photosystem II, measured in leaves at ambient temperature and at 77K, as an indicator of the photon yield of photosynthesis. Planta 180: 166-174.

Allert, M., Rizk, S. S., Looger, L. L. and Helling a, H. W. (2004) Computational design of receptors for an organophosphate surrogate of the nerve agent soman. Proc Natl Acad Sci USA 101: 7907-7912.

Antunes, M. S., Ha, S. B., Tewari-Singh, N., Morey, K. J., Trofka, A. M., Kugrens, P., Deyholos, M., Medford, J. I. (2006) A synthetic de-greening gene circuit provides a reporting system that is remotely detectable and has a re-set capacity. Plant Biotechnol. J. 4:605-622.

Amon D (1949) Copper enzymes in isolated chloroplasts: polyphenoloxidase in Beta vulgaris. Plant Physiol 84: 1901-1905.

Baluska, F., Samaj, J., Wojtaszek, P., Volkmann, D. and Menzel, D. (2003) Cytoskeleton-plasma membrane-cell wall continuum in plants. Emerging links revisted. Plant Physiol. 133:482-491.

Baumberger, N., Doesseger, B., Guyot, R., Diet, A., Parsons, R. L., Clark, M. A., Simmons, M. P., Bedinger, P., Goff, S. A., Ringli, C. and Keller, B. (2003). Whole-genome comparison of leucine-rich repeat extensins in Arabidopsis and rice. A conserved family of cell wall proteins form a vegetative and a reproductive clade. Plant Physiol. 131:1313-1326.

Baumgartner, J. W., Kim, C., Brissette, R. E., Inouye, M., Park, C. and Hazelbauer, G. L. (1994) Transmembrane signalling by a hybrid protein: communication from the domain of chemoreceptor Trg that recognizes sugar-binding proteins to the kinase/phosphatase domain of osmosensor EnvZ. J. Bacteriol. 176:1157-1163.

Bechtold N, Ellis J, Pelletier G (1993) In planta Agrobacterium mediated gene transfer by infiltration of adult Arabidopsis thaliana plants. C. R. Acad. Sci. Paris, Sciences de la vie 316: 1194-1199

Beerli R R, Barbas C F, 3rd (2002) Engineering polydactyl zinc-finger transcription factors. Nat Biotechnol 20: 135-141.

Beerli R R, Dreier B, Barbas C F, 3rd (2000) Positive and negative regulation of endogenous genes by designed transcription factors. Proc Natl Acad Sci USA 97: 1495-1500.

Beerli R R, Schopfer U, Dreier B, Barbas C F, 3rd (2000) Chemically regulated zinc finger transcription factors. J Biol Chem 275: 32617-32627.

Benedetti C E, Arruda P (2002) Altering expression of the chlorophyllase gene ATHCOR1 in transgenic Arabidopsis caused changes in the chlorophyll-to-chlorophyllide ration. Plant Physiology 128: 1255-1263

Benedetti C E, Arruda P (2002) Altering the expression of the chlorophyllase gene ATHCOR1 in transgenic Arabidopsis caused changes in the chlorophyll-to-chlorophyllide ratio. Plant Physiol 128: 1255-1263

Bhattacharyya, S., Dey, N. and Maiti, I. B. (2002) Analysis of cis-sequence of subgenomic transcript promoter from the Figwort mosaic virus and comparison of promoter activity with the cauliflower mosaic virus promoters in monocot and dicot cells. Virus Res: 90, 47-62.

Biswal, U. C., Biswal, B. and Raval, M. K. (2003) Chloroplast biogenesis: from proplastid to gerontoplast. Dordrecht; Boston; Kluwer Academic Publishers.

Blanco, A. G., Sola, M., Gomis-Ruth, F. X. and Coill, M. (2002) Tandem DNA recognition by PhoB, a two-component signal transduction transcriptional activator. Structure (Camb). 10:701-713.

Bowser J, Reddy A S (1997) Localization of a kinesin-like calmodulin-binding protein in dividing cells of *Arabidopsis* and tobacco. Plant J 12: 1429-1437

Bradford, M. M. (1976) A rapid and sensitive method for the quantitation of microgram quantities of protein utilizing the principle of protein-dye binding. Anal Biochem 72: 248-254.

Buchanan-Wollaston, V., Page, T., Harrison, E., Breeze, E., Lim, P. O., Nam, H. G., Lin, J. F., Wu, S. H., Swidzinski, J., Ishizaki, K. and Leaver, C. J. (2005) Comparative transcriptome analysis reveals significant differences in gene expression and signalling pathways between developmental and dark/starvation-induced senescence in *Arabidopsis*. Plant J 42: 567-585.

Clough, S. J. and Bent, A. F. (1998) Floral dip: a simplified method for *Agrobacterium*-mediated transformation of *Arabidopsis thaliana*. Plant J, 16, 735-743.

Carter, G. A. and Knapp, A. K. (2001) Leaf optical properties in higher plants: linking spectral characteristics to stress and chlorophyll concentration. Am J Bot 88: 677-684.

Chuang C F, Meyerowitz E M (2000) Specific and heritable genetic interference by double-stranded RNA in *Arabidopsis thaliana*. Proc Natl Acad Sci USA 97: 4985-4990

Chung M H, Chen M K, Pan S M (2000) Floral spray transformation can efficiently generate *Arabidopsis* transgenic plants. Transgenic Res 9: 471-476

Clark S E, Williams R W, Meyerowitz E M (1997) The CLAVATA1 gene encodes a putative receptor kinase that controls shoot and floral meristem size in *Arabidopsis*. Cell 89: 575-585

Clough S J, Bent A F (1998) Floral dip: a simplified method for *Agrobacterium*-mediated transformation of *Arabidopsis thaliana*. Plant J 16: 735-743

Dangl J L, Dietich R A, Thomas H (2000) Senescence and programmed cell death. In BB Buchanan, W Gruissem, R L Jones, eds, Biochemistry & Molecular Biology of Plants. American Society of Plant Physiologists, Rockville, Md., pp 1044-1100

Dangl J L, Jones J D (2001) Plant pathogens and integrated defence responses to infection. Nature 411: 826-833

Dandekar A M, Fisk H J (2005) Plant Transformation in Methods in Molecular Biology vol 286: Transgenic Plants: Methods and Protocols Edited by L. Pena, Humana Press Inc., Totowa N.J.

Desfeux C, Clough S J, Bent A F (2000) Female reproductive tissues are the primary target of *Agrobacterium*-mediated transformation by the *Arabidopsis* floral-dip method. Plant Physiol 123: 895-904

Dreier B, Beerli R R, Segal D J, Flippin J D, Barbas 1 (2001) Development of zinc finger domains for recognition of the 5'-ANN-3' family of DNA sequences and their use in the construction of artificial transcription factors. J Biol Chem 4: 4

Dwyer, M A, Looger, L L, Helling a, H W (2003) Computational design of a $Zn^{2+}$ receptor that controls bacterial gene expression. Proc Natl Acad Sci USA 100:11255-11260.

Dwyer, M A and Helling a H. W. (2004). Periplasmic binding proteins: a versatile superfamily for protein engineering. Curr. Opin. Struct. Biol. 14:495-504.

Eckhardt, U., Grimm, B. and Hortensteiner, S. (2004) Recent advances in chlorophyll biosynthesis and breakdown in higher plants. Plant Mol Biol, 56, 1-14.

Fletcher J C, Simon R, Running M P, Meyerowitz E M (1998) The CLAVATA3 gene encodes a small protein specifically associated with meristem activity in *Arabidopsis*. *Arabidopsis* Research Conference Abstracts 9: 452

Fraley R T, Rogers S G, Horsch R B, Eichholtz D A, Flick J S, Hoffmann N L, Sanders P R (1985) The SEV system: A new disarmed Ti plasmid vector system for plant transformation. Bio/technology 3: 629-635

Frick, G., Su, Q., Apel, K. and Armstrong, G. A. (2003) An *Arabidopsis* porB por C double mutant lacking light-dependent NADPH:protochlorophyllide oxidoreductases B and C is highly chlorophyll-deficient and developmentally arrested. Plant J 35: 141-153.

Friml J, Benkova E, Blilou I, Wisniewska J, Hamann T, Ljung K, Woody S, Sandberg G, Scheres B, Jurgens G, Palme K (2002) AtPIN4 mediates sink-driven auxin gradients and root patterning in *Arabidopsis*. Cell 108: 661-673

Fujisawa Y, Kato H, Iwasaki Y (2001) Structure and function of heterotrimeric G proteins in plants. Plant Cell Physiol 42: 789-794.

Gallagher, S. R. (1992) Quantitation of Gus activity by fluorometry. In GUS Protocols: using the GUS gene as a reporter of gene expression (Gallagher, S. R., ed): Academic Press, Inc., New York, pp. 47-59.

Gallie, D. R., Sleat, D. E., Watts, J. W., Turner, P. C. and Wilson, T. M. (1987) The 5'-leader sequence of tobacco mosaic virus RNA enhances the expression of foreign gene transcripts in vitro and in vivo. Nucleic Acids Res 15: 3257-3273.

Gleave, A. P. (1992) A versatile binary vector system with a T-DNA organisational structure conducive to efficient integration of cloned DNA into the plant genome. Pl. Molec. Bio. 20: 1203-1207.

Gomez-Gomez L, Boiler T (2000) FLS2: an LRR receptor-like kinase involved in the perception of the bacterial elicitor flagellin in *Arabidopsis*. Mol Cell 5: 1003-1011

Gomez-Gomez L, Boiler T (2002) Flagellin perception: a paradigm for innate immunity. Trends Plant Sci 7: 251-256

Guan X, Stege J, Kim M, Dahmani Z, Fan N, Heifetz P, Barbas C F, 3rd, Briggs S P (2002) Heritable endogenous gene regulation in plants with designed polydactyl zinc finger transcription factors. Proc Natl Acad Sci USA 99:13296-13301

Guo, H. S., Fei, J. F., Xie, Q. and Chua, N. H. (2003) A chemical-regulated inducible RNAi system in plants. Plant J, 34, 383-392.

Haussuhl, K., Andersson, B. and Adamska, I. (2001) A chloroplast DegP2 protease performs the primary cleavage of the photodamaged D1 protein in plant photosystem II. Embo J 20; 713-722.

He Z, Wang Z Y, Li J, Zhu Q, Lamb C, Ronald P, Chory J (2000) Perception of brassinosteroids by the extracellular domain of the receptor kinase BRI1. Science 288: 2360-2363.

Helling a H. W. and Richards, F. M. (1991). Construction of new ligand binding sites in proteins of known structure. I. Computer-aided modeling of sites with pre-defined geometry. J. Mol. Biol. 222:763-785.

Holt, N. E., Zigmantas, D., Valkunas, L., Li, X. P., Niyogi, K. K. and Fleming, G. R. (2005) Carotenoid cation formation and the regulation of photosynthetic light harvesting. Science 307; 433-436.

Hortensteiner S, Wuthrich K L, Matile P, Ongania K H, Krautler B (1998) The key step in chlorophyll breakdown in higher plants. Cleavage of pheophorbide a macrocycle by a monooxygenase. J Biol Chem 273: 15335-15339

Huppert, H. (2004) Making the UK safer: detecting and decontaminating chemical and biological agents. London: The Royal Society, pp. 1-51.

Kakimoto, T. (1996) CKI1, a histidine kinase homolog implicated in cytokinin signal transduction. Science 274:982-985.

Kakimoto, T. (2003) Perception and signal transduction of cytokinins. Annu Rev Plant Biol. 54:605-627.

Kieselbach, T. and Schroder, W. P. (2003) The proteome of the chloroplast lumen of higher plants. Photosynth Res 78; 249-264.

Koretke. K. K., Lupas, A. N., Warren, P. V., Rosenberg, M. and Brown, J. R. (2000) Evolution of two-component signal transduction. Mol Biol. Evol. 17:1956-1970.

Larkin, R. M., Alonso, J. M., Ecker, J. R. and Chory, J. (2003) GUN4, a Regulator of Chlorophyll Synthesis and Intracellular Signaling. Science 299: 902-906.

Li, X. P., Gilmore, A. M., Caffarri, S., Bassi, R., Golan, T., Kramer, D. and Niyogi, K. K. (2004) Regulation of photosynthetic light harvesting involves intrathylakoid lumen pH sensing by the PsbS protein. J Biol Chem 279: 22866-22874.

Li, L., Shakhnovich, E. I. and Mirny, L. A. (2003) Amino acids determining enzyme-substrate specificity in prokaryotic and eukaryotic protein kinases. Proc Natl Acad Sci USA 100: 4463-4468.

Li J, Chory J (1997) A putative leucine-rich repeat receptor kinase involved in brassinosteroid signal transduction. Cell 90: 929-938

Littlewood T D, Hancock D C, Danielian P S, Parker M G, Evan G I (1995) A modified oestrogen receptor ligand-binding domain as an improved switch for the regulation of heterologous proteins. Nucleic Acids Res 23: 1686-1690

Liu Q, Segal D J, Ghiara J B, Barbas C F, 3rd (1997) Design of polydactyl zinc-finger proteins for unique addressing within complex genomes. Proc Natl Acad Sci USA 94: 5525-5530

Lloyd, A. M., Walbot, V. and Davis, R. W. (1992) *Arabidopsis* and *Nicotiana* anthocyanin production activated by maize regulators R and C1. Science 258: 1773-1775.

Loeffler, C., Berger, S., Guy, A., Durand, T., Bringmann, G., Dreyer, M., von Rad, U., Durner, J. and Mueller, M. J. (2005) B1-phytoprostanes trigger plant defense and detoxification responses. Plant Physiol 137: 328-340.

Looger, L. L., Dwyer, M. A., Smith, J. J. and Helling a, H. W. (2003) Computational design of receptor and sensor proteins with novel functions. Nature 423: 185-190.

Mach J M, Castillo A R, Hoogstraten R, Greenberg J T (2001) The *Arabidopsis*-accelerated cell death gene ACD2 encodes red chlorophyll catabolite reductase and suppresses the spread of disease symptoms. Proc Natl Acad Sci USA 98: 771-776

Malkin R, Niyogi K (2000) Photosynthesis. In B Buchanan, W Gruissem, R I Jones, eds, Biochemistry and Molecular Biology of Plants. American Society of Plant Physiologists, Rockville, Md., pp 568-629

Marvin J S, Helling a H W (2001) Conversion of a maltose receptor into a zinc biosensor by computational design. Proc Natl Acad Sci USA. 98(9):4955-60.

Masuda, T., Fusada, N., Oosawa, N., Takamatsu, K., Yamamoto, Y. Y., Ohto, M., Nakamura, K., Goto, K., Shibata, D., Shirano, Y., Hayashi, H., Kato, T., Tabata, S., Shimada, H., Ohta, H. and Takamiya, K. (2003) Functional analysis of isoforms of NADPH: protochlorophyllide oxidoreductase (POR), PORB and PORC, in *Arabidopsis thaliana*. Plant Cell Physiol 44: 963-974

Matile P, Hortensteiner S, Thomas H (1999) Chlorophyll Degradation. Ann. Rev. Plant Physiol. 50: 67-95.

Maxwell, K. and Johnson, G. N. (2000) Chlorophyll fluorescence—a practical guide. J Exp Bot 51: 659-668.

McDaniel, R. and Weiss, R. (2005) Advances in synthetic biology: on the path from prototypes to applications. Current Opin. Biotech. 16: 476-483.

McManus M T, Sharp P A (2002) Gene silencing in mammals by small interfering RNAs. Nat Rev Genet 3: 737-747.

Mittler, R., Vanderauwera, S., Gollery, M. and Van Breusegem, F. (2004) Reactive oxygen gene network of plants. Trends Plant Sci 9: 490-498.

Murashige, T. and Skoog, F. (1962) A revised medium for rapid growth and bioassays with tobacco tissue cultures. Physiol Plantarum 15: 473-497.

Nedbal, L. and Brezina, V. (2002) Complex metabolic oscillations in plants forced by harmonic irradiance. Biophys J 83: 2180-2189.

Nedbal, L., Brezina, V., Adamec, F., Stys, D., Oja, V., Laisk, A. and Govindjee (2003) Negative feedback regulation is responsible for the non-linear modulation of photosynthetic activity in plants and cyanobacteria exposed to a dynamic light environment. Biochim Biophys Acta 1607: 5-17.

Odell, J. T., Nagy, F. and Chua, N. H. (1985) Identification of DNA sequences required for activity of the cauliflower mosaic virus 35S promoter. Nature 313: 810-812.

Oosawa N, Masuda T, Awai K, Fusada N, Shimada H, Ohta H, Takamiya K (2000) Identification and light-induced expression of a novel gene of NADPH-protochlorophyllide oxidoreductase isoform in *Arabidopsis*. FEBS Lett 474: 133-136

Ordiz M I, Barbas C F, 3rd, Beachy R N (2002) Regulation of transgene expression in plants with polydactyl zinc finger transcription factors. Proc Natl Acad Sci USA 99:13290-13295

Pattanayak G K, Tripathy B C (2002) Catalytic function of a novel protein protochlorophyllide oxidoreductase C of *Arabidopsis thaliana*. Biochem Biophys Res Commun 291: 921-924

Padidam, M. and Cao, Y. (2001) Elimination of transcriptional interference between tandem genes in plant cells. Biotechnology 31: 328-330, 332-324.

Porra, R. J., Thompson, W. A. and Kriedemann, P. E. (1989) Determination of accurate extinction coefficients and simultaneous equations for assaying chlorophylls a and b extracted with four different solvents: verification of the concentration of chlorophyll standards by atomic absorption spectroscopy. Biochim Biophys Acta 975: 384-394.

Pruzinska, A., Tanner, G., Anders, I., Roca, M. and Hortensteiner, S. (2003) Chlorophyll breakdown: pheophorbide a oxygenase is a Rieske-type iron-sulfur protein, encoded by the accelerated cell death 1 gene. Proc Natl Acad Sci USA 100: 15259-15264.

Pruzinska, A., Tanner, G., Aubry, S., Anders, I., Moser, S., Muller, T., Ongania, K. H., Krautler, B., Youn, J. Y., Liljegren, S. J. and Hortensteiner, S. (2005) Chlorophyll breakdown in senescent *Arabidopsis* leaves. Characterization of chlorophyll catabolites and of chlorophyll catabolic enzymes involved in the degreening reaction. Plant Physiol 139: 52-63.

Ptashne M (1997) Control of gene transcription: an outline. Nat Med 3: 1069-1072

Romanov, G A, Kieber, J. J., Schmulling, T. (2002) A rapid cytokinin response assay in *Arabidopsis* indicates a role for phospholipase D in cytokinin signaling. FEBS Lett 27:39-43

Rushton P J, Reinstadler A, Lipka V, Lippok B, Somssich I E (2002) Synthetic plant promoters containing defined regulatory elements provide novel insights into pathogen- and wound-induced signaling. Plant Cell 14: 749-762

Rushton P J, Somssich I E (1998) Transcriptional control of plant genes responsive to pathogens. Curr Opin Plant Biol 1: 311-315

Rushton P J, Torres J T, Parniske M, Wernert P, Hahlbrock K, Somssich I E (1996) Interaction of elicitor-induced DNA-binding proteins with elicitor response elements in the promoters of parsley PR1 genes. Embo J 15: 5690-5700

Saeed, A. I., Sharov, V., White, J., Li, J., Liang, W., Bhagabati, N., Braisted, J., Klapa, M., Currier, T., Thiagarajan, M., Sturn, A., Snuffin, M., Rezantsev, A., Popov, D., Ryltsov, A., Kostukovich, E., Borisovsky, I., Liu, Z., Vinsavich, A., Trush, V. and Quackenbush, J. (2003) TM4: a free, open-source system for microarray data management and analysis. Biotechnology 34: 374-378.

Safadi F, Reddy V S, Reddy A S (2000) A pollen-specific novel calmodulin-binding protein with tetratricopeptide repeats. J Biol Chem 275: 35457-35470

Sakai, H., Aoyama, T. and Oka, A. (2000) *Arabidopsis* ARR1 and ARR2 response regulators operate as transcriptional activators. Plant J 24: 703-711.

Sanger, M., Daubert, S, and Goodman, R. M. (1990) Characteristics of a strong promoter from figwort mosaic virus: comparison with the analogous 35S promoter from cauliflower mosaic virus and the regulated mannopine synthase promoter. Plant Mol Biol 14: 433-443.

Segal, D. J., Stege, J. T. and Barbas, C. F., 3rd (2003) Zinc fingers and a green thumb: manipulating gene expression in plants. Curr Opin Plant Biol 6: 163-168.

Segal D J, Barbas C F, 3rd (2001) Custom DNA-binding proteins come of age: polydactyl zinc-finger proteins. Curr Opin Biotechnol 12: 632-637

Segal D J, Dreier B, Beerli R R, Barbas C F, 3rd (1999) Toward controlling gene expression at will: selection and design of zinc finger domains recognizing each of the 5'-GNN-3' DNA target sequences. Proc Natl Acad Sci USA 96: 2758-2763.

Smith N A, Singh S P, Wang M B, Stoutjesdijk P A, Green A G, Waterhouse P M (2000) Total silencing by intron-spliced hairpin RNAs. Nature 407: 319-320.

Somerville, C., Bauer, S., Brininstool, G., Facette, M., Hamann, T., Milne, J., Osborne, E., Paredez, A., Persson, S., Raab, T., Vorwerk, S, and Youngs, H. (2004) Toward a systems approach to understanding plant cell walls. 306:2206-1211.

Song W Y, Wang G L, Chen L L, Kim H S, Pi L Y, Holsten T, Gardner J, Wang B, Zhai W X, Zhu L H, et al. (1995) A receptor kinase-like protein encoded by the rice disease resistance gene, Xa21. Science 270: 1804-1806

Stege, J. T., Guan, X., Ho, T., Beachy, R. N. and Barbas, C. F., 3rd (2002) Controlling gene expression in plants using synthetic zinc finger transcription factors. Plant J 32: 1077-1086.

Stobart, A. K. and Hendry, G. A. F. (1984) The turnover of chlorophyll in greening wheat leaves. Phytochem. 23: 27-30.

Stock, A. M., Robinson, V. L. and Goudreau, P. N. (2000) Two-component signal transduction. Annu Rev Biochem. 69:183-215.

Stoutjesdijk P A, Singh S P, Liu Q, Hurlstone C J, Waterhouse P A, Green A G (2002) hpRNA-Mediated Targeting of the *Arabidopsis* FAD2 Gene Gives Highly Efficient and Stable Silencing. Plant Physiol 129: 1723-1731.

Swartz, J. R. (2001) Curr. Opin. Biotechnol. 12:195-201.

Takamiya K I, Tsuchiya T, Ohta H (2000) Degradation pathway(s) of chlorophyll: what has gene cloning revealed? Trends Plant Sci 5: 426-431

Thomas H, Ougham H, Canter P, Donnison I (2002) What stay-green mutants tell us about nitrogen remobilization in leaf senescence. J Exp Bot 53: 801-808

Torii K U (2000) Receptor kinase activation and signal transduction in plants: an emerging picture. Curr Opin Plant Biol 3: 361-367

Torii K U, Mitsukawa N, Oosumi T, Matsuura Y, Yokoyama R, Whittier R F, Komeda Y (1996) The *Arabidopsis* ERECTA gene encodes a putative receptor protein kinase with extracellular leucine-rich repeats. Plant Cell 8: 735-746

Trewavas A (2000) Signal Perception and Transduction. In B Buchanan, W Gruissem, R Jones, eds, Biochemistry & Molecular Biology of Plants. American Society of Plant Physiologist, Rockville, Md., pp 930-987

Trewavas A (2002) Plant cell signal transduction: the emerging phenotype. Plant Cell 14 Suppl: S3-4

Tsuchiya T, Ohta H, Okawa K, Iwamatsu A, Shimada H, Masuda T, Takamiya K (1999) Cloning of chlorophyllase, the key enzyme in chlorophyll degradation: finding of a lipase motif and the induction by methyl jasmonate. Proc Natl Acad Sci USA 96: 15362-15367.

VanBogelen, R. A., Olson, E. R., Wanner, B. L., Neidhardt, F. C., Global analysis of proteins synthesized during phosphorous restriction in *Escherichia coli* (1996) J. Bacteriol. 176:4344-4366.

Verdecia, M. A., Larkin, R. M., Ferrer, J. L., Riek, R., Chory, J. and Noel, J. P. (2005) Structure of the Mg-chelatase cofactor GUN4 reveals a novel hand-shaped fold for porphyrin binding. PLoS Biol 3: e151.

Walker, J. M and Vierstra, R. D. (2007) A ubiquitin-based vector for the co-ordinated systhesis of multiple proteins in plants. Plant Biotechnol. 5:413-421.

Walthers, D., Tran, V. K., Kenney, L. J (2003) Interdomain linkers of homologous response regulators determine their mechanism of action. J. Bacteriol. 185:317-324.

Wang M B, Waterhouse P M (2002) Application of gene silencing in plants. Curr Opin Plant Biol 5: 146-150

Wang Z Y, Seto H, Fujioka S, Yoshida S, Chory J (2001) BRI1 is a critical component of a plasma-membrane receptor for plant steroids. Nature 410: 380-383

Wang Z Y, Seto H, Fujioka S, Yoshida S, Chory J (2001) BRI1 is a critical component of a plasma-membrane receptor for plant steroids. Nature 410: 380-383

Waterhouse P M, Smith N A, Wang M B (1999) Virus resistance and gene silencing: killing the messenger. Trends in Plant Science 4: 452-447

Weaver, L. M. and Amasino, R. M. (2001) Senescence is induced in individually darkened *Arabidopsis* leaves, but inhibited in whole darkened plants. Plant Physiol 127: 876-886.

Welsey V, Helliwell C, Smith N, Wang M B, Rouse D, Liu Q, Gooding P, Singh S, Abbott D, Stoutjesdijk P, Robinson S P, Gleave A G, Green A G, Waterhouse P M (2001) Construct design for efficient, effective and high throughput gene silencing in plants. Plant J. 27: 581-590

West, J. S., Bravo, C., Oberti, R., Lemaire, D., Moshou, D. and McCartney, H. A. (2003) The potential of optical canopy measurement for targeted control of field crop diseases. Annual Review of Phytopathology 41: 593-614.

Wuthrich K L, Bovet L, Hunziker P E, Donnison I S, Hortensteiner S (2000) Molecular cloning, functional expression and characterisation of RCC reductase involved in chlorophyll catabolism. Plant J 21: 189-198

Zarco-Tejada, P. J., Miller, J. R., Mohammed, G. H., Noland, T. L. and Sampson, P. H.

(2002) Vegetation stress detection through chlorophyll a+b estimation and fluorescence effects on hyperspectral imagery. J Environ Qual 31: 1433-1441.

Zelisko, A., Garcia-Lorenzo, M., Jackowski, G., Jansson, S, and Funk, C. (2005) AtFtsH6 is involved in the degradation of the light-harvesting complex II during high-light acclimation and senescence. Proc Natl Acad Sci USA 102: 13699-13704.

Zuo J, Niu Q W, Chua N H (2000) An estrogen receptor-based transactivator XVE mediates highly inducible gene expression in transgenic plants. Plant J 24: 265-273

Zuo J, Niu Q W, Chua N H (2000) Technical advance: An estrogen receptor-based transactivator XVE mediates highly inducible gene expression in transgenic plants. Plant J 24: 265-273.

What is claimed is:

1. A plant cell comprising:
   a first DNA construct comprising a first promoter functional in a plant operably linked to a recombinant nucleic acid encoding a first repressor;
   a second DNA construct comprising a second promoter functional in a plant operably linked to a nucleic acid encoding a detectable marker or response gene, wherein said second promoter is repressible by a second repressor, and
   a third DNA construct comprising a third promoter functional in a plant operably linked to a nucleic acid encoding said first repressor;
   wherein said third promoter is constitutive and repressible by said second repressor, wherein said first repressor or second repressor comprise at least one EAR1 or EAR 2 repressor domain.

2. The plant cell of claim 1, further comprising a fourth DNA construct comprising a fourth promoter operable in a plant operably linked to a nucleic acid encoding said second repressor, wherein said fourth promoter is constitutive and repressible.

3. The plant cell of claim 2, wherein said fourth promoter is repressible by said first repressor.

4. The plant cell of claim 3, wherein repression of said fourth promoter by said first repressor reduces expression of said second repressor.

5. The plant cell of claim 4, wherein reduced expression of said second repressor increases expression of said detectable marker or response gene.

6. The plant cell of claim 3, wherein said fourth promoter is a recombinant polynucleotide comprising nucleic acid sequence from a non-plant organism.

7. The plant cell of claim 1, wherein said nucleic acid encoding said first repressor is a recombinant polynucleotide.

8. The plant cell of claim 7, wherein said nucleic acid encoding said first repressor comprises nucleic acid sequences encoding at least one GAL4 DNA binding domain.

9. The plant cell of claim 2, wherein said nucleic acid encoding said second repressor is a recombinant polynucleotide.

10. The plant cell of claim 1, wherein said first promoter is a recombinant polynucleotide.

11. The plant cell of claim 10, wherein said first promoter comprises the polynucleotide sequence of SEQ ID NO:1.

12. The plant cell of claim 10, wherein said first promoter is induced by a transcription activator protein activated by an external signal.

13. The plant cell of claim 12, wherein said transcription activator protein is a fusion protein encoded by a polynucleotide sequence derived from a non-plant organism.

14. The plant cell of claim 13, wherein said polynucleotide sequence encoding said fusion protein comprises at least one nucleic acid sequence encoding a PhoB binding domain.

15. The plant cell of claim 14, wherein said PhoB domain recognizes SEQ ID NO:14.

16. The plant cell of claim 14, wherein said fusion protein is encoded by a polynucleotide sequence comprising a nucleic acid sequence encoding a polypeptide sequence of VP64.

17. The plant cell of claim 13, wherein said fusion protein is encoded by a polynucleotide sequence selected from the group consisting of SEQ ID NO:4, SEQ ID NO:5, SEQ ID NO:6 or SEQ ID NO:11.

18. The plant cell of claim 12, further comprising a fifth DNA construct comprising a plant operable promoter operably linked to a nucleic acid sequence encoding a sensor protein that recognizes said external signal.

19. The plant cell of claim 18, wherein said nucleic acid sequence comprises SEQ ID NO:8.

20. The plant cell of claim 1, wherein said second promoter is a recombinant polynucleotide.

21. A transgenic plant comprised of plant cells according to claim 1.

22. A method for detecting an external signal, said method comprising the step of exposing the transgenic plant or plant cell of claim 21 to an external signal and detecting a change resulting from expression of said detectable marker or response gene.

23. The method of claim 22, wherein said expression of said detectable marker or response gene increases in response to reduced expression of said second repressor resulting from increased expression of said first repressor in response to said external signal.

24. The method of claim 23, wherein said detectable marker or response gene comprises a nucleic acid encoding at least one of an RNA interfering molecule that inhibits expression of a chlorophyll biosynthesis coding sequence, a chlorophyll degradation enzyme, a glucuronidase, a β-galactosidase, a luciferase, a green fluorescent protein, or yellow fluorescent protein.

25. The method of claim 22, wherein said change is degreening of said transgenic plant or plant cell.

26. The method of claim 25, wherein said degreening of the transgenic plant or plant cell is detected visually or by detecting properties selected from the group consisting of chlorophyll fluorescence, photosynthetic properties and properties related to reactive oxygen species and their damage.

27. The method of claim 22, wherein said external signal is detectable after a single exposure of said transgenic plant or plant cell to said external signal.

28. The method of claim 27, wherein detection of said external signal after a single exposure results from increased expression of said first repressor.

29. The method of claim 28, wherein increased expression of said first repressor results from repression of a fourth modified promoter operably linked to a nucleic acid sequence encoding said second repressor.

30. The method of claim 22, wherein said change is not detectable in the absence of said external signal.

31. The plant cell of claim 7, wherein said nucleic acid encoding said second repressor comprises nucleic acid sequences encoding at least one LexA DNA binding domain and at least one EAR2 repressor domain.

\* \* \* \* \*

SEQUENCE LISTING

```
<160> NUMBER OF SEQ ID NOS: 41

<210> SEQ ID NO 1
<211> LENGTH: 223
<212> TYPE: DNA
<213> ORGANISM: Artificial
<220> FEATURE:
<223> OTHER INFORMATION: (PlantPho): 4 Pho boxes from Escherichia Coli
      and a Cauliflower Mosaic Virus sequence (-46)

<400> SEQUENCE: 1
gagctcgttt aaacgggccc gtcgacctgt cataaatctg tcacaaatct gtcataaatc     60
tgtcacaaat ctgtcataaa tctgtcacaa atctgtcata aatctgtcac aaacgcaaga    120
cccttcctct atataaggaa gttcatttca tttggagagg gacgtcgcgg ccgcctgcag    180
ttaattaagg taccggcgcg ccatttaaat cgggcccaag ctt                      223

<210> SEQ ID NO 2
<211> LENGTH: 1578
<212> TYPE: DNA
<213> ORGANISM: Artificial
<220> FEATURE:
<223> OTHER INFORMATION: (FLS-Trg-DHP8-PhoR): Bacterial sequences from
      Escherichia Coli

<400> SEQUENCE: 2
atgaagttac tctcaaagac cttttgata ttaactctca ccttcttctt ctttggcatt      60
gcactagcga aaatgaatac aactccctca cagcgattag gttttttgca tcacatcagg    120
ttggttccgt tatttgcctg cattctaggc ggtatcttag ttctattcgc attaagttca    180
gccctggctg gctatttcct ctggcaggcc gatcgcgatc agcgtgatgt tactgcggag    240
attgagattc ggaccgggtt agcgaacagt tcagattttt tgcgttcagc ccggatcaat    300
atgattcagg ccggggctgc gagtcgtatt gcggaaatgg aagcaatgaa gcgaaatatt    360
gcgcaagccg aatcggagat taaacagtcg cagcaaggtt atcgtgctta tcagaatcga    420
ccggtgaaaa cacctgctga tgaagccctc gacactgaat taaatcaacg ctttcaggct    480
tatatcacgg gtatgcaacc tatgttgaaa tatgccaaaa atggcatgtt tgaagcgatt    540
atcaatcatg aaagtgagca gatccgaccg ctggataatg cttataccga tatttttgaac   600 aaagccgtta agatacgtag caccagagcc aaccaactgg cggaactggc ccatcagcgc    660
acccgcctgg gtgggatgtt catgattggc gcgtttgtgc ttgccctggt catgacgctg    720
ataacattta tggtgctacg tcggatcgtc attcgtccac tgcaacatgc cgcacaacgg    780
attgaaaaaa tcgccagtgg cgatctgacg atgaatgatg aaccggcggg tcgtaatgaa    840
atcggtcgct taagtcgtca tttacagcat atgcatcaac tggaaggggc gcggcgtaac    900
ttttttgcca acgtgagcca tgagttacgt acgccattga ccgtgttaca gggttacctg    960
gagatgatga tgagcagcc gctggaaggc gcggtacgcg aaaaagcgtt gcacaccatg   1020
cgcgagcaga cccagcggat ggaaggactg gtgaagcaat tgctgacgct gtcgaaaata   1080
```

```
gaagccgcac cgacgcattt gctcaatgaa aaggttgatg tgccgatgat gctgcgcgtt   1140
gttgagcgcg aggctcagac tctgagtcag aaaaaacaga catttacctt tgagatagat   1200
aacggcctca aggtgtctgg caacgaagat cagctacgca gtgcgatttc gaacctggtc   1260
tataacgccg tgaatcatac gccggaaggc acgcatatca ccgtacgctg cagcgagtg    1320 ccgcacggtg ccgaatttag cgttgaagat aacggaccgg gcattgcacc ggagcatatt   1380
ccgcgcctga ccgagcgttt ttatcgcgtt gataaagcgc gttcccggca accggcggt    1440 agcggattag ggttagcgat cgtgaaacat gctgtgaatc atcacgaaag tcgcctgaat   1500
attgagagta cagtaggaaa aggaacacgt ttcagttttg ttatcccgga acgtttaatt   1560
gccaaaaaca gcgattaa                                                 1578

<210> SEQ ID NO 3
<211> LENGTH: 1578
<212> TYPE: DNA
<213> ORGANISM: Artificial
<220> FEATURE:
<223> OTHER INFORMATION: (AtFLS-Trg-DHP8-PhoR): Bacterial sequences from
      Escherichia Coli

<400> SEQUENCE: 3
atgaagttac tatccaaaac cttcttgatc ttaaccttaa cttttttctt cttcggtatc      60
gcgctcgcca aaatgaatac gaccccttct caaaggcttg gatttcttca tcatatcaga     120
cttgttccac ttttttgcttg tatactcgga ggtattctcg ttctgttcgc tttgtcttct    180
gcgttagctg gtactttcct atggcaggct gataggatc aacgggatgt aacggcagag      240
attgaaatta gaactggtct tgctaactct agcgattttc tcaggtctgc aagaataaac     300
atgattcaag caggagctgc aagccggata gcagaaatgg aagcgatgaa gcgtaacatt     360
gcccaggctg aatctgaaat taaacaatcg cagcaaggtt acagagcgta ccaaaatcga     420
cccgtaaaaa caccggcaga cgaagcgctc gacaccgaac ttaatcaacg gtttcaggca     480
tatatcactg ggatgcaacc aatgttgaag tacgctaaaa acggtatgtt cgaagctatt     540
atcaaccatg aatcggagca ataagacca cttgacaacg catacacgga cattttgaat     600
aaagctgtta aaattagatc tactcgtgca aaccaactcg cagaattggc acatcagagg     660
acgagactag gcggaatgtt catgattggt gcattcgtgc tggctcttgt tatgacgtta     720 ataacttta tggtcctacg tagaatcgtt attagaccac ttcagcacgc tgcacagaga      780
attgaaaaaa ttgcatctgg agatttaaca atgaacgatg agccagcagg aaggaatgag     840
attggtaggc tcagtagaca tctccaacag atgcatcaat tggaaggagc acgcaggaat     900
ttttttgcaa atgtatctca cgaattgaga acgcctctta cagtacttca aggatacctc     960
gagatgatga cgagcagcc actggaagga gctgtccgag agaaggcgtt acatactatg     1020
agagaacaga ctcaacggat ggagggactc gttaagcaac tgctcactct ctcaaaaatc    1080
gaggcggcac cgactcatct tctcaacgag aaggttgatg ttcccatgat gttacgggta    1140
gtagagaggg aagctcaaac attgtctcaa aaaaagcaaa cctttacgtt cgaaattgac    1200
aatgggttga agtaagcgg taatgaggat caattgagga cgctatatc gaatcttgtt      1260 tacaatgcag taaccacac cccagaaggt actcatatta cagttcgttg cagcgtgtg      1320 ccacatggtg cagaatttag cgtcgaagat aatggtccgg gaattgctcc agagcatatt    1380
cctcggctga ctgagaggtt ttacagggtt gataaagctc ggtctcgcca gacaggaggt    1440
tcggggttag ggcttgcaat agttaaacac gccgtgaatc accatgagtc aagattgaac    1500
```

```
atcgagtcaa ccgtgggaaa gggaacacgt ttcagctttg taattcctga aagacttata    1560
gctaagaact cagattaa                                                  1578

<210> SEQ ID NO 4
<211> LENGTH: 849
<212> TYPE: DNA
<213> ORGANISM: Artificial
<220> FEATURE:
<223> OTHER INFORMATION: (PhoB-VP64): PhoB from Escherichia Coli and
      VP64 from Herpes Simplex Virus

<400> SEQUENCE: 4
atggcgagac gtattctggt cgtagaagat gaagctccaa ttcgcgaaat ggtctgcttc      60
gtgctcgaac aaaatggctt tcagccggtc gaagcggaag attatgacag tgctgtgaat     120
caactgaatg aaccctggcc ggatttaatt ctcctcgact ggatgttacc tggcggctcc     180
ggtatccagt tcatcaaaca cctcaagcgc gagtcgatga cccgggatat tccagtggtg     240
atgttgaccg ccagagggga agaagaagat cgcgtgcgcg gccttgaaac cggcgcggat     300
gactatatca ccaagccgtt ttcgccgaag gagctggtgg cgcgaatcaa agcggtaatg     360
cgccgtattt cgccaatggc ggtggaagag gtgattgaga tgcagggatt aagtctcgac     420
ccgacatctc accgagtgat ggcgggcgaa gagccgctgg agatggggcc gacagaattt     480
aaactgctgc actttttat gacgcatcct gagcgcgtgt acagccgcga gcagctgtta     540
aaccacgtct ggggaactaa cgtgtatgtg aagaccgcca cggtcgatgt ccacattcgt     600
cgcctgcgta aagcactgga gcccggcggg catgaccgca tggtgcagac cgtgcgcggt     660
acaggatatc gttttcaac ccgctttgcc gacgcgctgg acgatttcga tctcgacatg     720
ctgggttctg atgccctcga tgactttgac ctggatatgt tgggaagcga cgcattggat     780
gactttgatc tggacatgct cggctccgat gctctggacg atttcgatct cgatatgtta     840
ggttcctag                                                             849

<210> SEQ ID NO 5
<211> LENGTH: 849
<212> TYPE: DNA
<213> ORGANISM: Artificial
<220> FEATURE:
<223> OTHER INFORMATION: (AtPhoB-VP64): PhoB from Escherichia Coli and
      VP64 from Herpes Simplex Virus

<400> SEQUENCE: 5
atggctagaa gaatactagt agtagaagac gaggcgccta agagaaat ggtttgtttt        60 gtcctagaac aaaatggatt ccaacctgtt gaagctgaag attatgatag cgctgtcaac     120
caattaaatg aaccatggcc tgatttgatt ttacttgact ggatgttgcc tggaggaagc     180
ggaatacaat ttataaaaca tttgaaacga gaaagtatga caagagacat acctgtggtt     240
atgttgactg caagaggaga ggaagaagat agagtacgag gattgaaaac gggagctgat     300
gactatataa caaaaccatt ttcaccaaag gaactagtag caagaataaa ggctgtaatg     360
cgaagaatta gcccaatggc agtagaagaa gtaatagaaa tgcagggact cagtttagat     420
ccgacatctc atagagttat ggctggaaga gaaccactgg aaatggggcc aacagaattt     480
aagttactac attttttat gacccaccca gaaagagttt acagtagaga caacttttg      540 aatcacgttt ggggaaccaa tgtttatgtt gaagaccgta cagtgatgt tcatataaga     600 cgactaagaa aagcactcga accaggagga catgataaa tggttcaaac agtaagagga     660
actggatata gattttcaac acgttttgcc gatgccctcg acgattttga cttagatatg     720
```

```
cttggaagtg acgccttaga tgattttgat ttggatatgt taggaagcga tgcgttggat    780
gattttgatt tagatatgct tgggagtgat gctttagacg attttgatct agatatgtta    840
ggttcttaa                                                            849
```

<210> SEQ ID NO 6
<211> LENGTH: 870
<212> TYPE: DNA
<213> ORGANISM: Artificial
<220> FEATURE:
<223> OTHER INFORMATION: (OmpR-VP64): OmpR from Escherichia Coli and
      VP64 from Herpes Simplex Virus

<400> SEQUENCE: 6

```
atgcaagaga actacaagat tctggtggtc gatgacgaca tgcgcctgcg tgcgctgctg    60
gaacgttatc tcaccgaaca aggcttccag gttcgaagcg tcgctaatgc agaacagatg    120
gatcgcctgc tgactcgtga atctttccat cttatggtac tggatttaat gttacctggt    180
gaagatggct tgtcgatttg ccgacgtctt cgtagtcaga gcaacccgat gccgatcatt    240
atggtgacgg cgaaagggga agaagtggac cgtatcgtag gcctggagat tggcgctgac    300
gactacattc aaaaaccgtt taacccgcgt gaactgctgg cccgtatccg tgcggtgctg    360
cgtcgtcagg cgaacgaact gccaggcgca ccgtcacagg aagaggcggt aattgctttc    420
ggtaagttca aacttaacct cggtacgcgc gaaatgttcc gcgaagacga gccgatgccg    480
ctcaccagcg gtgagtttgc ggtactgaag gcactggtca gccatccgcg tgagccgctc    540
tcccgcgata agctgatgaa ccttgcccgt ggtcgtgaat attccgcaat ggaacgctcc    600
atcgacgtgc agatttcgcg tctgcgccgc atggtggaag aagatccagc gcatccgcgt    660
tacattcaga ccgtctgggg tctgggctac gtctttgtac cggacggctc taaagcattg    720
gatgatttcg atttagatat gcttgggagt gatgctctcg atgattttga tcttgatatg    780
cttggatcag atgctcttga tgatttcgat tggacatgc ttggatctga tgctttagat    840
gatttcgatc ttgatatgct tggttcatag                                    870
```

<210> SEQ ID NO 7
<211> LENGTH: 900
<212> TYPE: DNA
<213> ORGANISM: Artificial
<220> FEATURE:
<223> OTHER INFORMATION: (ssTNT): Synthetic nucleotide derived from the
      bacterial protein RBP (ribose binding protein)

<400> SEQUENCE: 7

```
atggagaggc cctttggctg cttcttcatc ctccttctta tctcctatac cgtcgtggcc    60
aaagacacca tcgcgctggt ggtctccacg cttaactctc cgttccttgt atcgctgaaa    120
gatggcgcgc agaaagaggc ggataaactt ggctataacc tggtggtgct ggactcccag    180
aacaacccgg cgaaagagct ggcgaacgtg caggacttaa ccgttcgcgg cacaaaaatt    240
ctgctgatta acccgaccga ctccgacgca gtgggtaatg ctgtgaagat ggctaaccag    300
gcgaacatcc cggttatcac tctttcttct caggcaacga aggtgaagt ggtgagccac    360 attgcttctg ataacgtact gggcggcaaa atcgctggta ttacatcgc gaagaaagcg    420 ggtgaaggtg ccaaagttat cgagctgcaa ggcattgctg gtacatcctc tgcccgtgaa    480
tcaggcgaag gcttccagca ggccgttgct gctcacaagt ttaatgttct tgccagccag    540
ccagcagata ttgatcgcat taaggtttg aacgtaatgc agaacctgtt gaccgctcat    600
```

```
ccggatgttc aggctgtatt cgcgcagttt gatgaaatgg cgctgggcgc gctgcgcgca    660
ctgcaaactg ccggtaaatc ggatgtgatg gtcgtcggat tttctggtac accggatggc    720
gaaaaagcgg tgaatgatgg caaactagca gcgactatcg cttcactacc cgatcagatt    780
ggcgcgaaag gcgtcgaaac cgcagataaa gtgctgaaag gcgagaaagt tcaggctaag    840
tatccggttg atctgaaact ggttgttaag caggactaca aggatgacga tgacaagtag    900
```

<210> SEQ ID NO 8
<211> LENGTH: 900
<212> TYPE: DNA
<213> ORGANISM: Artificial
<220> FEATURE:
<223> OTHER INFORMATION: (AtssTNT): Synthetic nucleotide derived from
      the bacterial protein RBP (ribose binding protein)

<400> SEQUENCE: 8

```
atggagagac cattcgggtg tttcttcatc ctcttgttga ttagctacac tgttgtggct     60
aaagatacaa ttgcacttgt agtttctacc ttgaactccc cttcttagt ttccttaaag    120 gatggtgctc agaaagaggc tgataagctg ggatacaatc tcgttgttct tgattcacaa    180
aacaacccag ccaagaaact tgctaacgta caggatttga ctgtgagagg gactaaaatc    240
ctcttaataa acccaaccga cagcgacgca gtcggaaacg ctgtcaagat ggctaaccag    300
gcaaacatcc ctgtgattac actaagctca caagctacaa aggagaagt ggtttcgcat    360 atcgcctcag ataacgtact tggtggcaag attgctggtg attacattgc aaaaaaggct    420
ggggagggcg cgaaagtgat cgaactccag ggaattgctg ggacctcgag tgcacgagag    480
tcgggtgaag gttttcagca agctgttgct gcgcataaat ttaacgtgtt ggcttcacag    540
cccgcagaca tcgataggat caagggacta aacgtgatgc agaacttatt gacggctcat    600
ccagatgtcc aggccgtctt tgctcaattc gacgagatgg cgcttggtgc ccttcgggct    660
ttgcaaactg ccggaaaatc cgatgtgatg gtcgttggat ttagcggtac accagatggg    720
gaaaaagcag tgaatgacgg gaaactcgcg gctacgatag ctagtctccc tgatcaaata    780
ggtgcaaaag gagtggaaac agctgataag gtgcttaaag gagagaaggt tcaagctaag    840
tacccagttg atctgaaact tgttgtaaag caagattata aggatgatga tgacaaatag    900
```

<210> SEQ ID NO 9
<211> LENGTH: 2487
<212> TYPE: DNA
<213> ORGANISM: Artificial
<220> FEATURE:
<223> OTHER INFORMATION: (FLS-Trz-AHK4): Trz from Escherichia Coli and
      AHK4 from Arabidopsis thaliana

<400> SEQUENCE: 9

```
atgaagttac tctcaaagac cttttttgata ttaactctca ccttcttctt ctttggcatt     60
gcactagcga aaatgaatac aactccctca cagcgattag ttttttttgca tcacatcagg    120 ttggttccgt tatttgcctg cattctaggc ggtatcttag ttctattcgc attaagttca    180
gccctggctg gctatttcct ctggcaggcc gatcgcgatc agcgtgatgt tactgcggag    240
attgagattc ggaccgggtt agcgaacagt tcagatttt tgcgttcagc ccggatcaat    300
atgattcagg ccggggctgc gagtcgtatt gcggaaatgg aagcaatgaa gcgaaatatt    360
gcgcaagccg aatcggagat taaacagtcg cagcaaggtt atcgtgctta tcagaatcga    420
ccggtgaaaa cacctgctga tgaagccctc gacactgaat aaatcaacg ctttcaggct    480 tatatcacgg gtatgcaacc tatgttgaaa tatgccaaaa atggcatgtt tgaagcgatt    540
```

```
atcaatcatg aaagtgagca gatccgaccg ctggataatg cttataccga tattttgaac    600
aaagccgtta agatacgtag caccagagcc aaccaactgg cggaactggc ccatcagcgc    660
acccgcctgg gtgggatgtt catgattggc gcgtttgtgc ttgccctggt catgacgctg    720
ataacattta tggtgctacg tcggatcgtc attcgtccac tgcaacatgc cgcacaacgg    780
attgaaaaaa tcgccagtgg cgatctgacg atgaatgatg aaccggcggg tcgtaatgaa    840
atcggtcgct taagtcgtca tttacagcat atggcggctg gtgttaagca actggcggat    900
gaccgcacgc tgctgatggc gggggtaagt cacgacttgc gcacgccgct gacgcgtatt    960
cgcctggcga ctgagatgat gagcgagcag gatggctatc tggcagaatc gatcaataaa   1020
gatatcgaag agtgcaacgc catcattgag cagtttatcg actacctgcg caccgggcag   1080
gagatgccga tggaaatggc ggatcttaat gcagtactcg gtgaggtgat tgctgccgaa   1140
agtggctatg agcgggaaat tgaaaccgcg ctttaccccg gcagcattga agtgaaaatg   1200
cacccgctgt cgatcaaacg cgcggtggcg aatatggtgg tcaacgccgc ccgttatggc   1260
aatggctgga tcaaagtcag cagcggaacg gagccgaatc gcgcctggtt ccaggtggaa   1320
gatgacggtc cgggaattgc gccggaacaa cgtaagcacc tgttccagcc gtttgtccgc   1380
ggcgacagtg cgcgcaccat tagcggcacg ggattagggc tgagtataag caagtgtctt   1440
gttgaactta tgcgtggtca gataaatttc ataagccggc tcatattgg aagcacgttc    1500
tggttcacgg ctgtttttaga gaaatgcgat aaatgcagtg cgattaacca tatgaagaaa   1560
cctaatgtgg aacacttgcc ttctactttt aaaggaatga aagctatagt tgttgatgct   1620
aagcctgtta gagctgctgt gactagatac catatgaaaa gactcggaat caatgttgat   1680
gtcgtgacaa gtctcaaaac cgctgttgtt gcagctgctg cgtttgaaag aaacggttct   1740
cctctcccaa caaaaccgca acttgatatg atcttagtag agaaagattc atggatttca   1800
actgaagata atgactcaga gattcgttta ttgaattcaa gaaccaacgg aaacgttcat   1860
cacaagtctc cgaaactagc tctattcgca acaaacatca caaattcgga gttcgacaga   1920
gctaaatccg caggatttgc agatacggta ataatgaaac cgttaagagc aagcatgatt   1980
ggggcgtgtc tgcaacaagt tctcgagctg agaaaaacaa gacaacaaca tccagaagga   2040
tcatcacccg caactctcaa gagcttgctt acagggaaga agattcttgt ggttgatgat   2100
aatatagtta acaggagagt agctgcagga gctctcaaga aatttggagc agaagtggtt   2160
tgtgcagaga gtggtcaagt tgctttgggt ttgcttcaga ttccacacac tttcgatgct   2220
tgcttcatgg atattcaaat gccacagatg gacggatttg aagcaactcg tcagataaga   2280
atgatggaga aggaaactaa agagaagaca aatctcgaat ggcatttacc gattctagcg   2340
atgactgcgg atgtgataca cgcgacctac gaggaatgtc tgaaaagtgg gatggatggt   2400
tacgtctcca aaccttttga agaagagaat ctctataaat ccgttgccaa atcattcaaa   2460
cctaatccta tctcaccttc gtcgtaa                                       2487
```

<210> SEQ ID NO 10
<211> LENGTH: 1557
<212> TYPE: DNA
<213> ORGANISM: Artificial
<220> FEATURE:
<223> OTHER INFORMATION: (FLS-Trz): Bacterial sequences from Escherichia Coli

<400> SEQUENCE: 10

```
atgaagttac tctcaaagac cttttttgata ttaactctca ccttcttctt ctttggcatt    60
```

```
gcactagcga aaatgaatac aactccctca cagcgattag gttttttgca tcacatcagg    120
ttggttccgt tatttgcctg cattctaggc ggtatcttag ttctattcgc attaagttca    180
gccctggctg gctatttcct ctggcaggcc gatcgcgatc agcgtgatgt tactgcggag    240
attgagattc ggaccgggtt agcgaacagt tcagattttt tgcgttcagc ccggatcaat    300
atgattcagg ccggggctgc gagtcgtatt gcggaaatgg aagcaatgaa gcgaaatatt    360
gcgcaagccg aatcggagat taaacagtcg cagcaaggtt atcgtgctta tcagaatcga    420
ccggtgaaaa cacctgctga tgaagccctc gacactgaat aaatcaacg ctttcaggct     480 tatatcacgg gtatgcaacc tatgttgaaa tatgccaaaa atggcatgtt tgaagcgatt    540
atcaatcatg aaagtgagca gatccgaccg ctggataatg cttataccga tattttgaac    600
aaagccgtta agatacgtag caccagagcc aaccaactgg cggaactggc ccatcagcgc    660
acccgcctgg gtgggatgtt catgattggc gcgtttgtgc ttgccctggt catgacgctg    720
ataacattta tggtgctacg tcggatcgtc attcgtccac tgcaacatgc cgcacaacgg    780
attgaaaaaa tcgccagtgg cgatctgacg atgaatgatg aaccggcggg tcgtaatgaa    840
atcggtcgct taagtcgtca tttacagcat atggcggctg gtgttaagca actggcggat    900
gaccgcacgc tgctgatggc gggggtaagt cacgacttgc gcacgccgct gacgcgtatt    960
cgcctggcga ctgagatgat gagcgagcag gatggctatc tggcagaatc gatcaataaa    1020
gatatcgaag agtgcaacgc catcattgag cagtttatcg actacctgcg caccgggcag    1080
gagatgccga tggaaatggc ggatcttaat gcagtactcg gtgaggtgat tgctgccgaa    1140
agtggctatg agcgggaaat tgaaaccgcg ctttaccccg gcagcattga agtgaaaatg    1200
cacccgctgt cgatcaaacg cgcggtggcg aatatggtgg tcaacgccgc ccgttatggc    1260
aatggctgga tcaaagtcag cagcggaacg gagccgaatc gcgcctggtt ccaggtggaa    1320
gatgacggtc cggaattgc gccggaacaa cgtaagcacc tgttccagcc gtttgtccgc     1380
ggcgacagtg cgcgcaccat tagcggcacg ggattagggc tggcaattgt gcagcgtatc    1440
gtggataacc ataacgggat gctggagctt ggcaccagcg agcggggcgg gctttccatt    1500
cgcgcctggc tgccagtgcc ggtaacgcgg gcgcagggca cgacaaaaga agggtaa      1557
```

<210> SEQ ID NO 11
<211> LENGTH: 879
<212> TYPE: DNA
<213> ORGANISM: Artificial
<220> FEATURE:
<223> OTHER INFORMATION: (PhoB*:VP64): PhoB from Escherichia Coli
      (mutated in two amino acids in receiver domain) and VP64 from
      Herpes Simplex Virus

<400> SEQUENCE: 11

```
atggcgagac gtattctggt cgtagaagat gaagctccaa ttcgcgaaat ggtctgcttc     60
gtgctcgaac aaaatggctt tcagccggtc gaagcggaag attatgacag tgctgtgaat    120
caactgaatg aaccctggcc ggatttaatt ctccttgact ggatgttacc tggcggctcc    180
ggtatccagt tcatcaaaca cctcaagcgc gagtcgatga cccgggatat tccagtggtg    240
atgttgaccg ccagagggga agaagaagat cgcgtgcgcg ccttgaaaac cggcgcggat    300
gactatatcc ctaagccgtt taacccgaag agctggtgg cgcgaatcaa agcggtaatg    360
cgccgtattt cgccaatggc ggtggaagag gtgattgaga tgcagggatt aagtctcgac    420
ccgacatctc accgagtgat ggcgggcgaa gagccgctgg agatggggcc gacagaattt    480
```

```
aaactgctgc acttttttat gacgcatcct gagcgcgtgt acagccgcga gcagctgtta        540
aaccacgtct ggggaactaa cgtgtatgtg aagaccgcca cggtcgatgt ccacattcgt        600
cgcctgcgta aagcactgga gcccggcggg catgaccgca tggtgcagac cgtgcgcggt        660
acaggatatc gttttcaac ccgcttttaa accgggtata gatttagcac tagattcgcg         720
gatgctttgg atgatttcga tttagatatg cttgggagtg atgctctcga tgattttgat        780
cttgatatgc ttggatcaga tgctcttgat gatttcgatt tggacatgct tggatctgat        840
gctttagatg atttcgatct tgatatgctt ggttcatag                               879
```

<210> SEQ ID NO 12
<211> LENGTH: 1959
<212> TYPE: DNA
<213> ORGANISM: Artificial
<220> FEATURE:
<223> OTHER INFORMATION: (FLS-Trg-CR3-PhoR): Bacterial sequences from Escherichia Coli

<400> SEQUENCE: 12

```
atgaagttac tctcaaagac cttttttgata ttaactctca ccttcttctt ctttggcatt        60
gcactagcga aaatgaatac aactccctca cagcgattag ttttttttgca tcacatcagg       120 ttggttccgt tatttgcctg cattctaggc ggtatcttag ttctattcgc attaagttca       180
gccctggctg ctatttcct ctggcaggcc gatcgcgatc agcgtgatgt tactgcggag        240
attgagattc ggaccgggtt agcgaacagt tcagattttt tgcgttcagc ccggatcaat       300
atgattcagg ccggggctgc gagtcgtatt gcggaaatgg aagcaatgaa gcgaaatatt       360
gcgcaagccg aatcggagat taaacagtcg cagcaaggtt atcgtgctta tcagaatcga       420
ccggtgaaaa cacctgctga tgaagccctc gacactgaat taaatcaacg ctttcaggct       480
tatatcacgg gtatgcaacc tatgttgaaa atgccaaaa atggcatgtt tgaagcgatt       540
atcaatcatg aaagtgagca gatccgaccg ctggataatg cttataccga tattttgaac      600
aaagccgtta agatacgtag caccagagcc aaccaactgg cggaactggc ccatcagcgc      660
acccgcctgg gtgggatgtt catgattggc gcgtttgtgc ttgccctggt catgacgctg      720
ataacattta tggtgctacg tcggatcgtc attcgtccac tgcaacatgc cgcacaacgg      780
attgaaaaaa tcgccagtgg cgatctgacg atgaatgatg aaccggcggg tcgtaatgaa      840
atcggtcgct taagtcgtca tttacagcat atgagctggg aaccgctact atacggctta     900
caccagatgc agctgcgaaa taaaaaacgc cgccgtgaac tgggcaatct gattaaacgc     960
tttcgtagcg gcgcggagtc gctgcccgac gcggtggtgc tgaccacgga gagggcggt     1020 attttctggt gtaacggtct ggcgcaacaa attcttggtt tgcgctggcc ggaagataac    1080
gggcagaaca tccttaacct actgcgttac ccggagttta cgcaatatct gaaaacgcgt    1140 gattttctc gcccgctcaa tctggtgctc aacaccgggc ggcatctgga aattcgcgtc     1200
atgccttata cccacaaaca gttgctgatg gtggcgcgtg atgtcacgca aatgcatcaa    1260
ctggaagggg cgcggcgtaa ctttttttgcc aacgtgagcc atgagttacg tacgccattg    1320
accgtgttac agggttacct ggagatgatg aatgagcagc cgctggaagg cgcggtacgc    1380
gaaaaagcgt tgcacaccat gcgcgagcag acccagcgga tggaaggact ggtgaagcaa    1440
ttgctgacgc tgtcgaaaat agaagccgca ccgacgcatt tgctcaatga aaaggttgat    1500
gtgccgatga tgctgcgcgt tgttgagcgc gaggctcaga ctctgagtca gaaaaaacag    1560
acatttacct ttgagataga taacggcctc aaggtgtctg gcaacgaaga tcagctacgc    1620
```

| | |
|---|---|
| agtgcgattt cgaacctggt ctataacgcc gtgaatcata cgccggaagg cacgcatatc | 1680 |
| accgtacgct ggcagcgagt gccgcacggt gccgaattta gcgttgaaga taacggaccg | 1740 |
| ggcattgcac cggagcatat tccgcgcctg accgagcgtt tttatcgcgt tgataaagcg | 1800 |
| cgttcccggc aaaccggcgg tagcggatta gggttagcga tcgtgaaaca tgctgtgaat | 1860 |
| catcacgaaa gtcgcctgaa tattgagagt acagtaggaa aaggaacacg tttcagtttt | 1920 |
| gttatcccgg aacgtttaat tgccaaaaac agcgattaa | 1959 |

```
<210> SEQ ID NO 13
<211> LENGTH: 861
<212> TYPE: DNA
<213> ORGANISM: Artificial
<220> FEATURE:
<223> OTHER INFORMATION: (AtPhoB"VP64 preliminary): PhoB from
      Escherichia Coli and VP64 from Herpes Simplex Virus

<400> SEQUENCE: 13
```

| | |
|---|---|
| ggtaccatgg caaggcgtat tcttgtagtg gaggatgagg ctcccataag agaaatggtt | 60 |
| tgctttgttt tagagcagaa tggatttcaa ccagtcgagg cagaagatta cgacagtgcg | 120 |
| gttaaccaac ttaatgagcc gtggcctgat ctgatcctgc ttgattggat gctgccaggg | 180 |
| ggtagtggta tccaatttat caagcacttg aaaagagaat caatgacgcg tgatattcct | 240 |
| gtcgtaatgc ttactgcgag aggcgaggaa gaagacaggg taagaggact tgaaactggt | 300 |
| gctgacgact atattactaa accatttcct cctaaagaac tcgttgcaag gattaaagca | 360 |
| gtgatgaggc gtattagtcc tatggctgtc gaagaagtga ttgaaatgca ggggcttagt | 420 |
| ctggacccga catctcatag agtgatggca ggggaagaac ctctcgagat gggtccaact | 480 |
| gaatttaagt tgcttcattt ctttatgacc catccagaac gagtgtatag tagagagcaa | 540 |
| ctcttgaacc acgtctgggg aacaaacgtg tacgttgaag atagaacagt agatgtgcac | 600 |
| attcggagac ttcggaaagc acttgaaccc ggagggcatg atcgtatggt tcaaactgtt | 660 |
| cgaggaaccg ggtatagatt tagcactaga ttcgcggatg ctttggatga tttcgattta | 720 |
| gatatgcttg ggagtgatgc tctcgatgat tttgatcttg atatgcttgg atcagatgct | 780 |
| cttgatgatt tcgatttgga catgcttgga tctgatgctt tagatgattt cgatcttgat | 840 |
| atgcttggtt catagaagct t | 861 |

```
<210> SEQ ID NO 14
<211> LENGTH: 22
<212> TYPE: DNA
<213> ORGANISM: Escherichia coli
<220> FEATURE:
<221> NAME/KEY: misc_feature
<222> LOCATION: (22)..(22)
<223> OTHER INFORMATION: n is a, c, g, or t

<400> SEQUENCE: 14
```

| | |
|---|---|
| ctgtcataya yctgtcacay yn | 22 |

```
<210> SEQ ID NO 15
<211> LENGTH: 26
<212> TYPE: DNA
<213> ORGANISM: Artificial
<220> FEATURE:
<223> OTHER INFORMATION: FMV forward primer

<400> SEQUENCE: 15
```

| | |
|---|---|
| atttagcagc attccagatt gggttc | 26 |

<210> SEQ ID NO 16
<211> LENGTH: 27
<212> TYPE: DNA
<213> ORGANISM: Artificial
<220> FEATURE:
<223> OTHER INFORMATION: TB reverse primer

<400> SEQUENCE: 16
agagaaatgt tctggcacct gcacttg                                27

<210> SEQ ID NO 17
<211> LENGTH: 26
<212> TYPE: DNA
<213> ORGANISM: Artificial
<220> FEATURE:
<223> OTHER INFORMATION: PEX secrectory sequence primer 1

<400> SEQUENCE: 17
cttcggatcc atggagaggc cctttg                                 26

<210> SEQ ID NO 18
<211> LENGTH: 30
<212> TYPE: DNA
<213> ORGANISM: Artificial
<220> FEATURE:
<223> OTHER INFORMATION: PEX secrectory sequence primer 2

<400> SEQUENCE: 18
cgcgatggtg tctttggcca cgacggtata                             30

<210> SEQ ID NO 19
<211> LENGTH: 30
<212> TYPE: DNA
<213> ORGANISM: Artificial
<220> FEATURE:
<223> OTHER INFORMATION: RBP primer 1

<400> SEQUENCE: 19
tataccgtcg tggccaaaga caccatcgcg                             30

<210> SEQ ID NO 20
<211> LENGTH: 27
<212> TYPE: DNA
<213> ORGANISM: Artificial
<220> FEATURE:
<223> OTHER INFORMATION: RBP primer 2

<400> SEQUENCE: 20
aggagagctc tactgcttaa caaccag                                27

<210> SEQ ID NO 21
<211> LENGTH: 26
<212> TYPE: DNA
<213> ORGANISM: Artificial
<220> FEATURE:
<223> OTHER INFORMATION: Upper primer for SS

<400> SEQUENCE: 21
cttcggatcc atggagaggc cctttg                                 26

<210> SEQ ID NO 22
<211> LENGTH: 27
<212> TYPE: DNA
<213> ORGANISM: Artificial
<220> FEATURE:
<223> OTHER INFORMATION: RBP lower primer -continued

```
<400> SEQUENCE: 22
aggagagctc tactgcttaa caaccag                                          27

<210> SEQ ID NO 23
<211> LENGTH: 29
<212> TYPE: DNA
<213> ORGANISM: Artificial
<220> FEATURE:
<223> OTHER INFORMATION: FLS2 plasma membrane targeting primer 1

<400> SEQUENCE: 23
gttgcggatc catgaagtta ctctcaaag                                        29

<210> SEQ ID NO 24
<211> LENGTH: 30
<212> TYPE: DNA
<213> ORGANISM: Artificial
<220> FEATURE:
<223> OTHER INFORMATION: FLS2 plasma membrane targeting primer 2

<400> SEQUENCE: 24
gatacggtta atcattttcg ctagtgcaat                                       30

<210> SEQ ID NO 25
<211> LENGTH: 30
<212> TYPE: DNA
<213> ORGANISM: Artificial
<220> FEATURE:
<223> OTHER INFORMATION: TrzAHK4 primer 1

<400> SEQUENCE: 25
attgcactag cgaaaatgat taaccgtatc                                       30

<210> SEQ ID NO 26
<211> LENGTH: 28
<212> TYPE: DNA
<213> ORGANISM: Artificial
<220> FEATURE:
<223> OTHER INFORMATION: TrzAHK4 primer 2

<400> SEQUENCE: 26
gcgatcgctt acgacgaagg tgagatag                                         28

<210> SEQ ID NO 27
<211> LENGTH: 28
<212> TYPE: DNA
<213> ORGANISM: Artificial
<220> FEATURE:
<223> OTHER INFORMATION: PNOS-FlsTrzAHK4-TNOS primer 1

<400> SEQUENCE: 27
cttcaagctt gattccccgg atcatgag                                         28

<210> SEQ ID NO 28
<211> LENGTH: 28
<212> TYPE: DNA
<213> ORGANISM: Artificial
<220> FEATURE:
<223> OTHER INFORMATION: PNOS-FlsTrzAHK4-TNOS2 primer 2

<400> SEQUENCE: 28
cttcaagctt agagaaatgt tctggcac                                         28

<210> SEQ ID NO 29
```

```
<211> LENGTH: 32
<212> TYPE: DNA
<213> ORGANISM: Artificial
<220> FEATURE:
<223> OTHER INFORMATION: PhoB lower primer

<400> SEQUENCE: 29
gcaagcgatc gcttaatcgc tgttttggc aa                              32

<210> SEQ ID NO 30
<211> LENGTH: 24
<212> TYPE: DNA
<213> ORGANISM: Artificial
<220> FEATURE:
<223> OTHER INFORMATION: Cyclophilin primer 1

<400> SEQUENCE: 30
gcgttcccta aggtatactt cgac                                      24

<210> SEQ ID NO 31
<211> LENGTH: 22
<212> TYPE: DNA
<213> ORGANISM: Artificial
<220> FEATURE:
<223> OTHER INFORMATION: Cyclophilin primer 2

<400> SEQUENCE: 31
cccatgagaa cacacaccaa ac                                        22

<210> SEQ ID NO 32
<211> LENGTH: 24
<212> TYPE: DNA
<213> ORGANISM: Artificial
<220> FEATURE:
<223> OTHER INFORMATION: GUN4 primer 1

<400> SEQUENCE: 32
acgcaaaatc tggttaaaag tgaa                                      24

<210> SEQ ID NO 33
<211> LENGTH: 24
<212> TYPE: DNA
<213> ORGANISM: Artificial
<220> FEATURE:
<223> OTHER INFORMATION: GUN4 primer 2

<400> SEQUENCE: 33
ttgtgagcgg taagtgtcct aaag                                      24

<210> SEQ ID NO 34
<211> LENGTH: 22
<212> TYPE: DNA
<213> ORGANISM: Artificial
<220> FEATURE:
<223> OTHER INFORMATION: POR primer 1

<400> SEQUENCE: 34
ttgaccatca aggaacagag aa                                        22

<210> SEQ ID NO 35
<211> LENGTH: 22
<212> TYPE: DNA
<213> ORGANISM: Artificial
<220> FEATURE:
<223> OTHER INFORMATION: POR primer 2

<400> SEQUENCE: 35
```

-continued tatttgtgtt tcctgttata ga                                          22

<210> SEQ ID NO 36
<211> LENGTH: 22
<212> TYPE: DNA
<213> ORGANISM: Artificial
<220> FEATURE:
<223> OTHER INFORMATION: CHLASE primer 1

<400> SEQUENCE: 36
tagccccaca gttgtgcaaa tt                                          22

<210> SEQ ID NO 37
<211> LENGTH: 22
<212> TYPE: DNA
<213> ORGANISM: Artificial
<220> FEATURE:
<223> OTHER INFORMATION: CHLASE primer 2

<400> SEQUENCE: 37
aagtccgttg gtgcgcatgg tg                                          22

<210> SEQ ID NO 38
<211> LENGTH: 22
<212> TYPE: DNA
<213> ORGANISM: Artificial
<220> FEATURE:
<223> OTHER INFORMATION: RCCR primer 1

<400> SEQUENCE: 38
aatcttctcc gattgatttt gt                                          22

<210> SEQ ID NO 39
<211> LENGTH: 22
<212> TYPE: DNA
<213> ORGANISM: Artificial
<220> FEATURE:
<223> OTHER INFORMATION: RCCR primer 2

<400> SEQUENCE: 39
ctagagaaca ccgaaagctt ct                                          22

<210> SEQ ID NO 40
<211> LENGTH: 22
<212> TYPE: DNA
<213> ORGANISM: Artificial
<220> FEATURE:
<223> OTHER INFORMATION: PAO primer 1

<400> SEQUENCE: 40
tctatgaaca aaattgagtt ag                                          22

<210> SEQ ID NO 41
<211> LENGTH: 22
<212> TYPE: DNA
<213> ORGANISM: Artificial
<220> FEATURE:
<223> OTHER INFORMATION: PAO primer 2

<400> SEQUENCE: 41
ctactcgatt tcagaatgta ca                                          22